(12) United States Patent
Mee et al.

(10) Patent No.: US 8,987,504 B2
(45) Date of Patent: Mar. 24, 2015

(54) AMINOHYDROXYLATION OF ALKENES

(75) Inventors: Simon Peter Harold Mee, Lower Hutt (NZ); Andreas Luxenburger, Lower Hutt (NZ); Lawrence Daniel Harris, Wellington (NZ)

(73) Assignee: Victoria Link Limited, Wellington (NZ)

( * ) Notice: Subject to any disclaimer, the term of this patent is extended or adjusted under 35 U.S.C. 154(b) by 85 days.

(21) Appl. No.: 13/704,896

(22) PCT Filed: Jun. 20, 2011

(86) PCT No.: PCT/NZ2011/000116
§ 371 (c)(1),
(2), (4) Date: Jul. 1, 2013

(87) PCT Pub. No.: WO2011/159177
PCT Pub. Date: Dec. 22, 2011

(65) Prior Publication Data
US 2013/0274479 A1    Oct. 17, 2013

(30) Foreign Application Priority Data
Jun. 18, 2010 (NZ) .......... 586287
Dec. 6, 2010 (NZ) .......... 589724

(51) Int. Cl.
C07C 269/06 (2006.01)
C07C 227/20 (2006.01)
C07F 9/40 (2006.01)
C07D 307/60 (2006.01)
C07D 498/04 (2006.01)
C07D 307/33 (2006.01)
C07D 207/14 (2006.01)
C07D 491/048 (2006.01)
C07D 207/273 (2006.01)
C07C 271/08 (2006.01)

(52) U.S. Cl.
CPC ............ C07C 269/06 (2013.01); C07F 9/4075 (2013.01); C07F 9/4006 (2013.01); C07D 307/60 (2013.01); C07F 9/40 (2013.01); C07D 498/04 (2013.01); C07D 307/33 (2013.01); C07D 207/14 (2013.01); C07D 491/048 (2013.01); C07D 207/273 (2013.01); C07C 271/08 (2013.01)
USPC .................................. 560/160; 558/172

(58) Field of Classification Search
CPC ...... C07C 227/20; C07F 9/40; C07D 491/048
USPC .................. 560/160; 558/172; 548/224
See application file for complete search history.

(56) References Cited

U.S. PATENT DOCUMENTS

| 4,160,077 | A | 7/1979 | Brooks et al. |
|---|---|---|---|
| 4,160,866 | A | 7/1979 | Brooks et al. |
| 4,409,367 | A | 10/1983 | Beijleveld et al. |
| 4,871,855 | A | 10/1989 | Marko et al. |
| 4,965,364 | A | 10/1990 | Marko et al. |
| 5,126,494 | A | 6/1992 | Gilheany et al. |
| 5,227,543 | A | 7/1993 | Sharpless et al. |
| 5,260,461 | A | 11/1993 | Hartung et al. |
| 5,516,929 | A | 5/1996 | Sharpless et al. |
| 5,767,304 | A | * 6/1998 | Sharpless et al. ........... 560/27 |
| 5,859,281 | A | 1/1999 | Sharpless et al. |
| 5,994,583 | A | 11/1999 | Sharpless et al. |
| 6,008,376 | A | 12/1999 | Sharpless et al. |
| 6,057,473 | A | 5/2000 | Sharpless et al. |
| 6,372,911 | B1 | 4/2002 | Barta et al. |
| 6,509,506 | B1 | 1/2003 | Sharpless et al. |
| 6,573,387 | B1 | 6/2003 | Sharpless et al. |
| 2001/0029306 | A1 | 10/2001 | Wuts |
| 2008/0090883 | A1 | 4/2008 | Shan et al. |

FOREIGN PATENT DOCUMENTS

| GB | 1 519 877 | 8/1978 |
|---|---|---|
| GB | 1519877 | * 8/1978 |
| WO | 89/06225 A1 | 7/1989 |
| WO | 91/16322 A2 | 10/1991 |
| WO | 92/20677 A1 | 11/1992 |
| WO | 93/07142 A1 | 4/1993 |
| WO | 97/44312 A1 | 11/1997 |
| WO | 97/44316 A1 | 11/1997 |
| WO | 97/46516 A1 | 12/1997 |
| WO | 98/27051 A2 | 6/1998 |
| WO | 98/42657 A1 | 10/1998 |
| WO | 00/10977 A1 | 3/2000 |
| WO | 01/14315 A1 | 3/2001 |
| WO | 01/64625 A1 | 9/2001 |
| WO | 2007/145888 A2 | 12/2007 |

OTHER PUBLICATIONS

Bergmeier, "The Synthesis of Vicinal Amino Alcohols," *Tetrahedron* 56:2561-2576, 2000.
Blattner et al., "Syntheses of the Fungicide/Insecticide Allosamidin and a Structural Isomer," *J. Chem. Soc. Perkin Trans.* 1:3411-3421, 1994.
Bodkin et al., "The Sharpless asymmetric aminohydroxylation," *J. Chem. Soc., Perkin Trans.* 1:2733-2746, 2002.

(Continued)

*Primary Examiner* — Kamal Saeed
(74) *Attorney, Agent, or Firm* — Seed IP Law Group PLLC

(57) ABSTRACT

The invention relates to a process for the aminohydroxylation of alkenes using N-oxycarbamate reagents, e.g. N-acyloxycarbamate, N-alkyloxycarbonyloxycarbamate and N-aralkoxycarbonyloxycarbamate reagents. The invention particularly relates to an intermolecular aminohydroxylation reaction that can be carried out in the absence of added base. The invention also relates to novel N-oxycarbamate reagents that are stable crystalline materials. The process of the invention is useful in the synthesis of compounds having a vicinal amino alcohol moiety, such as biologically active compounds.

16 Claims, 6 Drawing Sheets

(56) References Cited

OTHER PUBLICATIONS

Bodkin et al., "The Sharpless asymmetric aminohydroxylation reaction: optimizing ligand/substrate control of regioselectivity for the synthesis of 3- and 4-aminosugars," *Org. Biomol. Chem.* 6:2544-2553, 2008.

Bruncko et al., "N-Bromoacetamide—A New Nitrogen Source for the Catalytic Asymmetric Aminohydroxylation of Olefins," *Angew. Chem. Int. Ed. Engi.* 36(13/14):1483-1486, 1997.

Christie et al., "Osmium and Palladium: Complementary Metals in Alkene Activation and Oxidation," *Synthesis* 9:1325-1341, 2008.

Demko et al., "Primary Amides. A General Nitrogen Source for Catalytic Asymmetric Aminohydroxylation of Olefins," *Organic Letters* 2(15):2221-2223, 2000.

Donohoe et al., "N-Sulfonyloxy Carbamates as Reoxidants for the Tethered Aminohydroxylation Reaction," *J. Am. Chem. Soc.* 128:2514-2515, 2006.

Donohoe et al., "Recent Developments in Methodology for the Direct Oxyamination of Olefins," *Chem. Eur. J.* 17:58-76, 2011.

Donohoe et al., "The regioselective aminohydroxylation of allylic carbamates," *Chem Commun.*, pp. 2078-2079, 2001.

Donohoe et al., "Tethered Aminohydroxylation: Dramatic Improvements to the Process," *Organic Letters* 9(9):1725-1728, 2007.

Donohoe et al., "The Tethered Aminohydroxylation (TA) of Cyclic Allylic Carbamates," *J. Am. Chem. Soc.* 124:12934-12935, 2002.

Donohoe et al., "The tethered aminohydroxylation (TA) reaction," *Org. Biomol. Chem.* 1:2025-2028, 2003.

Elliott et al., "Studies towards the total synthesis of lycoposerramine A. Synthesis of a model for the tetracyclic core," *Org. Biomol. Chem.* 7:3455-3462, 2009.

Gainsford et al., "(9H-Fluoren-9-yl)methyl N-{(2R,3R,4S)-4-hydroxy-2-[(2S,5R)-2-isopropyl-5-methylcyclohexyloxy]-5-oxooxolan-3-yl}-carbamate propan-2-ol 0.334-solvate," *Acta. Cryst. E*68:o403-o404, 2012.

GlycoSyn, "Improved Technology for the Base-free, Aminohydroxylation of Alkenes," brochure, published after Sep. 13, 2011, 2 pages.

GlycoSyn, "Aminohydroxylation Reagents," retrieved on Oct. 10, 2014, from http://www/glycosyn.com/aminohydroxylation-reagents, 1 page.

Goossen et al., "Catalytic Asymmetric Aminohydroxylation with Amino-Substituted Heterocycles as Nitrogen Sources," *Angew. Chem. Int. Ed.* 38(8)1080-1083, 1999.

Harris et al., "Alkyl 4-Chlorobenzoyloxycarbamates as Highly Effective Nitrogen Source Reagents for the Base-Free, Intermolecular Aminohydroxylation Reaction," *J. Org. Chem.* 76:358-372, 2011.

Harris et al., "Orthogonally-Protected Versatile Heterocyclic Chiral Scaffolds by New Aminohydroxylation Methodology," Poster from 23rd International Congress on Heterocyclic Chemistry, Glasgow, Scotland, Jul. 31-Aug. 4, 2011, 1 page.

Horner et al., "Umlagerung Und Thermischer Zerfall Acylierter Hydroxylamine," *Liebigs. Ann. Chem.* 602:24-47, 1957.

IRL Solutions, "Social science: R&D collaboration set to revolutionise treatment of autism," Industrial Research Limited, Spring 2011, 16 pages.

Klauber, "Chapter 4: Results and discussion—Development of the osmium-mediated aminohydroxylation reaction," thesis, University of Oxford, 2008, 44 pages.

Klauber et al., "N-Sulfonyloxy carbamates as reoxidants for aminohydroxylation reactions," Poster from ACS National Conference, Sep. 10-14, 2006, 1 page.

Kodama et al., "Design, synthesis, and evaluation of a novel bridged nucleic acid, 2',5'-BNA$^{ON}$, with S-type sugar conformation fixed by N-O linkage," *Tetrahedron* 65:2116-2123, 2009.

Li, "Sharpless asymmetric amino-hydroxylation," *Name Reactions: A Collection of Detailed Mechanisms and Synthetic Applications*, Springer International Publishing, Switzerland, 2014, pp. 546-548.

Li et al., "Catalytic Asymmetric Aminohydroxylation (AA) of Olefins," *Angew. Chem. Int. Ed. Engl.* 35(4)451-454, 1996.

Li et al., "N-Halocarbamate Salts Lead to More Efficient Catalytic Asymmetric Aminohydroxylation," *Angew. Chem. Int. Ed. Engl.* 35(23/24):2813-2817, 1996.

Luxenburger, "Technology Showcase: Chiral Pharmaceutical Technologies," NZBio Conference, Auckland, New Zealand, Mar. 21, 2011, 21 pages.

Luxenburger, "Chiral Pharmaceutical Technologies," Lecture/Seminar at the Institute of Pharmacy at the University of Kiel, Germany, Apr. 12, 2011, 40 pages.

Luxenburger, "Chiral Pharmaceutical Technologies," Lecture/Seminar at the Ecole Nationale Superieure de Chemie (CNRS) de Rennes, France, Apr. 4, 2011, 40 pages.

Luxenburger, "Chiral Pharmaceutical Technologies," New Zealand Institute of Chemistry (NZIC) Conference, Hamilton, New Zealand, Nov. 30, 2011, 26 pages.

Luxenburger, "Vicinal Aminohydroxylation made good? Alkyl 4-Chlorobenzoyloxycarbamates as efficient Reagents under *base-free* Reaction Conditions," 241$^{st}$ ACS National Meeting & Exposition, Anaheim, CA, Mar. 28, 2011, 25 Pages.

Marmer et al., "The Preparation and Reactions of Novel O-Acylhydroxylamines," *J. Org. Chem.* 37(22):3520-3523, 1972.

O'Brien et al., "Asymmetric aminohydroxylation of substituted styrenes: applications in the synthesis of enantiomerically enriched arylglycinols and a dimine," *J. Chem. Soc., Perkin Trans.* 1:2519-2526, 1998.

Oesper et al., "Some New Hydroxy-Urethans and Chromo-Isomeric Silver Salts of Their Acyl Derivatives," *J. Am. Chem. Soc.* 47:422-428, 1925.

Reddy et al., "From Styrenes to Enantiopure αArylglycines in Two Steps," *J. Am. Chem. Soc.* 120:1207-1217, 1998.

Reddy et al., "N-Chloro-N-Sodio-2-Trimethylsilyl Ethyl Carbamate: A New Nitrogen Source for the Catalytic *Asymmetric* Aminohydroxylation," *Tetrahedron Letters* 39:3667-3670, 1998.

Rudolph et al., "Smaller Substituents on Nitrogen Facilitate the Osmium-Catalyzed Asymmetric Aminohydroxylation," *Angew. Chem. Int. Ed. Engl.* 35(23/24):2810-2813, 1996.

Sharpless et al., "A New Reaction. Stereospecific Vicinal Oxyamination of Olefins by Alkyl Imido Osmium Compounds," *Journal of the American Chemical Society* 97(8)2305-2307, Apr. 16, 1975.

Sigma-Aldrich, "(9H-Fluoren-9-yl)methyl benzoyloxycarbamate," retrieved on Jul. 10, 2014, from http://www.sigmaaldrich.com/catalog/product/aldrich/ahr0003?lang=en&region=US, 1 page.

Zinner, "Darstellung und Reaktionen einiger substituierter N-Hydroxy-urethane," *Archive Der Pharmazie* 292:329-336, 1959.

\* cited by examiner

AMINOHYDROXYLATION OF ALKENES

TECHNICAL FIELD

This invention relates to a process for the aminohydroxylation of alkenes using N-oxycarbamate reagents, e.g. N-acyloxycarbamate, N-alkyloxycarbonyloxycarbamate and N-aralkoxycarbonyloxycarbamate reagents. The invention particularly relates to an intermolecular aminohydroxylation reaction that can be carried out in the absence of added base. The invention also relates to novel N-oxycarbamate reagents that are stable crystalline materials.

BACKGROUND

The Sharpless aminohydroxylation reaction (also known as the Sharpless oxyamination reaction), first published in 1975 (Sharpless, K. B.; Patrick, D. W.; Truesdale, L. K.; Biller, S. A., *J. Am. Chem. Soc.* 1975, 97, 2305-2307), and the Sharpless asymmetric aminohydroxylation reaction, first published in 1996 (Li, G.; Chang, H.-T.; Sharpless, K. B. *Angew. Chem. Int. Ed. Engl.,* 1996, 35, 451-453), allow the formation of a vicinal amino alcohol moiety from a simple alkene, in one step. The aminohydroxylation is effected by an osmium(VIII) complex that most favourably is present in catalytic amounts. The vicinal amino alcohol moiety is present in many biologically active compounds and these Sharpless aminohydroxylation reactions have therefore been used in many syntheses.

However, the aminohydroxylation reaction, while useful, is not without its limitations. The aminohydroxylation reaction requires a nitrogen source reagent, such as an amide, a sulfonamide or a carbamate. Carbamates have been widely used, but the reaction conditions typically involve the use of t-butyl hypochlorite in the presence of sodium hydroxide to produce an N-halocarbamate salt in situ, which is then used in the reaction. Such N-halocarbamate reagents can be unstable and difficult to store. In addition, the presence of base is an issue where base-sensitive substrates are being used. Further, the t-butyl hypochlorite has to be prepared prior to use by reaction of aqueous sodium hypochlorite, t-butanol and acetic acid, and used in reduced lighting as it is sensitive to photodecomposition.

Donohoe et al. have reported "tethered" (intramolecular) aminohydroxylation reactions, which can be carried out under "base-free" reaction conditions (Donohoe, T. J.; Chughtai, M. J.; Klauber, D. J.; Griffin, D.; Cambell, A. D. *J. Am. Chem. Soc.* 2006, 128, 2514-2515; Donohoe, T. J.; Bataille, C. J. R.; Gattrell, W.; Kloesges, J.; Rossignol, E. *Org. Lett.* 2007, 9, 1725-1728). However, yields for these reactions can be variable. The tethered reactions operate in a stereospecific fashion which means that they are not suited for use in the synthesis of compounds where certain stereochemistries may be desired.

Klauber et al. have reported the intermolecular aminohydroxylation of an alkene using the N-acyloxycarbamate (i):

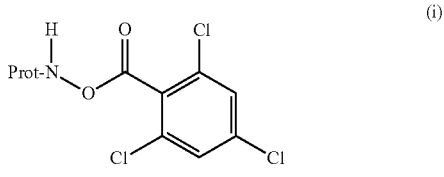

Prot = Boc or Teoc as a nitrogen source (Klauber D. J., Donohoe T. J., Chughtai M. J. and Campbell A. D., 232nd ACS National Conference, September 2006; Klauber D. J., PhD Thesis, Oxford University). However, this reaction was optimally carried out under basic conditions (LiOH, 1.32 equivalents), which, as discussed above, are not desirable in situations where base-sensitive substrates are being used.

While investigating the total synthesis of the natural product allosamidin the applicant encountered some issues when using the aminohydroxylation reaction to prepare a key intermediate in the process. The substrate for that aminohydroxylation reaction has base-sensitive substituents, and the tethered aminohydroxylation reaction is not an option in this case, so using published methods results in only limited success.

Facile routes to the synthesis of biologically active compounds such as allosamindin are needed. The applicant has now found that the aminohydroxylation of alkenes can be achieved in a reliable manner and frequently in high yield using N-oxycarbamate compounds as nitrogen source reagents, and that the reaction can be carried out under "base-free" conditions.

It is therefore an object of the present invention to provide a process for the aminohydroxylation of alkenes, or to at least provide a useful choice. It is another object of the invention to provide nitrogen source reagents for the aminohydroxylation reaction, or to at least provide a useful choice.

SUMMARY OF INVENTION

In a first aspect, the present invention provides a process for preparing a β-hydroxycarbamate compound from an alkene, using an aminohydroxylation reaction, the process including the step of:
  reacting the alkene with an N-oxycarbamate compound, in the presence of an osmium compound as a catalyst, to give the β-hydroxycarbamate compound;
where the process is optionally carried out in the absence of added base.

In a second aspect, the present invention provides a process for preparing a β-hydroxycarbamate compound from an alkene, using an aminohydroxylation reaction, the process including the step of:
  reacting the alkene with an N-acyloxycarbamate compound, in the presence of an osmium compound as a catalyst, to give the β-hydroxycarbamate compound;
where the process is carried out in the absence of added base.

In a third aspect, the present invention provides a process for preparing a β-hydroxycarbamate compound from an alkene, using an aminohydroxylation reaction, the process including the step of:
  reacting the alkene with an N-alkyloxycarbonyloxycarbamate or an N-aralkoxycarbonyloxycarbamate compound, in the presence of an osmium compound as a catalyst, to give the β-hydroxycarbamate compound;
where the process is optionally carried out in the absence of added base.

Preferably the process is carried out in the absence of added base.

In some examples of the process, the osmium catalyst is osmium tetroxide, potassium osmate(VI) dihydrate or osmium(III) trichloride or immobilized osmium catalysts such as Os EnCat™40 Catalyst (Reaxa Limited, Blackley, Manchester, UK) which is osmium tetraoxide microencapsulated within a porous cross-linked polyurea matrix (S. V. Ley et al, *Org. Lett.,* 2003, 5, 185). The osmium catalyst is present in catalytic amounts, such as, e.g., in the range of about 0.1 mol % to about 20 mol %, for example about 1 mol % to 10 mol %, e.g. about 4 mol %.

In some examples of the process, the reaction of the alkene and the N-oxycarbamate compound, e.g. the N-acyloxycarbamate, N-alkyloxycarbonyloxycarbamate or N-aralkoxycarbonyloxycarbamate compound, is carried out in an organic solvent containing water, such as a mixed solvent system selected from the group consisting of acetonitrile/water, isopropanol/water n-propanol/water, t-butanol/water, acetone/water, tetrahydrofuran/water, dioxane/water and dimethylformamide/water. Preferably the solvent is acetonitrile/water. The amount of water present in the organic solvent/water mixture is preferably about 5%-60% v/v, such as about 12.5% v/v water in acetonitrile.

The alkene used in the process can be any suitable alkene, such as, for example, a mono-substituted or di-substituted alkene or a cyclic alkene.

Optionally, the reaction of the alkene and an N-acyloxycarbamate compound of the invention may be carried out in the presence of a chiral ligand, e.g. a chiral phthalazine (PHAL) or a chiral anthraquinone (AQN) ligand, e.g. $(DHQ)_2PHAL$, $(DHQD)_2PHAL$ or $(DHQ)_2AQN$, to effect asymmetric aminohydroxylation of the alkene. The amount of chiral ligand used is, for example, about 1 to 1.5 times the amount (mol %) of osmium catalyst used in the process, e.g. about 1.1 to 1.3 times the amount (mol %) of osmium catalyst used.

The reaction of the alkene and the N-oxycarbamate compound, e.g. the N-acyloxycarbamate, N-alkyloxycarbonyloxycarbamate or N-aralkoxycarbonyloxycarbamate compound, can be carried out at a temperature of about −10° C. to about 90° C., typically about 10° C. to about 30° C., for example about 18° C. to about 25° C.

In some examples of the process, the N-oxycarbamate compound is a compound of formula (II):

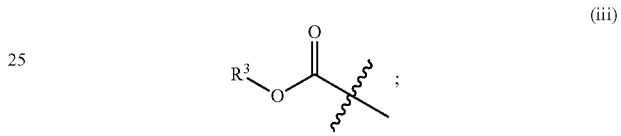

(II)

where:
$R^3$ is an optionally substituted alkyl group, an optionally substituted aralkyl group or an optionally substituted aryl group;
$R^4$ is a radical of formula (ii)

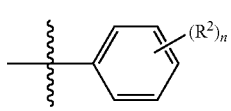

(ii)

or $R^4$ is $OR^5$;
$R^2$ is halogen, alkyl, alkoxy, dialkylamino, trialkylammonium, nitro, carboxy alkyl ester, alkylamide, —$SO_3H$, —$PO_3H_2$ or —COOH, where, when n is greater than 1, each $R^2$ is independently selected;
$R^5$ is an optionally substituted alkyl group or an optionally substituted aralkyl group; and
n is 0, 1, 2, 3, 4 or 5;

provided that the following compounds are excluded:
the compound where: $R^3$ is t-butyl; $R^4$ is a radical of formula (ii) where $R^2$ is Cl and n is 3; and
the compound where: $R^3$ is t-butyl; $R^4$ is a radical of formula (ii) where $R^2$ is methyl and n is 3.

In some examples of the process, the N-oxycarbamate compound is an N-acyloxycarbamate compound of formula (I):

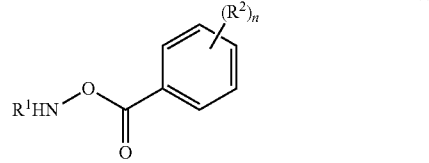

(I)

where
$R^1$ is a radical of formula (iii)

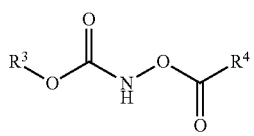

(iii)

$R^2$ is halogen, alkyl, alkoxy, dialkylamino, trialkylammonium, nitro, carboxy alkyl ester, alkylamide, —$SO_3H$, —$PO_3H_2$ or —COOH, where, optionally, when n is greater than 1, each $R^2$ is independently selected;
n is 0, 1, 2, 3, 4 or 5; and
$R^3$ is an optionally substituted alkyl group, an optionally substituted aralkyl group or an optionally substituted aryl group;
provided that the following compounds are excluded:
the compound where: $R^1$ is a radical of formula (iii) where $R^3$ is t-butyl; $R^2$ is Cl and n is 3; and
the compound where: $R^1$ is a radical of formula (iii) where $R^3$ is t-butyl; $R^2$ is methyl and n is 3.

In some examples of the process, the N-oxycarbamate compound is an N-alkyloxycarbonyloxycarbamate or an N-aralkoxycarbonyloxycarbamate compound of formula (III):

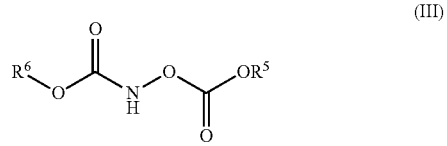

(III)

where:
$R^5$ is an optionally substituted alkyl group or an optionally substituted aralkyl group; and
$R^6$ is an optionally substituted alkyl group or an optionally substituted aralkyl group.

It is preferred that n is 0, 1, 2, 4 or 5, most preferably 0 or 1.

In some examples of the process, $R^3$ in the compound of formula (I) or (II) is a lower alkyl group, e.g. an ethyl group or a butyl group, e.g. a tert-butyl group.

In some examples of the process, $R^3$ in the compound of formula (I) or (II) is an alkyl group which is substituted with one or more substituents selected from the group consisting of halogen, —COOH, carboxy alkyl ester group, dialkylamino group, trialkylammonium group, alkylamide group and alkoxy group.

In some examples of the process, $R^3$ in the compound of formula (I) or (II) is an aryl or aralkyl group, each of which is substituted with one or more substituents selected from the group consisting of halogen, alkyl, —COOH, —SO$_3$H, —PO$_3$H$_2$, carboxy alkyl ester group, dialkylamino group, trialkylammonium group, nitro group, alkylamide group and alkoxy group.

In some examples of the process, $R^3$ in the compound of formula (I) or (II) is a substituted lower alkyl group, e.g. a 2,2,2-trichloroethyl group or a 2-trimethylsilylethyl group.

In some examples of the process, $R^3$ in the compound of formula (I) or (II) is an aryl group, e.g. a phenyl group.

In some examples of the process, $R^3$ in the compound of formula (I) or (II) is an aralkyl group, e.g. a benzyl group or a 9-fluorenylmethyl group.

In some examples of the process, $R^1$ in the compound of formula (I) is EtO$_2$C, MeO$_2$C, 2-trimethylsilylethoxycarbonyl, phenoxycarbonyl, 2,2,2-trichloroethoxycarbonyl, benzyloxycarbonyl, tert-butoxycarbonyl or 9-fluorenylmethoxycarbonyl.

In some examples of the process, $R^3$ in the compound of formula (I) or (II) is ethyl, methyl, 2-trimethylsilylethyl, phenyl, 2,2,2-trichloroethyl, benzyl, tert-butyl or 9-fluorenylmethyl.

In some examples of the process, $R^2$ in the compound of formula (I) or (II) is a halogen, e.g. chlorine.

In some examples of the process, n in the compound of formula (I) or (II) is 1. In some examples, $R^2$ in the compound of formula (I) or (II) is chlorine and n is 1. In some examples, $R^2$ in the compound of formula (I) or (II) is chlorine and n is 1, and the chlorine is in the 4-position.

In some examples of the process, $R^1$ in the compound of formula (I) is EtO$_2$C, MeO$_2$C, 2-trimethylsilylethoxycarbonyl, phenoxycarbonyl, 2,2,2-trichloroethoxycarbonyl, benzyloxycarbonyl, tert-butoxycarbonyl or 9-fluorenylmethoxycarbonyl, and n is 1.

In some examples of the process, $R^1$ in the compound of formula (I) is EtO$_2$C, MeO$_2$C, 2-trimethylsilylethoxycarbonyl, phenoxycarbonyl, 2,2,2-trichloroethoxycarbonyl, benzyloxycarbonyl, tert-butoxycarbonyl or 9-fluorenylmethoxycarbonyl, and n is 0.

In some examples of the process, $R^1$ in the compound of formula (I) is EtO$_2$C, MeO$_2$C, 2-trimethylsilylethoxycarbonyl, phenoxycarbonyl, 2,2,2-trichloroethoxycarbonyl, benzyloxycarbonyl, tert-butoxycarbonyl or 9-fluorenylmethoxycarbonyl, and $R^2$ is chlorine and n is 1.

In some examples of the process, n in the compound of formula (I) or (II) is greater than 1 and each $R^2$ is independently selected.

In some examples of the process, $R^5$ in the compound of formula (II) or (III) is lower alkyl, e.g. an ethyl group or a butyl group, e.g. a tert-butyl group.

In some examples of the process, $R^5$ in the compound of formula (II) or (III) is aralkyl, e.g. benzyl.

In some examples of the process, $R^3$ and $R^5$ in the compound of formula (II) are both lower alkyl, e.g. an ethyl group or a butyl group, e.g. a tert-butyl group.

In some examples of the process, $R^3$ and $R^5$ in the compound of formula (II) are both aralkyl, e.g. benzyl or 9-fluorenylmethyl.

In some examples of the process, $R^3$ and $R^5$ in the compound of formula (II) are the same. In other examples, $R^3$ and $R^5$ are different.

In some examples of the process, $R^5$ and $R^6$ in the compound of formula (III) are both lower alkyl, e.g. an ethyl group or a butyl group, e.g. a tert-butyl group.

In some examples of the process, $R^5$ and $R^6$ in the compound of formula (III) are both aralkyl, e.g. benzyl or 9-fluorenylmethyl.

In some examples of the process, $R^5$ and $R^6$ in the compound of formula (III) are the same.

In some examples of the process, the N-acyloxycarbamate compound is a compound selected from the group consisting of:

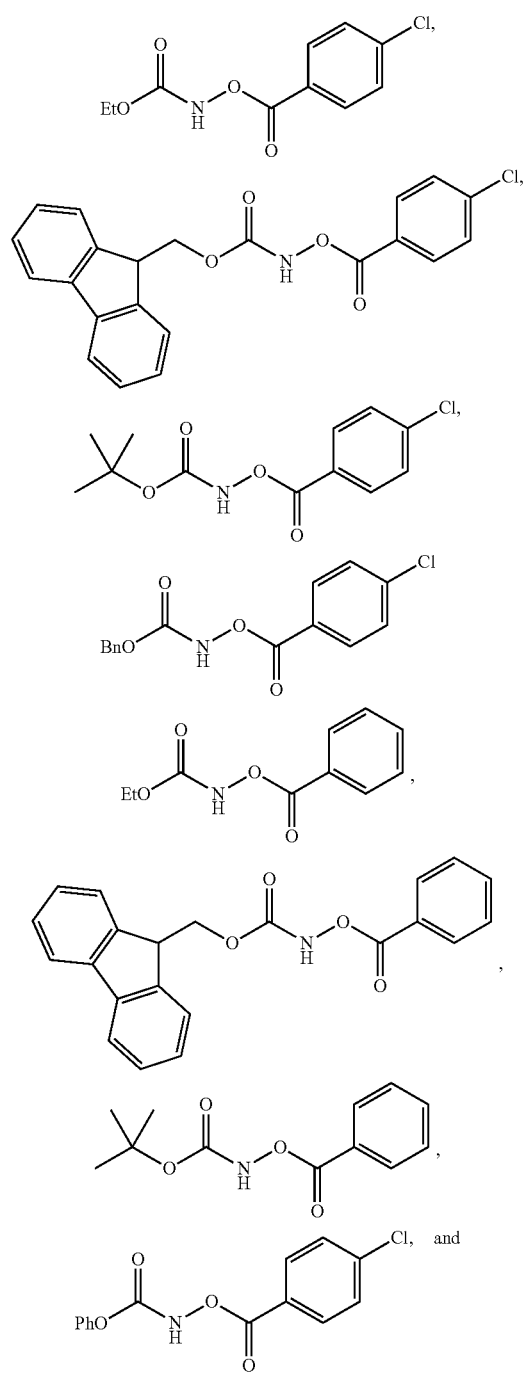

-continued

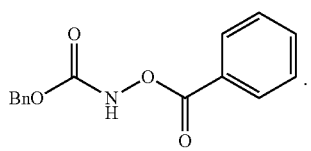

In some examples of the process, the N-alkyloxycarbonyloxycarbamate or N-aralkoxycarbonyloxycarbamate compound is a compound selected from the group consisting of:

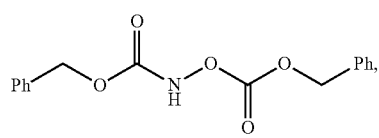

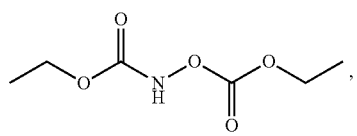

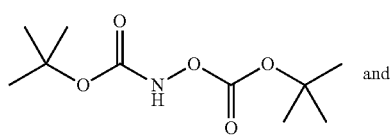

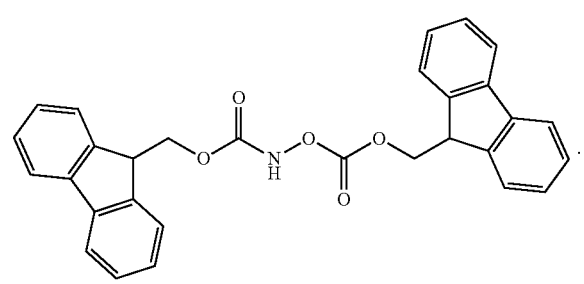

In another aspect the invention provides a compound selected from the group consisting of:

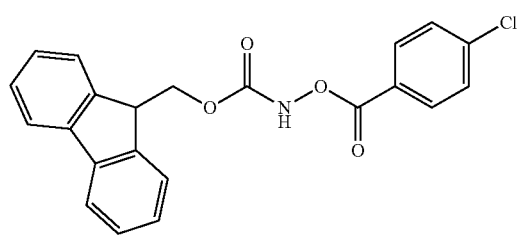

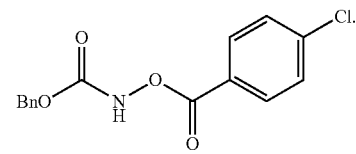

In another aspect the invention provides a compound selected from the group consisting of:

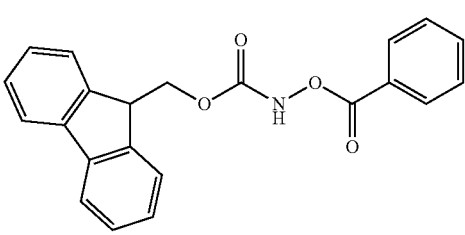

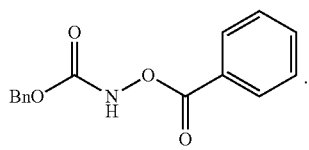

In another aspect the invention provides a compound of formula (IV)

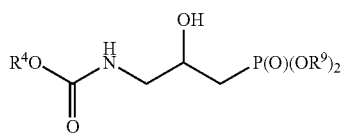

(IV)

where:
R⁴ is benzyl or 9-fluorenylmethyl group; and
R⁹ is a lower alkyl group.

The stereochemistry of the carbon C-2 of the above formula (IV) can be (R), (S) or racemic.

In another aspect the invention provides a compound selected from the group consisting of:

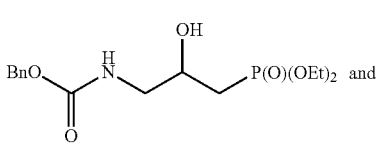

(V)

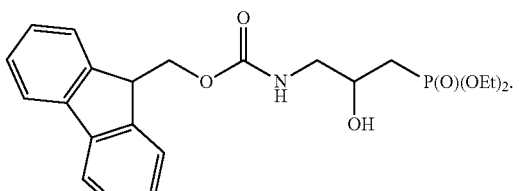

(VI)

The stereochemistry of the carbon C-2 of the above compounds (V) and (VI) can be (R), (S) or racemic.

The invention also provides a β-hydroxycarbamate compound when prepared by the process described above.

The invention further provides a compound of formula (VII), (VIII), (IX), (X), (XI) or (XII):

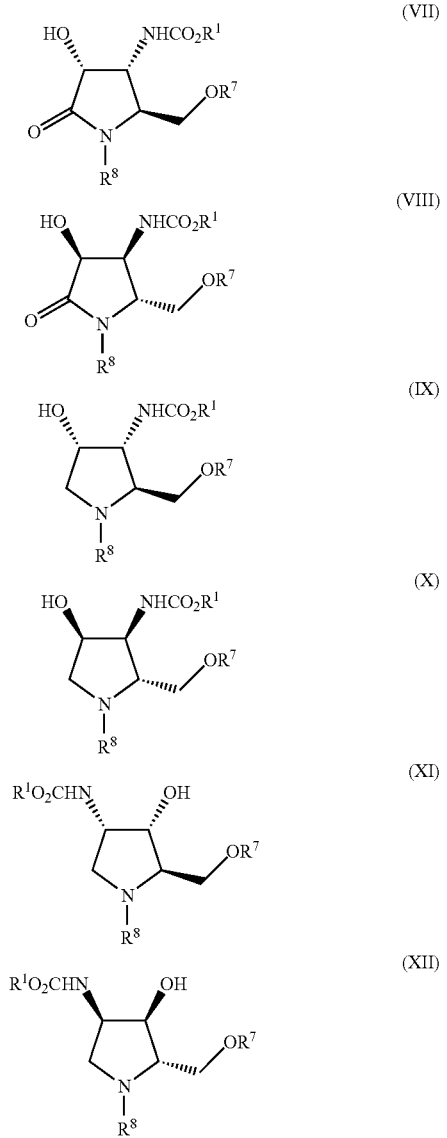

The invention further provides a compound of formula (XIII) or (XIV):

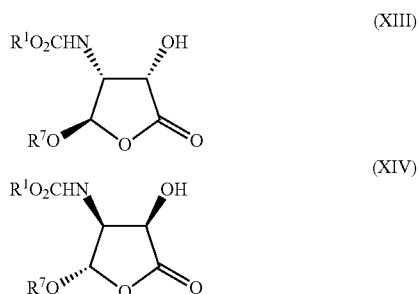

where:
R¹ is an optionally substituted alkyl group, an optionally substituted aralkyl group or an optionally substituted aryl group; and
R⁷ is hydrogen, an optionally substituted alkyl, aralkyl, aryl, alkylcarbonyl, aralkylcarbonyl or arylcarbonyl group, or an oxygen protecting group chosen from a tert-butyldimethylsilyl, tert-butyldiphenylsilyl or triethylsilyl group.

In some examples of the compounds of formula (VII), (VIII), (IX), (X), (XI), (XII), (XIII) or (XIV), R¹ is a lower alkyl group, e.g. a methyl, ethyl or butyl group, e.g. an ethyl or tert-butyl group.

In some examples of the compounds of formula (VII), (VIII), (IX), (X), (XI), (XII), (XIII) or (XIV), R¹ is an alkyl group which is substituted with one or more substituents selected from the group consisting of halogen, —COOH, carboxy alkyl ester group, dialkylamino group, trialkylammonium group, alkylamide group and alkoxy group.

In some examples of the compounds of formula (VII), (VIII), (IX), (X), (XI), (XII), (XIII) or (XIV), R¹ is an aryl or aralkyl group, each of which is substituted with one or more substituents selected from the group consisting of halogen, alkyl, —COOH, —SO₃H, —PO₃H₂, carboxy alkyl ester group, dialkylamino group, trialkylammonium group, nitro group, alkylamide group and alkoxy group.

In some examples of the compounds of formula (VII), (VIII), (IX), (X), (XI), (XII), (XIII) or (XIV), R¹ is a substituted lower alkyl group, e.g. a 2,2,2-trichloroethyl group or a 2-trimethylsilylethyl group.

In some examples of the compounds of formula (VII), (VIII), (IX), (X), (XI), (XII), (XIII) or (XIV), R¹ is an aryl group, e.g. a phenyl group.

In some examples of the compounds of formula (VII), (VIII), (IX), (X), (XI), (XII), (XIII) or (XIV), R¹ is an aralkyl group, e.g. a benzyl group or a 9-fluorenylmethyl group.

In some examples of the compounds of formula (VII), (VIII), (IX), (X), (XI), (XII), (XIII) or (XIV), R⁷ is an oxygen protecting group, e.g. a tert-butyldiphenylsilyl group.

In some examples of the compounds of formula (VII), (VIII), (IX), (X), (XI), (XII), (XIII) or (XIV), R¹ is a lower alkyl group, e.g. a methyl, ethyl or butyl group, e.g. an ethyl or tert-butyl group, and R⁷ is an oxygen protecting group, e.g. a tert-butyldiphenylsilyl group.

In some examples of the compounds of formula (VII), (VIII), (IX), (X), (XI) or (XII), R⁸ is a nitrogen protecting group, e.g. a tert-butoxycarbonyl group.

In some examples of the compounds of formula (VII), (VIII), (IX), (X), (XI) or (XII), R⁸ is a nitrogen protecting group, e.g. a tert-butoxycarbonyl group and R⁷ is an oxygen protecting group, e.g. a tert-butyldiphenylsilyl group.

where:
R¹ is an optionally substituted alkyl group, an optionally substituted aralkyl group or an optionally substituted aryl group;
R⁷ is hydrogen, an optionally substituted alkyl, aralkyl, aryl, alkylcarbonyl, aralkylcarbonyl or arylcarbonyl group, or an oxygen protecting group chosen from a tert-butyldimethylsilyl, tert-butyldiphenylsilyl or triethylsilyl group;
R⁸ is hydrogen, an optionally substituted arylsulfonyl group, or a nitrogen protecting group selected from a benzyl, 4-methoxybenzyl, 3,4-dimethoxybenzyl, (R)-α-methylbenzyl, (S)-α-methylbenzyl, (R)-4-methoxy-α-methylbenzyl, (S)-4-methoxy-α-methylbenzyl, benzhydryl, 9-(9-phenylfluorenyl), 4-methoxyphenyl, trifluoroacetyl, tert-butoxycarbonyl, methoxycarbonyl, ethoxycarbonyl, benzyloxycarbonyl, 9-fluorenylmethoxycarbonyl or 2,2,2-trichloroethoxycarbonyl group;
or R⁷ and R⁸ together form an optionally substituted (R)-, (S)- or (RS)-benzylidene acetal group.

In some examples of the compounds of formula (VII), (VIII), (IX), (X), (XI) or (XII), $R^7$ and $R^8$ together form an optionally substituted (R)-, (S)- or (RS)-benzylidene acetal group.

In some examples the compounds of formula (VII), (VIII), (IX), (X), (XI), (XII), (XIII) or (XIV) are prepared by the process of the invention.

In another aspect the invention provides a compound selected from the group consisting of:

(2R,3S,4S)-tert-Butyl 2-[(tert-butyldiphenylsilyloxy) methyl]-4-(ethoxycarbonylamino)-3-hydroxypyrrolidine-1-carboxylate

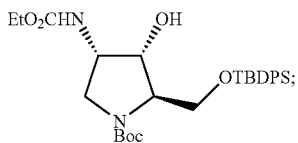

(2S,3R,4S)-tert-Butyl 2-[(tert-butyldiphenylsilyloxy) methyl]-3-(ethoxycarbonylamino)-4-hydroxypyrrolidine-1-carboxylate

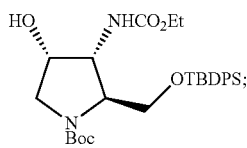

(2R,3S,4S)-tert-Butyl 4-(benzyloxycarbonylamino)-2-[(tert-butyldiphenylsilyloxy) methyl]-3-hydroxy-pyrrolidine-1-carboxylate

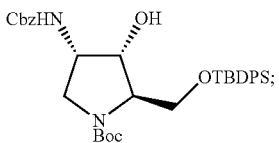

(2S,3R,4S)-tert-Butyl 3-(benzyloxycarbonylamino)-2-[(tert-butyldiphenylsilyloxy) methyl]-4-hydroxy-pyr-rolidine-1-carboxylate

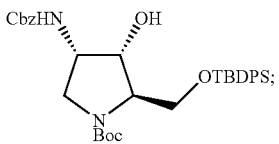

Ethyl (3S,6S,7S,7aR)-6-hydroxy-5-oxo-3-phenyl-hexahydropyrrolo[1,2-c]oxazol-7-yl carbamate

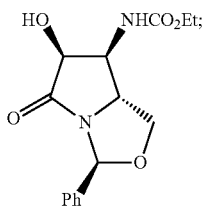

Ethyl (3R,6R,7R,7aS)-6-hydroxy-5-oxo-3-phenyl-hexahydropyrrolo[1,2-c]oxazol-7-yl carbamate

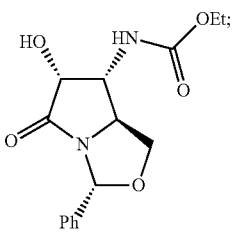 [SMILES: CCOC(=O)N[C@@H]1[C@H]2CO[C@H](c3ccccc3)N2C(=O)[C@@H]1O]

(2S,3R,4R)-tert-Butyl 3-(benzyloxycarbonylamino)-2-[(tert-butyldiphenylsilyl-oxy)methyl]-4-hydroxy-5-oxopyrrolidine-1-carboxylate

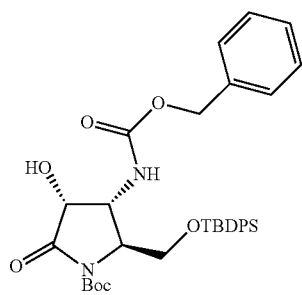

(2R,3S,4S)-tert-Butyl 3-(benzyloxycarbonylamino)-2-[(tert-butyldiphenylsilyl-oxy)methyl]-4-hydroxy-5-oxopyrrolidine-1-carboxylate

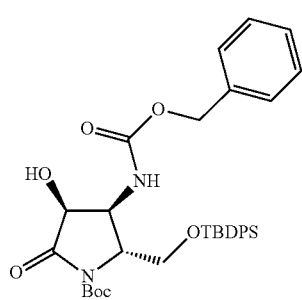

(2S,3R,4R)-tert-Butyl 2-[(tert-butyldiphenylsilyloxy)methyl]-3-(ethoxycarbonyl-amino)-4-hydroxy-5-oxopyrrolidine-1-carboxylate

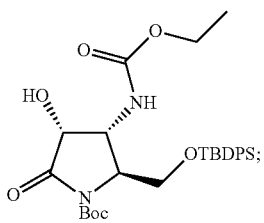

(9H-Fluoren-9-yl)methyl (1S,2S)-2-hydroxy-3-oxo-cyclohexylcarbamate

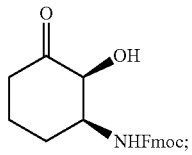

and (9H-Fluoren-9-yl)methyl (1R,2R)-2-hydroxy-3-oxo-cyclohexylcarbamate

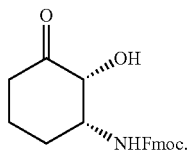

In another aspect the invention provides the compound (9H-Fluoren-9-yl)methyl (2R,3R,4S)-4-hydroxy-2-[(2S,5R)-2-isopropyl-5-methyl-cyclohexyloxy]-5-oxotetrahydrofuran-3-ylcarbamate

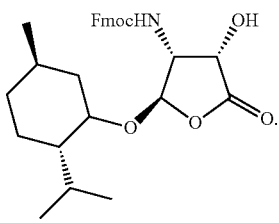

In another aspect, the invention provides a compound selected from the group consisting of:

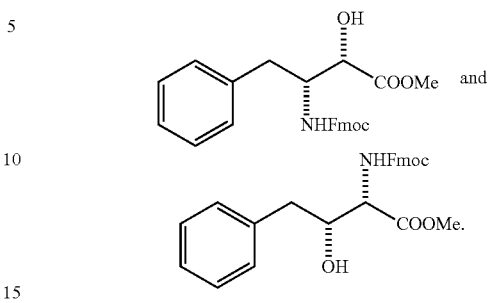

In some examples the above compounds are prepared by the process of the invention.

DETAILED DESCRIPTION

Definitions

The term "alkyl" means any saturated hydrocarbon radical having up to 30 carbon atoms and includes any $C_1$-$C_{25}$, $C_1$-$C_{20}$, $C_1$-$C_{15}$, $C_1$-$C_{10}$, or $C_1$-$C_6$ alkyl group, and is intended to include both straight- and branched-chain alkyl groups, and to include cyclic alkyl groups. Examples of alkyl groups include: methyl group, ethyl group, n-propyl group, iso-propyl group, n-butyl group, iso-butyl group, sec-butyl group, tert-butyl group, n-pentyl group, 1,1-dimethylpropyl group, 1,2-dimethylpropyl group, 2,2-dimethylpropyl group, 1-ethylpropyl group, 2-ethylpropyl group, n-hexyl group, 1-methyl-2-ethylpropyl group, cyclopropyl group, cyclobutyl group, cyclopentyl group, cyclohexyl group, cycloheptyl group and cyclooctyl group.

The term "lower alkyl" means any saturated hydrocarbon radical having from 1 to 6 carbon atoms and is intended to include straight- and branched-chain and cyclic alkyl groups.

Any alkyl group may optionally be substituted with one or more substituents selected from the group consisting of halogen, —COOH, carboxy alkyl ester group, dialkylamino group, trialkylammonium group, alkylamide group and alkoxy group. Furthermore, any cyclic alkyl group may optionally be substituted with one or more straight- or branched-chain alkyl groups.

The term "aryl" means an aromatic radical having 4 to 18 carbon atoms. Examples include monocyclic groups, as well as fused groups such as bicyclic groups and tricyclic groups. Some examples include phenyl group, 1-naphthyl group, 2-naphthyl group, azulenyl group, heptalenyl group, biphenyl group, fluorenyl group and anthracenyl group.

Any aryl group may optionally be substituted with one or more substituents selected from the group consisting of halogen, alkyl, alkoxy, dialkylamino, trialkylammonium, nitro, —COOH, —$SO_3H$, —$PO_3H_2$, carboxy alkyl ester, and alkylamide.

The term "aralkyl" means an aryl group covalently bound to an alkylene group, where alkylene has an analogous meaning to alkyl as defined above, and aryl group is as defined above. Examples include benzyl group and fluorenylmethyl group.

The term "alkoxy" means an —OR group, where R is alkyl as defined above.

The term "halogen" includes fluorine, chlorine, bromine and iodine.

The term "protecting group" means a group that selectively protects an organic functional group, temporarily masking the chemistry of that functional group and allowing other sites in the molecule to be manipulated without affecting the functional group. Suitable protecting groups are known to those skilled in the art and are described, for example, in *Protective Groups in Organic Synthesis* (3rd Ed.), T. W. Greene and P. G. M. Wuts, John Wiley & Sons Inc (1999). Examples of protecting groups include, but are not limited to: benzyloxycarbonyl group, 2,2,2-trichloroethyloxycarbonyl group, 2-trimethylsilylethyloxycarbonyl group, tert-butoxycarbonyl group and 9-fluorenylmethoxycarbonyl group.

The "nitrogen source reagent" used in the process of the present invention provides the source of the carbamoyl radical in the aminohydroxylation reaction.

It will be appreciated that alkenes can exist as cis and trans isomers. The scope of this invention is intended to cover all such isomeric forms of the compounds.

It will also be appreciated that the alkene moiety in a compound that undergoes the process of the present invention may be conjugated as in a lactam, lactone or α,β-unsaturated ketone. The scope of this invention is intended to cover all such conjugated alkenes.

It will also be appreciated that the compounds of formulae (I)-(XIV) can exist in the form of optical isomers, racemates and diastereomers, e.g. in the case that the substituent $R^1$ contains one or more chiral centres. The scope of this invention is intended to cover all possible stereoisomeric forms of the compounds of formulae (I)-(XIV).

Unless the context clearly requires otherwise, throughout the description and claims the terms "comprise", "comprising" and the like are to be construed in an inclusive sense, as opposed to an exclusive or exhaustive sense, that is to say, in the sense of "including, but not limited to".

The Nitrogen Source Reagent

In one aspect, the invention provides novel nitrogen source reagents for the aminohydroxylation reaction.

(a) N-Acyloxycarbamate Compounds of the Invention

The N-acyloxycarbamate nitrogen source reagents of the invention are synthesised as shown in Scheme 1.

Treatment of the appropriate starting material, e.g. ethyl chloroformate, methyl chloroformate, tert-butyl chloroformate, 2-trimethylsilyl chloroformate (Teoc), 2,2,2-trichloroethylchloroformate (Troc), phenyl chloroformate, benzyl chloroformate, di-tert-butyldicarbonate or fluorenylmethoxycarbonyl chloride (FmocCl) with hydroxylamine gives an N-hydroxy carbamate (Fuller, A. T.; King, H. *J. Chem. Soc.* 1947, 963-969. b) Bhat, J. I.; Clegg, W.; Maskill, H.; Elsegood, M. R. J.; Menneer, I, D.; Miatt, P. C. *J. Chem. Soc., Perkin Trans.* 2, 2000, 1435-1446). The N-hydroxy carbamate is then reacted with a suitable benzoyl chloride, e.g. 4-chlorobenzoyl chloride or benzoyl chloride, to give the desired nitrogen source reagent.

Scheme 1a

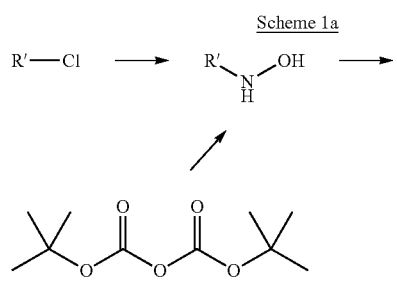

-continued

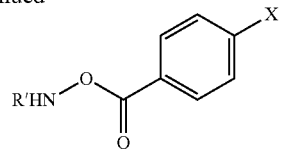

7: R' = EtO₂C, X = Cl
8: R' = BnO₂C, X = Cl
9: R' = Boc, X = Cl
10: R' = Fmoc, X = Cl
48: R' = PhO₂C, X = Cl
53: R' = BnO₂C, X = H The phenyl group shown in Scheme 1a may be unsubstituted (e.g. compound 53) or substituted with a chlorine group (e.g. compounds 7, 8, 9, 10 and 48), but it will be clear to those skilled in the art that other substituents are possible. For example, the phenyl group can be substituted with one or more substituents selected from halogen (e.g. chlorine, bromine fluorine, iodine), an alkoxy group, an alkyl group, a dialkylamino group, a trialkylammonium group, a nitro group, a carboxy group, a carboxy alkyl ester group, an alkylamide group, —SO₃H, —PO₃H or —COOH. It will be clear to the person skilled in the art that such compounds can be prepared by methods analogous to those described for compounds 7, 8, 9, 10, 48 or 53, or by published methods such as those described in Donohoe, T. J., Bataille, C. J. R, Gattrell, W., Kloesges, J. and Rossignol, E., *Org. Lett.*, 2007, 9, 1725-1728.

Advantageously, the N-oxycarbamate nitrogen source reagents of the invention can be prepared prior to carrying out the aminohydroxylation reaction, and stored for later use in the reaction. The nitrogen source reagents are stable and easily stored, so they are particularly suited for use in the process of the invention.

The N-acyloxycarbamate reagents are stable, crystalline solids and easily stored, so they are particularly suited for use in the process of the invention. For example, DSC (differential scanning calorimetric) studies show that the N-acyloxycarbamates compounds 7, 8, 10, 48 and 53 are stable past their melting points up until at least 160° C. and have slow decomposition above this point. They are therefore advantageous for use on a large scale and could be safely shipped.

Four criteria that can assist in assessing whether an organic compound will be stable under ordinary conditions of shipping and use are:

(a) crystalline with a narrow melting temperature range (this assists to quench any sharp temperature rise);
(b) a window of >80° C. between the melting point and the onset of any exothermic thermal decomposition;
(c) gradual rather than rapid onset of any exothermic thermal decomposition; and
(d) an exothermic decomposition energy of less than 500 J/g and the onset of exothermic decomposition is below 500° C., since such a compound is unlikely to have explosive properties (Summary User Guide to the HSNO Thresholds and Classifications of Hazardous Substances, ER-UG-04-1 6-01, New Zealand Environmental Risk Management Authority June 2001).

All these features can be evaluated from DSC measurements (see, e.g., M. Malow and K. D. Wehrstedt, *J. Hazardous Materials*, A120 (2005) 21-24), such as those shown for representative N-oxycarbamate reagents of the invention in FIGS. 3-11.

Compounds 7, 8, and 48 meet all four criteria, including exothermic decomposition energies of 86, 115, 285, and 82 J/g, respectively.

Compounds 10 and 53 meet criteria (a), (c) and (d), including exothermic decomposition energies of 267 and 283 J/g, and relatively high melting points (156 and 112° C.) but with only 36 and 45° C. differences, respectively between melting point and the onset of exothermic thermal decomposition.

Compound 9 meets criteria (a), (b) and (d), including an exothermic decomposition energy of 418 J/g, although the onset of exothermic thermal decomposition (at 167° C.) is more rapid than that of the above compounds.

Compound 57 meets criteria (a) and (d), including an exothermic decomposition energy of 459 J/g, although the onset of exothermic thermal decomposition occurs shortly after its melting point (at 150° C.).

It will be appreciated that this methodology can be used to evaluate other N-oxycarbamate reagents of the invention for stability under ordinary conditions of shipping and use. It will be appreciated that the above examples are not limiting.

Compounds of formulae (I)-(XIV) are described herein as "compounds of the invention". A compound of the invention includes a compound in any form, e.g. in free form or in the form of a salt or a solvate.

(b) N-Alkyloxycarbonyloxycarbamate and N-Aralkoxycarbonyloxycarbamate Compounds of the Invention The N-alkyloxycarbonyloxycarbamate and N-aralkoxycarbonyloxycarbamate nitrogen source reagents of the invention are synthesised as shown in Scheme 1b.

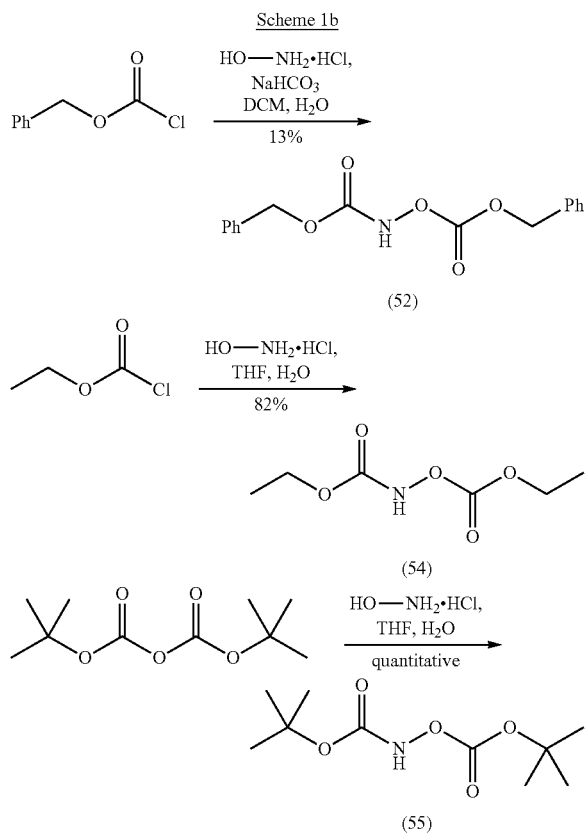

Treatment of hydroxylamine with two more equivalents of the appropriate starting material, e.g. ethyl chloroformate, methyl chloroformate, tert-butyl chloroformate, 2-trimethyl- silyl chloroformate (Teoc), 2,2,2-trichloroethylchloroformate (Troc), phenyl chloroformate, benzyl chloroformate, di-tert-butyldicarbonate or fluorehylmethoxycarbonyl chloride (FmocCl) with hydroxylamine gives an N-alkyloxycarbonyloxycarbamate or N-aralkoxycarbonyloxycarbamate.

The Process of the Invention

The invention also provides a process for the aminohydroxylation of alkenes using N-oxycarbamate reagents, e.g. N-acyloxycarbamate, N-alkyloxycarbonyloxycarbamate and N-aralkoxycarbonyloxycarbamate reagents, in particular an intermolecular aminohydroxylation reaction using N-oxycarbamate reagents and optionally carried out in the absence of added base.

The applicant has surprisingly found that N-oxycarbamate compounds are useful as nitrogen source reagents for the aminohydroxylation reaction, under reaction conditions where there is no requirement for added base. Advantageously, the process of the invention therefore provides greater flexibility in protecting group strategy as base-sensitive protecting groups such as Fmoc are very well tolerated. The process of the invention is reproducible and high-yielding. Certain nitrogen source reagents of the invention, e.g. N-acyloxycarbamate nitrogen source reagents, are stable crystalline materials with extended stability at high temperatures, and can be used in a variety of aminohydroxylation applications. The N-alkoxycarbonyloxycarbamate and N-aralkoxycarbonyloxycarbamate nitrogen source reagents of the invention are advantageous in that they form only volatile by-products. The process and reagents therefore provide facile routes to preparing biologically active compounds which contain the vicinal amino alcohol moiety.

In accordance with the process of the invention, an N-oxycarbamate nitrogen source reagent is reacted with ah alkene, in the presence of a suitable osmium catalyst, e.g. osmium tetroxide, potassium osmate(VI) dihydrate, osmium(III) trichloride, or immobilized osmium catalysts such as Os EnCat™40 Catalyst (Reaxa Limited, Blackley, Manchester, UK) and optionally in the absence of added base. It will be appreciated by those skilled in the art that the reaction of the alkene and the N-oxycarbamate compound is an intermolecular aminohydroxylation reaction.

The reaction of the alkene and the N-oxycarbamate compound can be carried out in any suitable organic solvent containing water, e.g. acetonitrile/water, isopropanol/water, or t-butanol/water.

Those skilled in the art will appreciate that a variety of osmium catalysts can be used in the process of the invention. Possible catalysts include osmium tetroxide, potassium osmate(VI) dihydrate, osmium(III) trichloride and immobilized osmium catalysts such as as Os EnCat™40 Catalyst (Reaxa Limited, Blackley, Manchester, UK) and the polymer/resin bound osmium tetroxide sources such as those available commercially (e.g. from Sigma-Aldrich®) and those described in Cheon Hee Jo, Sien-Ho Han, Jung Woon Yang, Eun Joo Roh, Ueon-Sang Shin and Choong Eui Song; *Chem. Commun.*, 2003, 1312-1313 and references therein, or an osmium(IV) catalyst (e.g. Os(IV) bisglycolate, see Cheon Hee Jo, Sien-Ho Han, Jung Woon Yang, Eun Joo Roh, Ueon-Sang Shin and Choong Eui Song; *Chem. Commun.*, 2003, 1312-1313 and references therein). Other osmium sources that are precursors to an Os(VIII) species can be used to generate an Os(VIII) catalyst species in situ. The osmium catalyst is present in catalytic amounts in the solvent. The preferred catalyst loading is in the range of about 0.1 mol % to about 20 mol %. In some examples of the process, good yields are obtained with low catalyst loading (about 4 mol %). If an Os(VIII) catalyst is used as a catalyst, it is preferable to use low catalyst loadings. On the other hand, the use of an Os(VI) catalyst is preferable if it is desired to minimise the production of diol by-product.

The reaction of the alkene and the N-oxycarbamate compound is preferably carried out at room temperature (about 20° C.). However, the reaction can be carried out at temperatures of about −10° C. to about 90° C., typically about 10° C. to about 30° C.

Those skilled in the art will understand that the process of the invention has a wide applicability to a range of alkenes. Some examples of alkenes that can be used in the process are described herein but the skilled person will understand that these are given by way of example, and the process can be applied to many different alkenes. Preferably the alkene is one which does not carry a substituent that has the ability to coordinate to osmium.

The applicant has therefore found that the process of the invention can be applied to a variety of intermolecular aminohydroxylation reactions, some of which are described herein by way of example.

The nitrogen source reagent 7 can be used in an intermolecular aminohydroxylation reaction to synthesise compound 2, which is an intermediate in the synthesis of allosamidin (Scheme 2). The N-chloro-N-metallo-carbamate reaction conditions utilised by Blattner et al. (Blattner, R.; Furneaux, R. H.; Kemmitt, T.; Tyler, P. C.; Ferrier, R. J.; Tiden, A-K. *J. Chem. Soc., Perkin Trans.* 1, 1994, 3411-3421), as well as the following standard Sharpless aminohydroxylation conditions: $EtO_2CNH_2$, $OsO_4$, DABCO, i-PrOH, $H_2O$, t-BuOCl, NaOH, give variable results when the aminohydroxylation reaction is carried out on alkene 1. Total product (2 plus 3) yields using any of these conditions are in the range 10-60%, with unpredictable variability in yield.

Scheme 2

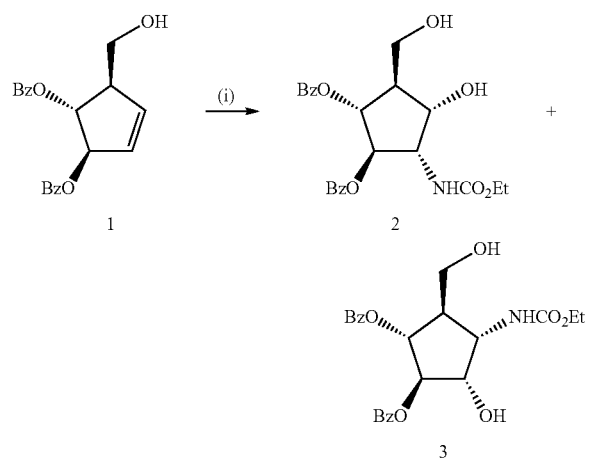

(i) 7, $OsO_4$, $H_2O$, t-BuOH

However, the reaction conditions shown in (i), using nitrogen source reagent 7 of the present invention, provide the products in good yield. Thus, treatment of precursor 1 with reagent 7 in the presence of 4 mol % of osmium tetroxide in a reaction medium which contains no added base yields the two regioisomeric products 2 and 3 in about 1:1 ratio and with a total yield of 84%. The reaction is reproducible and responds well to scale-up.

Treatment of isopropyl cinnamate with the appropriate reagent 7, 8, 9 or 10 in the presence of 4 mol % osmium tetroxide yields the corresponding racemic product 11a, 12a, 13a, 14a, 11b, 12b, 13b, 14b (Table 1). A preferred solvent for the reaction is a mixture (e.g. an 8:1 mixture v/v) of acetonitrile and water.

TABLE 1

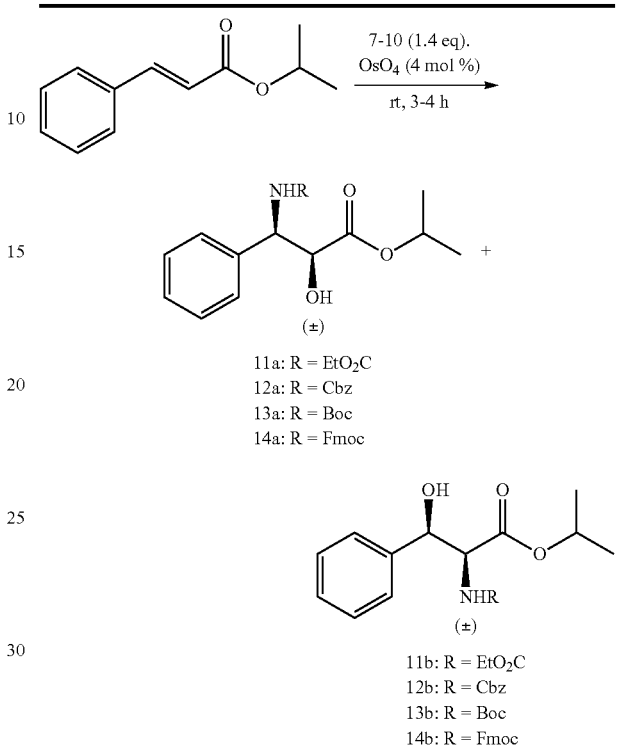

11a: R = $EtO_2C$
12a: R = Cbz
13a: R = Boc
14a: R = Fmoc

11b: R = $EtO_2C$
12b: R = Cbz
13b: R = Boc
14b: R = Fmoc

| Nitrogen source reagent (R =) | Solvent | Yield[a] [%] | Product ratio[b] (a:b) |
|---|---|---|---|
| 7 ($EtO_2C$) | tBuOH:water: 3:1 | 96 | 1:1.4 |
| 8 (Cbz) | tBuOH:water: 6:1 | 95 | 1:1 |
| 8 (Cbz) | MeCN:water: 8:1 | 96 | 1:1.3 |
| 9 (Boc) | MeCN:water: 8:1 | 93 | 1:1 |
| 10 (Fmoc) | MeCN:water: 8:1 | 96 | 1:1.9 |

[a]Isolated yield after chromatography;
[b]Measured by HPLC

Furthermore, treatment of various alkenes with nitrogen source reagent 8 in the presence of 4 mol % osmium tetroxide yields racemic products 15a, 15b, 16a, 16a, ±17, ±18, ±19, ±20. (Table 2). Reactions involving the two simple unsymmetrical alkenes (the first two entries in Table 2) show high regioselectivity with product ratios (a:b) of 9.5:1 and 5.5:1, respectively. In both cases, the carbamate moiety is established preferentially at the least sterically-hindered end of the alkene. The extent of the regioselectivity obtained is as good as or better than that which can be achieved under previously reported aminohydroxylation reaction conditions and is considered to be due to the absence of added base. Nesterenko et al. have recently demonstrated, using pH control in the standard conditions for Sharpless aminohydroxylation, that the formation of the major product 15a is optimal at a pH in the range of 7.5-8.5 (Nesterenko, V.; Byers, J. T.; Hergenrother, P. J.; *Org. Lett.* 2003, 281-284). However, the Nesterenko process involves the in situ preparation of a nitrogen source reagent, requiring the addition of a strong base, sodium hydroxide, such that the pH is greater than 12.5. The Nesterenko process is therefore not desirable for use with nitrogen source reagents that are base-sensitive. After in situ preparation of the nitrogen source reagent, the pH of the reaction mixture then has to be adjusted using a buffer so that it is in the range of 7.5-8.5. In contrast, the process of the present invention does not require the addition of any base. There is, therefore, no additional step of adjusting the pH. Further, the nitrogen source reagent can be prepared and stored, rather than being prepared in situ and the process of the invention can be used with nitrogen source reagents that are base sensitive, such as reagent 10. Furthermore, using the process of the present invention, it is possible to achieve a 9.5:1 ratio for products 15a and 15b.

TABLE 2

| Alkene | Products | Time [h] | Total yield [%][a] | Product ratio[b] a:b |
|---|---|---|---|---|
| 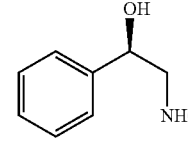 | (±)-15a + (±)-15b | 3 | 96 | 9.5:1 |
| 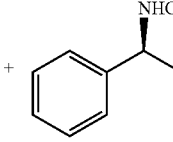 | (±)-16a + (±)-16b | 15 | 91 | 5.5:1 |
|  | (±)-17 | 3 | 96 | — |
| 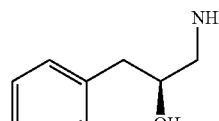 | (±)-18 | 3 | 99 | — |
| 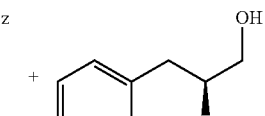 | (±)-19 | 15 | 93 | — |
| 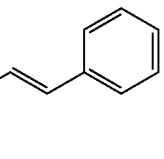 | (±)-20 | 3 | 96 | — |

[a] Isolated yield after chromatography;
[b] determined by HPLC.

Optionally, chiral ligands can be employed in the process of the invention, so that the process involves an asymmetric aminohydroxylation reaction. It will be appreciated by those skilled in the art that the chiral ligands can regioselectively and enantiomerically direct the reaction. The presence of the chiral ligand is therefore useful to induce asymmetry into the product. Suitable chiral ligands include chiral phthalazine (PHAL) and anthraquinone (AQN) ligands, e.g. (DHQ)$_2$PHAL, (DHQD)$_2$PHAL and (DHQ)$_2$AQN. Other suitable chiral ligands include cinchona alkaloids immobilised onto polymer supports (see, for example, C. E. Song, C. R. Oh, S. W. Lee, S.-g. Lee, L. Canali and D. C. Sherrington, *Chem. Commun.*, 1998, 2435 and E. Nandanan, P. Phukan, G. C. G. Pais and A. Sudalai, *Indian J. Chem.*, 1999, 38B, 287).

The chiral ligand is present in the reaction of the alkene with the N-acyloxycarbamate nitrogen source, in the presence of osmium catalyst. The preferred concentration range for the chiral ligand is about 1 to 1.5 times the amount (mol %) of osmium catalyst used in the process, e.g. about 1.1 to 1.3 times the amount (mol %) of osmium catalyst used.

Table 3 shows the reaction of nitrogen source reagent 8 with isopropyl cinnamate in the presence of chiral ligands (DHQ)$_2$PHAL, (DHQD)$_2$PHAL and (DHQ)$_2$AQN. Treatment of isopropyl cinnamate with nitrogen source reagent 8 in the presence of 4 mol % osmium tetroxide and the chiral ligand results in excellent yields and, for the (DHQ)$_2$PHAL and (DHQD)$_2$PHAL ligands, further improved regioselectivity and enantiomeric purities of 97%.

The absolute configuration of the products (+)-12a and (−)-12a is confirmed by converting (+)-12a into the corresponding oxazolidinone methyl ester derivative (−)-25 as shown in Scheme 3. X-ray crystal structure analysis of crystals of (−)-25 grown from ethyl acetate/petroleum ether confirms the (2R,3S) configuration.

Scheme 3

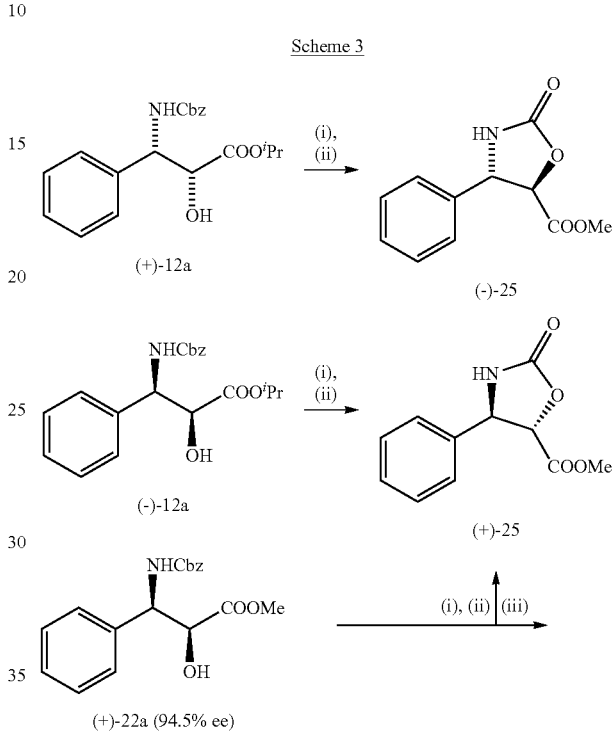

TABLE 3

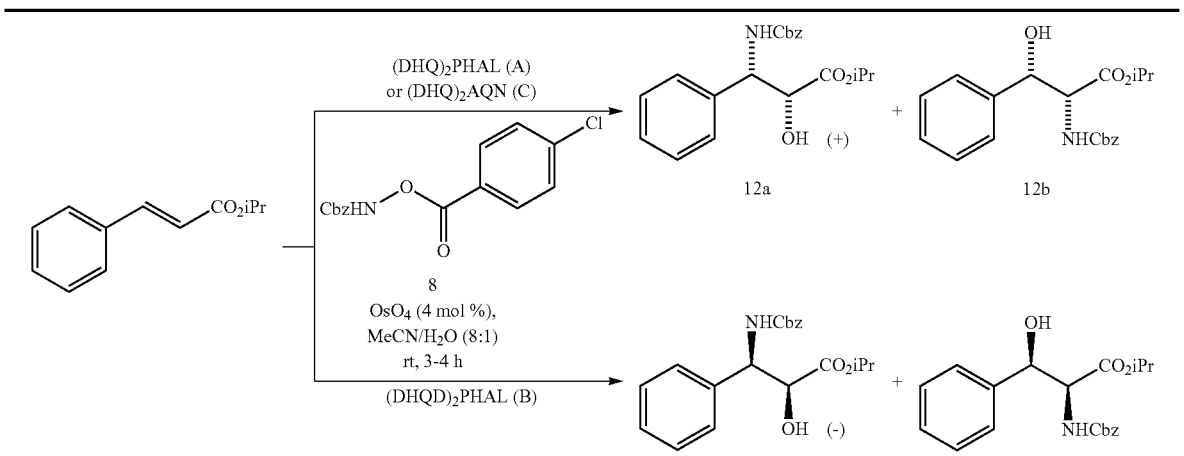

| Major product | Ligand | Yield[a] [%] | Optical purity [% ee][b] | [α]$_D$[c] | Regiomeric Ratio (a:b)[b] |
|---|---|---|---|---|---|
| (+)-12a | A | 84-96 | 97 | +15.1 | 12.7:1 |
| (−)-12a | B | 96 | 97 | −14.7 | 13.4:1 |
| (+)-12b | C | 90 | 71 | — | 1:1.6 |

[a]Combined isolated yield;
[b]determined by chiral phase HPLC;
[c]Major product at quoted ee.

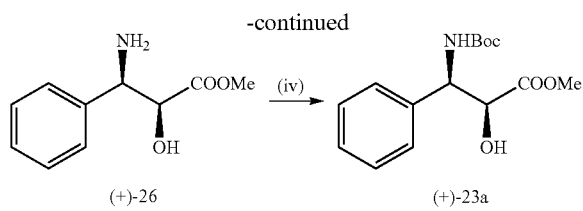

(i) LiOH, MeOH, H₂O, rt, 4 h (ii) CH₂N₂, THF, (−)-25: 50%, (+)-25: 55% (from (−)-12a), (+)-25: 19% (from (+)-22a) (iii) H₂, Pd/C, MeOH (iv) Boc₂O, MeOH, (+)-23a: 70% (over two steps).

Conversion of (−)-12a to the oxazolidinone methyl ester derivative (+)-25, using analogous reaction conditions (Scheme 3) confirms that (+)-25 has the opposite optical rotation to (−)-25.

Table 4 shows the reaction of nitrogen source reagents 7, 8, 9 and 10 with methyl-trans-cinnamate in the presence of chiral ligands (DHQ)₂PHAL and (DHQD)₂PHAL. Treatment of methyl-trans-cinnamate with the nitrogen source reagent in the presence of 4 mol % osmium tetroxide and the chiral ligand provides the products in good yields and with enantiomeric purities of 94-97%.

Similarly, (+)-26 and its Boc-protected analogue (+)-23a are prepared as shown in Scheme 3. In both cases the analytical data correspond to those reported in the literature.

X-ray crystal structure analysis of crystals of (−)-22a grown from ethyl acetate/petroleum ether confirms the structural assignment of this compound.

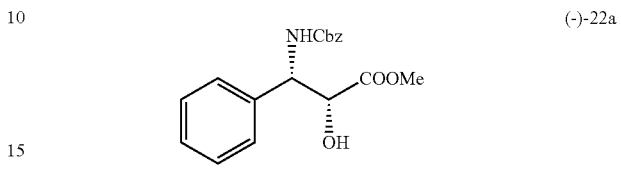

(−)-22a

X-ray crystal structure analysis of crystals of (−)-23a, as well as a comparison with published analytical data for this compound, confirm the structural assignment of the compound.

TABLE 4

| Major product | Reagent (R =) | Ligand | Yield[a] [%] | Optical purity [% ee][b] | $[\alpha]_D$ | Regiomeric Ratio (a:b)[b] |
|---|---|---|---|---|---|---|
| 21a | EtO₂C | A | 81 | 96 | +4.3 | 13:1 |
|  |  | B | 68 | 96 | −4.9 | 15:1 |
| 22a | Cbz | A | 59 | 96 | −1.3 | 5.9:1 |
|  |  | B | 59 | 97 | +1.1 | 6.8:1 |
| 23a | Boc | A | 43[c] | 95 | −6.7 | 6.1:1 |
|  |  | B | 46[c] | 96 | +6.6 | 4.9:1 |
| 24a | Fmoc | A | 86[d] | 94 | +8.0 | 6.6:1 |
|  |  | B | 94[d] | 96 | −8.3 | 5.6:1 |

[a]Isolated yield of major product;
[b]determined by chiral phase HPLC;
[c]lower yield due to enhanced yield (isolated) of diol;
[d]combined yield of mixture;

Again, conversion of (+)-22a to the corresponding oxazolidinone methyl ester derivative (−)-25, analogous to the procedure shown in Scheme 3, and then comparison of the optical rotation of this new sample of (−)-25 with that described above, support the structural assignment. Chiral-phase HPLC analysis, using co-elution experiments, also confirms the structural assignment (retention time of 23.8 min for both the new sample of (−)-25 and the sample described above).

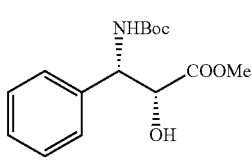

(−)-23a

The alternative osmium(VI) and osmium(III) reagents, potassium osmate and osmium trichloride, can be used in the above reactions with methyl cinnamate. Thus, reaction of Boc reagent 9, potassium osmate (4 mol %) and (DHQ)₂PHAL provides compounds (−)-23a (94% ee) and 23b in a combined yield of 49%, along with diol by-product (37%). The ratio a:b:diol is determined to be 5.61:1:3.79 by HPLC. Further, reaction of the ethyl reagent 7 and osmium(III) trichloride (4 mol %) in the absence of a chiral ligand provides compounds (±)-21a and (±)-21b in quantitative combined yield and a ratio (a:b) of 1:1.16 (determined by HPLC).

Table 5 shows the reaction of nitrogen source reagents 8 and 10 with diethyl allylphosphonate in the presence of chiral ligands (DHQ)₂PHAL and (DHQD)₂PHAL, and also the reaction of nitrogen source reagent 10 with diethyl allylphosphonate [Dappen, M. S.; Pelliciari, R.; Natalini, B.; Monahan, J. B.; Chiorri, C.; Cordi, A. A.; *J. Med. Chem.* 1991, 34, 161-168] in the absence of chiral ligands (the achiral reaction). Treatment of diethyl allylphosphonate with the nitrogen source reagent in the presence of 4 mol % osmium tetroxide and, optionally, the chiral ligand provides the products in good yields. Enantiomeric purities of 15% and 23% are obtained. It is surprising that good yields are obtained, as well as some enantioselectivity, because it has previously been reported that allylic phosphonate esters fail to undergo reaction, using various N-chloro-N-sodioamides in the asymmetric aminohydroxylation reaction, even upon prolonged heating. (Thomas, A. A.; Sharpless K. B.; *J. Org. Chem.* 1999, 64, 8379-8385). Thus, the process of the present invention can advantageously provide a route to aminohydroxylation of allyl phosphonates, which has previously not been possible.

TABLE 5

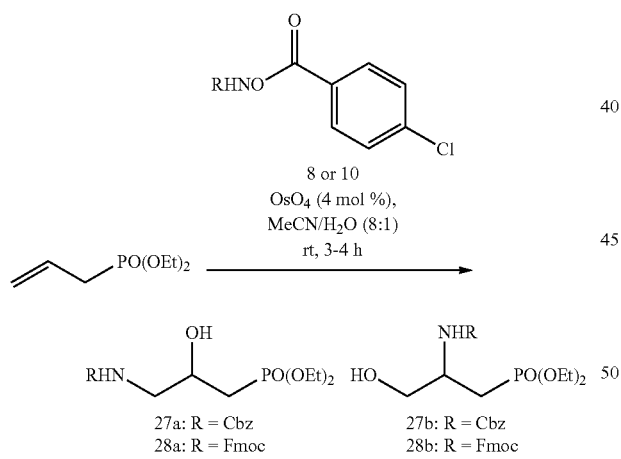

| Major product | Reagent (R =) | Ligand[a] | Yield[b] [%] | Optical purity [% ee][c] | Regioisomeric Ratio (a:b) |
|---|---|---|---|---|---|
| 27a | Cbz | A | 55 | 15 | 6.1:1 |
| 27a | Cbz | B | 59 | 23 | 8.9:1 |
| 28a | Fmoc | — | 80 | — | 10.1:1 |

[a]Ligand A = (DHQ)₂PHAL, Ligand B = (DHQD)₂PHAL;
[b]Overall yield;
[c]determined by chiral phase HPLC.

The Fmoc reagent 10 can be reacted with cyclohexenone to give the cis-3-amino-2-hydroxy-cyclohexenone derivative (±)-29 in 70% isolated yield (Scheme 4).

Scheme 4

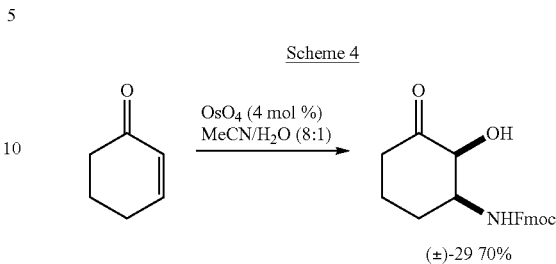

The ethyl and benzyl nitrogen source reagents 7 and 8 can furthermore be reacted with the chiral alkenes 30 [Qiu, X.-L.; Qing, F.-L.; *J. Org. Chem.* 2005, 70, 3826-3837], 35 [Herdeis, C.; Hubmann, H. P.; Lotter, H.; *Tetrahedron: Asymm.* 1994, 5, 119-128], 37 [Herdeis, C.; Hubmann, H. P.; Lotter, H.; *Tetrahedron: Asymm.* 1994, 5, 119-128], 40 [Oba, M.; Miyakawa, A.; Nishiyama, K.; *J. Org. Chem.* 1999, 64, 9275-9278] and 42 [Oba, M.; Miyakawa, A.; Nishiyama, K.; *J. Org. Chem.* 1999, 64, 9275-9278] as shown in Schemes 5-11. These reactions products reveal that high facial selectivity is achieved, and that regioselectivity is modest with the dihydropyrrole 30 and high with the lactams 35, 37, 40 and 42. In all but one case the yields are good (64-91%); the reason for the exception (the reaction in Scheme 9) is that this reaction is not taken to completion. The regioselectivity can be manipulated by the selection of the nitrogen source reagent, as can be seen by comparing modest regioselectivity obtained with benzyl reagent 8 in Scheme 10, with the very high regioselectivity obtained with the ethyl reagent 7 in Scheme 9 and 11.

Scheme 5

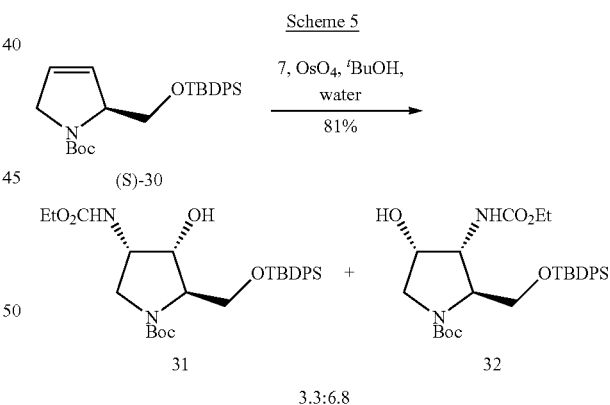

3.3:6.8

Scheme 6

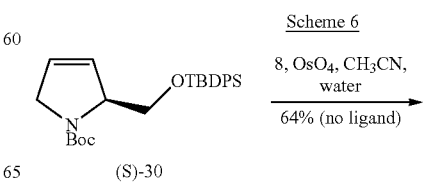

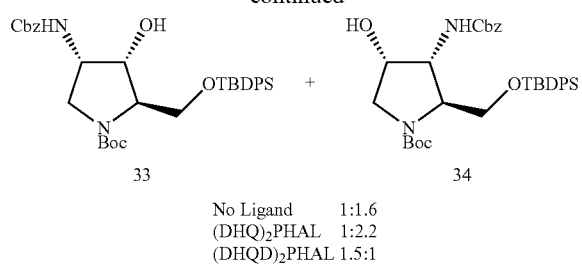
33
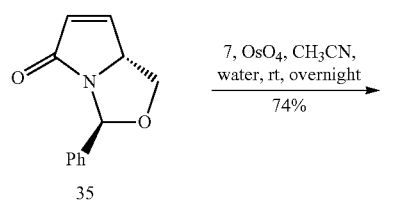
| | |
|---|---|
| No Ligand | 1:1.6 |
| (DHQ)₂PHAL | 1:2.2 |
| (DHQD)₂PHAL | 1.5:1 |
Scheme 7
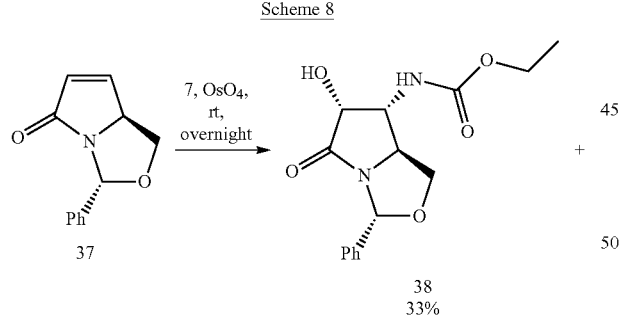
36
9:1
Scheme 8
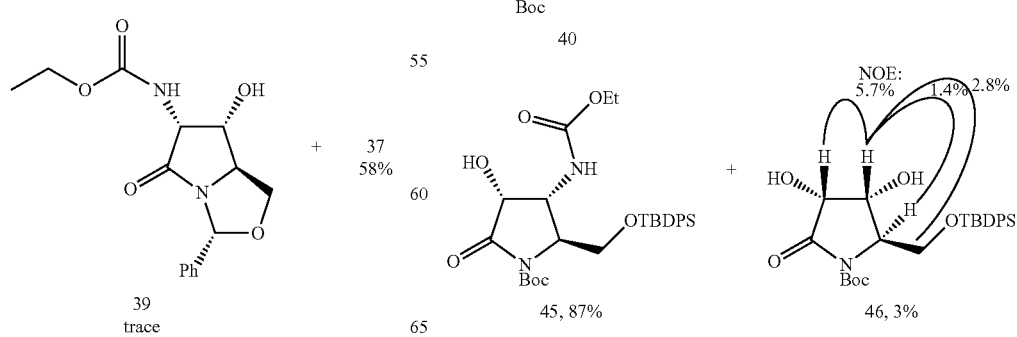
Scheme 9
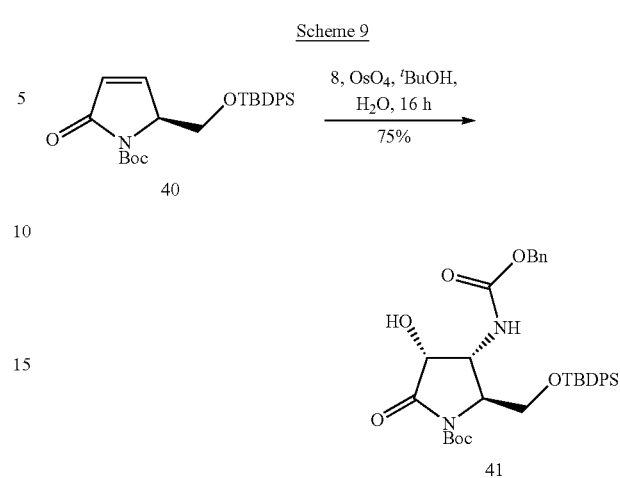
Scheme 10
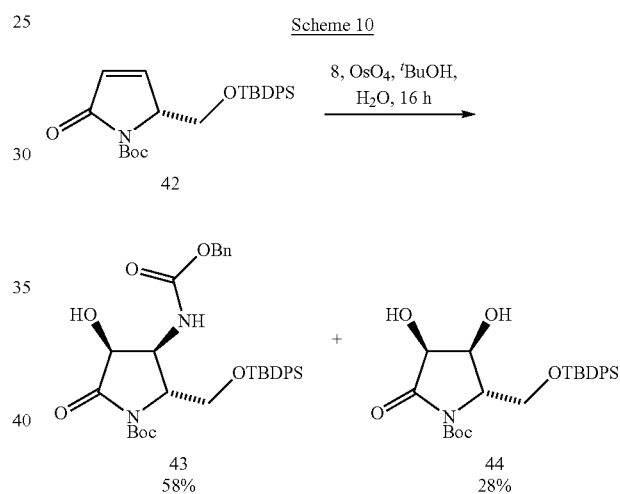
Scheme 11

The synthesis and an example of the use of the phenyl reagent 48 are shown in Scheme 12, in which 48 is the nitrogen source reagent that provides the regioisomeric, racemic amino-alcohols 49 and 50 in 93% overall yield in a ratio of 1:1.07 respectively (by HPLC) from methyl cinnamate.

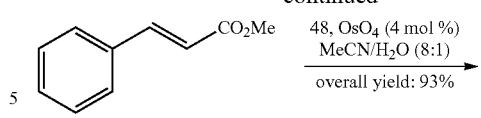

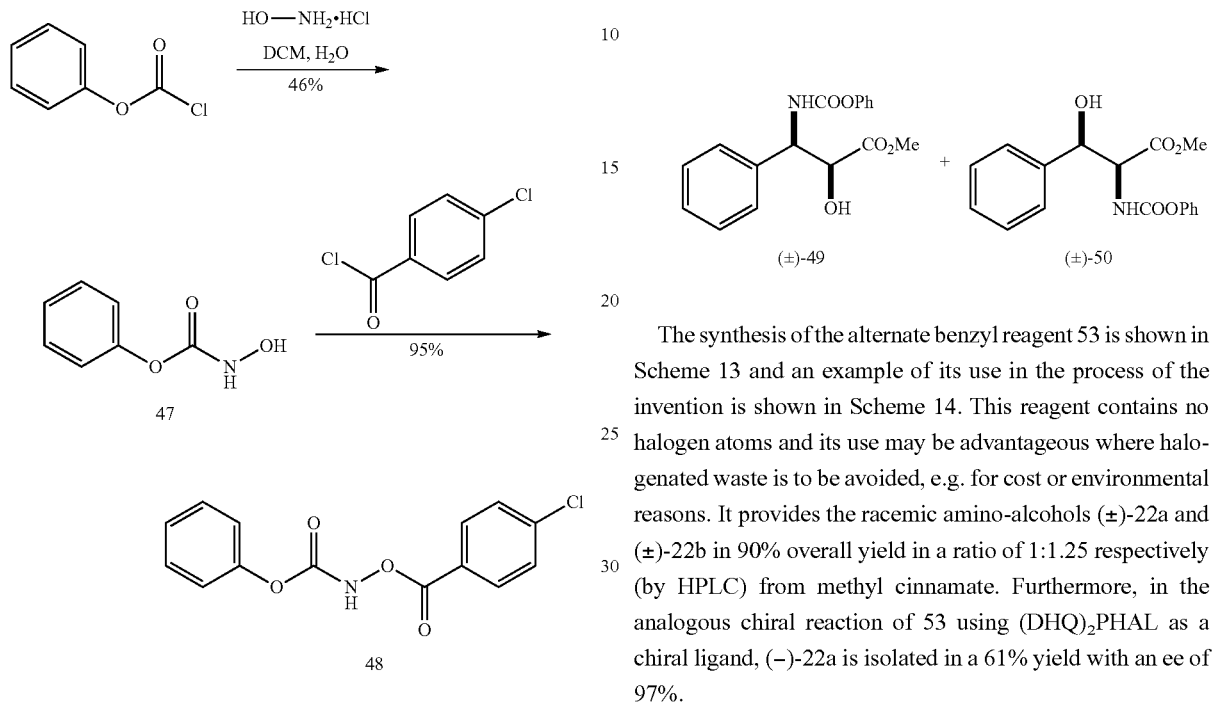

The synthesis of the alternate benzyl reagent 53 is shown in Scheme 13 and an example of its use in the process of the invention is shown in Scheme 14. This reagent contains no halogen atoms and its use may be advantageous where halogenated waste is to be avoided, e.g. for cost or environmental reasons. It provides the racemic amino-alcohols (±)-22a and (±)-22b in 90% overall yield in a ratio of 1:1.25 respectively (by HPLC) from methyl cinnamate. Furthermore, in the analogous chiral reaction of 53 using (DHQ)$_2$PHAL as a chiral ligand, (−)-22a is isolated in a 61% yield with an ee of 97%.

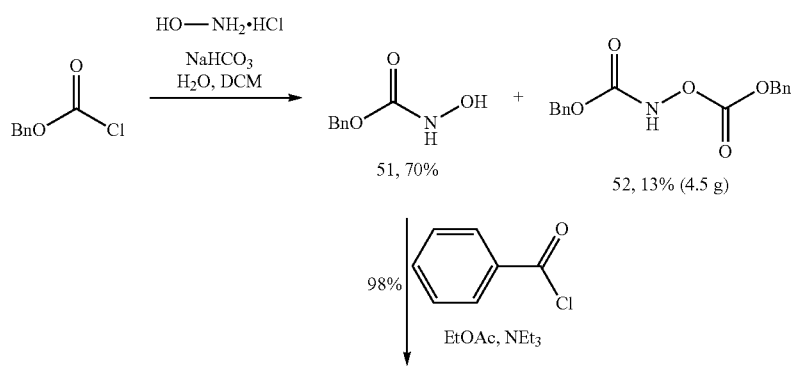

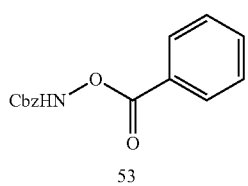

Scheme 14

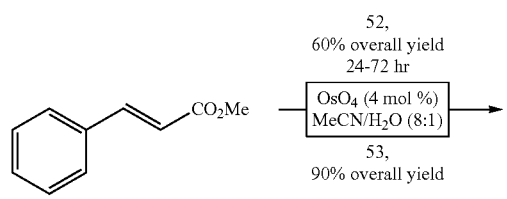

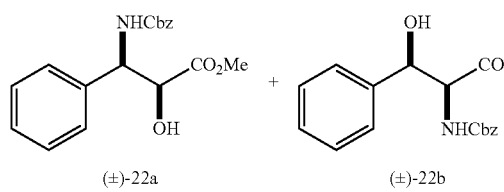

Another synthesis of benzyl benzyloxycarbonyloxycarbamate (52) is shown in Scheme 13 above. This reagent can be used in the synthesis of the racemic amino-alcohols (±)-22a and (±)-22b in 60% overall yield in a ratio of 1:1.23 respectively (by HPLC) from methyl cinnamate, as shown in Scheme 14 above. An advantage of this reagent is that the reaction by-products (benzyl alcohol and carbon dioxide) are volatile.

The reagents ethyl ethoxycarbonyloxycarbamate (54) and tert-butyl tert-butylcarbonyloxycarbamate (55) can be used in the syntheses of the regioisomeric, racemic amino-alcohols (±)-21a and (±)-21b in 82% overall yield (in a ratio of 1:1.23 as determined by HPLC), and (±)-23a and (±)-23b in 61% overall yield (in a ratio of 1:1.64 as determined by HPLC), respectively, from methyl cinnamate is shown in Scheme 15. An advantage of these reagents is that the reaction by-products (ethanol and tert-butanol, respectively, and carbon dioxide) are volatile.

The Fmoc reagent (57) can be used in the syntheses of the regioisomeric, racemic amino-alcohols (±)-24a and (±)-24b using either THF/water or acetone/water, as shown in Scheme 16.

Scheme 16

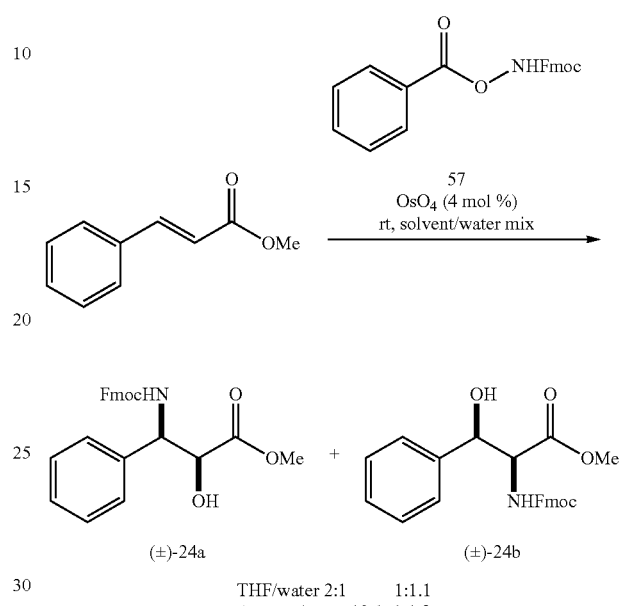

THF/water 2:1    1:1.1
Acetone/water 10:1    1:1.3

The Fmoc reagent (10) can be used in the syntheses of the regioisomeric, racemic amino-alcohols (±)-24a and (±)-24b, as shown in Scheme 17.

Scheme 17

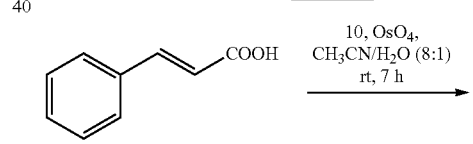

Scheme 15

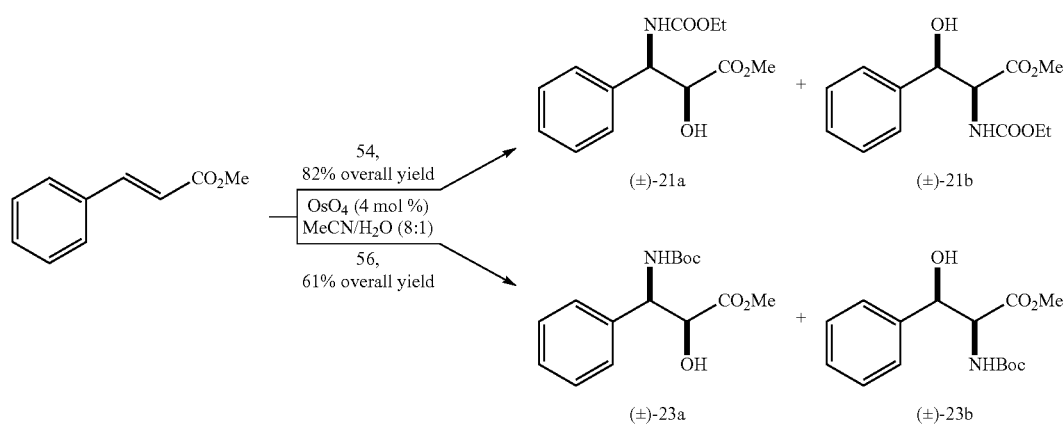

-continued

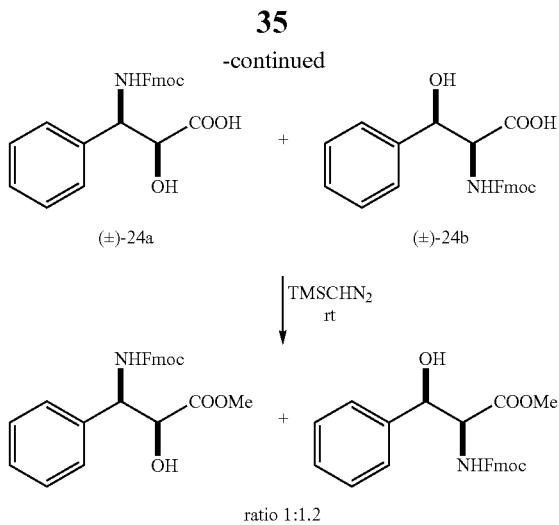

ratio 1:1.2

ABBREVIATIONS

Figure 1:
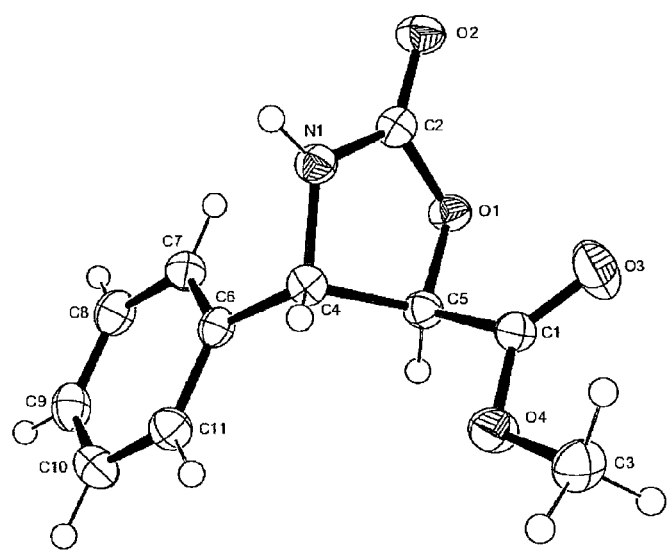
FIG. 1 shows the X-ray crystal structure of compound (−)-25 (ellipsoids at 30% probability).
Figure 2:
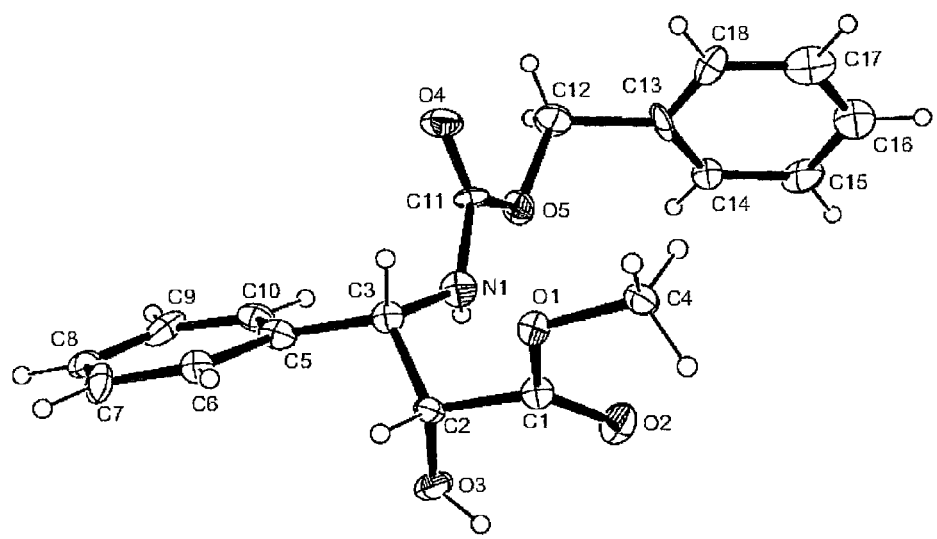
FIG. 2 shows the X-ray crystal structure of compound (−)-22a (ellipsoids at 30% probability).
Figure 3:
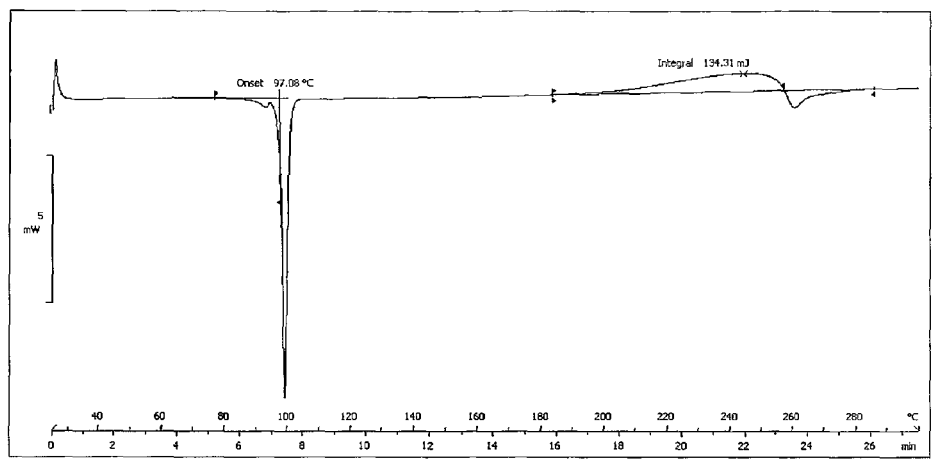
FIG. 3 shows the DSC curve for compound 8.
Figure 4:
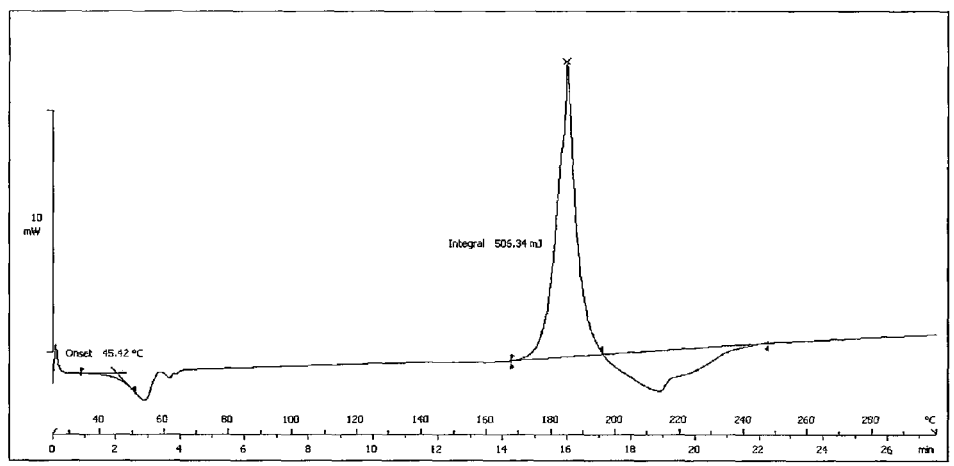
FIG. 4 shows the DSC curve for compound 9.
Figure 5:
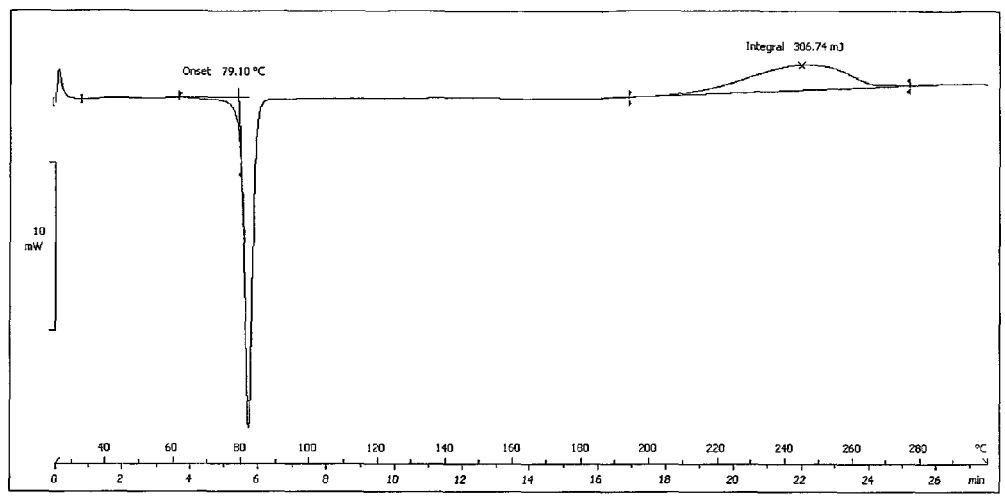
FIG. 5 shows the DSC curve for compound 7.
Figure 6:
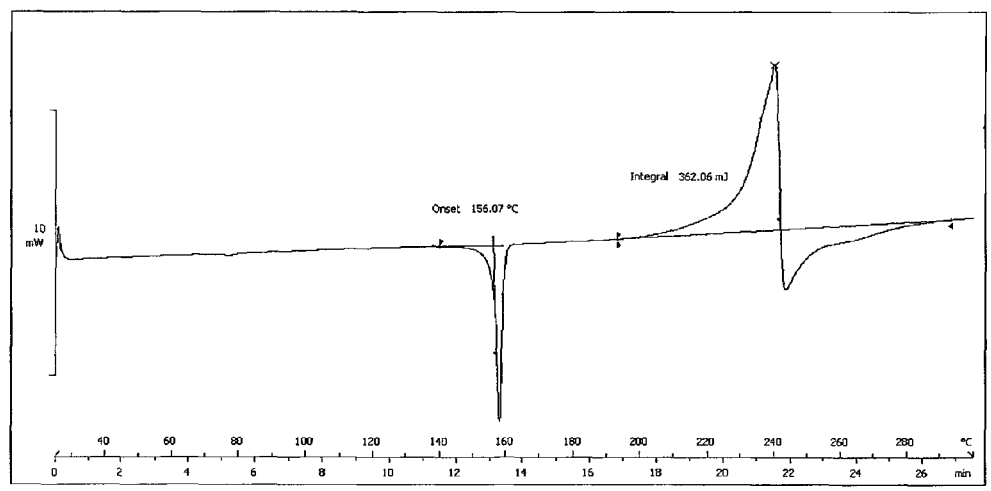
FIG. 6 shows the DSC curve for compound 10.
Figure 7:
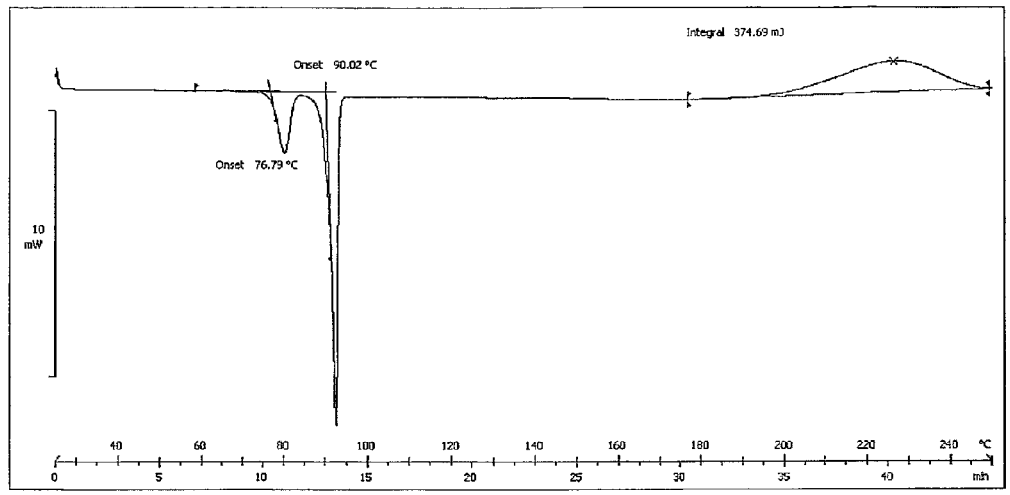
FIG. 7 shows the DSC curve for compound 48.
Figure 8:
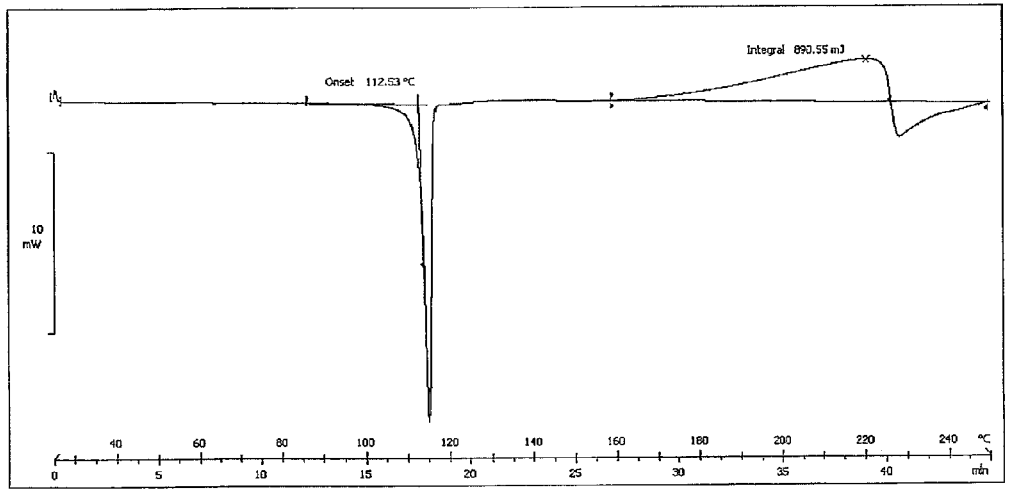
FIG. 8 shows the DSC curve for compound 53.
Figure 9:
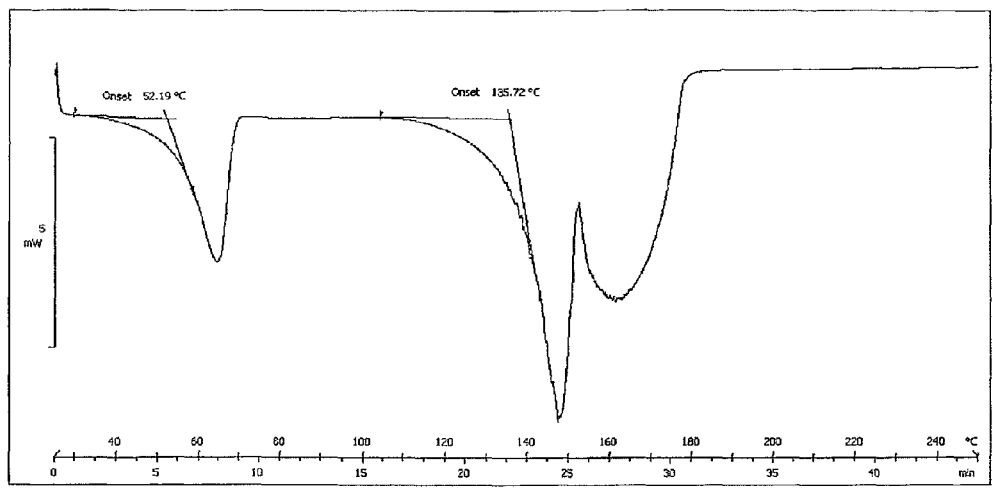
FIG. 9 shows the DSC curve for compound 55.
Figure 10:
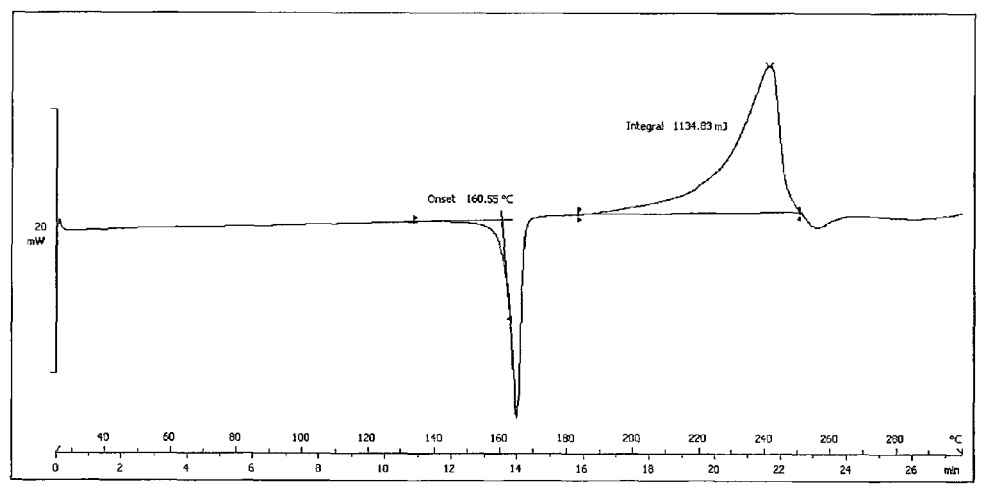
FIG. 10 shows the DSC curve for compound 56.
Figure 11:
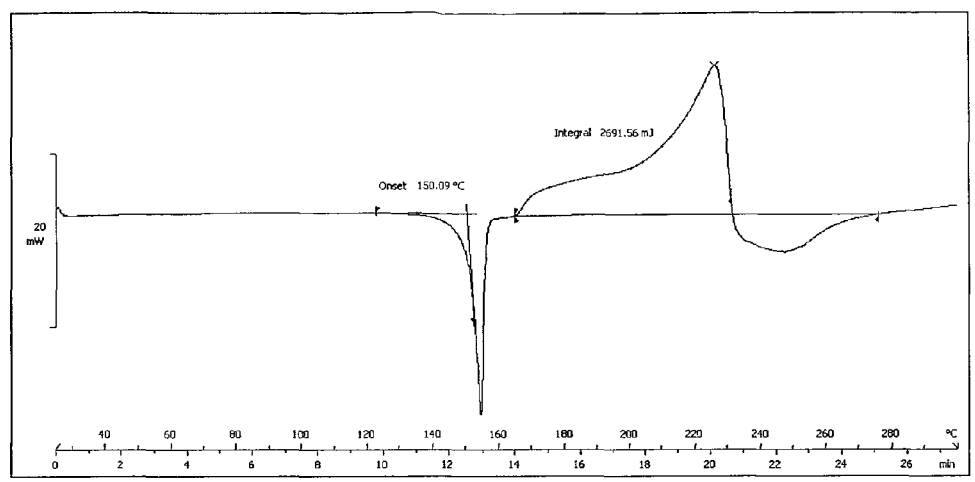
FIG. 11 shows the DSC curve for compound 57.

NMR nuclear magnetic resonance
FTIR Fourier transform infrared
HPLC high performance liquid chromatography
TLC thin layer chromatography
MS mass spectrometry
ESI electrospray ionisation
DSC differential scanning calorimetry
Boc tert-butoxycarbonyl
Cbz benzyloxycarbonyl
Fmoc 9-fluorenylmethoxycarbonyl
Teoc 2-trimethylsilylethoxycarbonyl
Troc 2,2,2-trichloroethoxycarbonyl
DCM dichloromethane
$(DHQ)_2(PHAL)$ 1,4-bis(9-O-dihydroquininyl)-phthalazine
$(DHQD)_2(PHAL)$ 1,4-bis(9-O-dihydroquinidinyl)-phthalazine
$(DHQ)_2AQN$ hydroquinine anthraquinone-1,4-diyl diether

EXAMPLES

The following examples further illustrate the invention. It is to be appreciated that the invention is not limited to the examples.
General Procedures Melting points are obtained on a Stuart Melting Point (SMP3) apparatus and are uncorrected or on a Mettler Toledo DSC1 instrument at a heating rate of 10 Kmin$^{-1}$. Infrared spectra are recorded on a Perkin-Elmer Spectrum One FTIR spectrometer. $^1$H and $^{13}$C NMR-spectra are recorded on Avance (III)-500 or Avance-300 spectrometers. Electrospray ionization (ESI) mass spectrometry (MS) experiments are performed on a QT of Premier mass spectrometer (Micromass, UK) under normal conditions. Sodium formate solution is used as calibrant for HRMS measurements. Elemental microanalyses are performed at The Campbell Microanalytical Laboratory, Department of Chemistry at the University of Otago on a Carlo-Erba EA 1108 elemental analyzer.

All reactions are monitored by thin layer chromatography (TLC) using 0.2 μm silica gel (Merck Kieselgel 60 F$_{254}$) precoated plates, using UV light, ammonium molybdate or potassium permanganate to visualize. Davisil® silica gel (60, particle size 0.040-0.063 mm) is used to perform flash column chromatography. Solvents for reactions and chromatography are analytical grade and are used as supplied unless otherwise stated.

Chiral phase HPLC is performed on several columns as indicated below using an Agilent 110 (Quaternary pump) HPLC system with a diode array detector (200-400 nm). Injection volumes are typically 10 μL (1-2 mgmL$^{-1}$) and data are processed with Agilent Cerity System software.

General Procedure for Asymmetric Aminohydroxylation (AA) Reactions

Osmium tetroxide (8 mg, 32 μmol) is added to a solution (or suspension) of ligand [(DHQ)$_2$PHAL (A), (DHQD)$_2$PHAL) (B) or (DHQ)$_2$AQN (C)] (39 μmol) and 4-chlorobenzoyloxy carbamate reagent (7-10) (1.10 mmol) in acetonitrile (3.5 mL). This mixture is allowed to stir for 10 minutes before a solution of alkene (0.79 mmol) in acetonitrile (3.5 mL) is added followed immediately by the addition of water (0.85 mL). The reaction mixture is stirred at room temperature and monitored by TLC-analysis and deemed to be complete when alkene starting material has been completely consumed. When deemed to be complete (3-24 h) the reaction mixture is quenched by adding saturated aqueous K$_2$S$_2$O$_5$ solution (2 mL) followed by adding water (30-50 mL) and ethyl acetate (30-50 mL). The separated aqueous layer is extracted with ethyl acetate (2×30 mL) and the combined organic phases are washed with saturated aqueous NaHCO$_3$ solution (2×50 mL) and brine, dried over MgSO$_4$ and concentrated. The crude residue is purification by flash column chromatography on silica gel eluting with solvent mixtures outlined below. In all cases except with Fmoc reagent 10 the reactions are homogenous to begin with, with a white precipitate evolving within approximately 2 h in most cases.

Non-Chiral Reactions

For achiral reactions, unless indicated, an identical procedure is followed to that described above for the asymmetric aminohydroxylation reactions, except that the addition of chiral ligands is omitted.

Ethyl hydroxycarbamate (6).

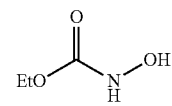

(Bhat, J. I.; Clegg, W.; Maskill H.; Elsegood, M. R. J.; Menneer, I. D.; Miatt, P. C. *J. Chem. Soc., Perkin Trans.* 2 2000, 1435-1446; Major, R. T.; Dürsch, F.; Hess, H.-J. *J. Org. Chem.* 1959, 24, 431-433.)

Ethyl chloroformate (13.4 ml, 140 mmol) is added slowly to a solution of hydroxylamine hydrochloride (10.0 g, 145 mmol) and sodium carbonate (22.4 g, 211 mmol) in water (66 mL) keeping the temperature below 30° C. After stirring at room temperature for 2 h, the reaction is quenched by the addition of conc. HCl until pH 1 then extracted with diethyl ether (2×100 mL), dried over MgSO$_4$ and the solvent is removed under reduced pressure to give 6 (5.40 g) as a colourless gum. Another 150 mL of diethyl ether are added to the aqueous portion and stirred vigorously for 1 day. The organic layer is separated, dried over MgSO$_4$ and concentrated to give and additional 2.50 g of 6. This procedure is repeated one more time to give an additional 2.2 g of the desired product 6. In total 10.1 g (69%) of 6 are isolated. $^1$H NMR (500 MHz, CHCl$_3$) δ 7.63 (br s, 2H), 4.19 (q, J=7.1 Hz, 2H), 1.26 (t, J=7.1 Hz, 3H); $^{13}$C NMR (125 MHz, CDCl$_3$) δ 159.6, 62.14, 14.25. The spectroscopic data are consistent with those reported in the literature.

Ethyl 4-chlorobenzoyloxycarbamate (7).

(Donohoe, T. J.; Bataille, C. J. R.; Gattrell, W.; Kloesges, J.; Rossignol, E. *Org. Lett.* 2007, 9, 1725-1728; Oesper, R.; Broker, W.; *J. Am. Chem. Soc* 1925, 47, 422-428.)

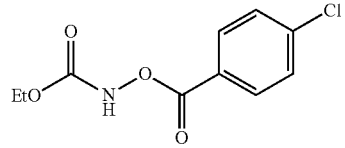

4-Chlorobenzoyl chloride (1.10 mL, 8.57 mmol) is added slowly to a solution of ethyl hydroxycarbamate 6 (1.00 g, 9.52 mmol) and triethylamine (1.19 mL, 8.57 mmol) in diethyl ether (30 mL) at 0° C. then stirred at room temperature for 30 min. The reaction is quenched with HCl (1 M; 10 mL) then water (100 mL) is added and extracted with diethyl ether (100 mL). The organic layer is washed with sat. NaHCO$_3$ (50 mL), water (50 mL), dried with MgSO$_4$ and concentrated. The residue is purified by flash column chromatography (silica gel, petroleum ether/ethyl acetate 9:1 then 8:2) to yield 7 (1.54 g) as an off-white solid. M.p. 79° C. (determined by differential scanning calorimetry, sharp onset); FTIR (neat, cm$^{-1}$) 3210, 3094, 2990, 1765, 1708, 1588, 1495, 1487, 1473, 1443, 1401, 1368, 1298, 1283, 1249, 1235, 1177, 1121, 1107, 1090, 1054, 1016, 996, 876, 852, 771, 747, 728, 681; $^1$H NMR (500 MHz, CDCl$_3$) δ 8.34 (s, 1H), 8.02 (dt, J=2.1, 8.7 Hz, 2H), 7.46 (dt, J=2.1, 8.7 Hz, 2H), 4.28 (q, J=7.1 Hz, 2H), 1.31 (t, J=7.1 Hz, 3H); $^{13}$C NMR (125 MHz, CDCl$_3$) δ 165.1, 156.6, 140.9, 131.3, 129.1, 125.2, 63.0, 14.3; HRMS (ES+) m/z calcd for C$_{10}$H$_{10}$ClNO$_4$ (M+Na)$^+$ 266.0191, found 266.0199.

Benzyl 4-chlorobenzoyloxycarbamate (8).

4-Chlorobenzoyl chloride (13.1 mL, 102 mmol) is added slowly to a solution of benzyl hydroxycarbamate (19.0 g, 114 mmol) and triethylamine (14.4 mL, 104 mmol) in diethyl ether (500 mL) at 0° C. then stirred at room temperature for 1 h. The reaction is

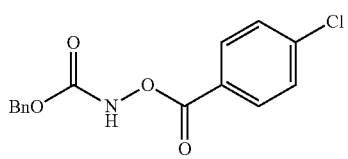

quenched with 1 M hydrochloric acid (100 mL) then the solution is washed with water (2×400 mL) then sat. NaHCO$_3$ (100 mL), dried over MgSO$_4$ and the solvent is removed under reduced pressure to give 8 (32.4 g, 93%) which is used without further purification. An analytical sample (5 g) is prepared by flash column chromatography (silica gel, petroleum ether/ethyl acetate 9:1 and 4:1). M.p. 97° C. (determined by differential scanning calorimetry, sharp onset); FTIR (neat, cm$^{-1}$) 3231, 2917, 1772, 1734, 1701, 1593, 1489, 1472, 1454, 1405, 1388, 1288, 1267, 1233, 1179, 1119, 1108, 1089, 1045, 1027, 1020, 1009, 975, 946, 911, 883, 848, 785, 772, 753, 730, 697, 682, 668, 655; $^1$H NMR (500 MHz, CHCl$_3$) δ 8.35 (s, 1H), 8.04-8.01 (m, 2H), 7.48-7.45 (m, 2H), 7.39-7.32 (m, 5H), 5.25 (s, 2H); $^{13}$C NMR (125 MHz, CHCl$_3$) δ 164.99, 156.35, 140.93, 134.98, 131.32, 129.15, 128.65, 128.32, 125.11, 68.50; HRMS (ES+) m/z calcd for C$_{15}$H$_{12}$NO$_4$$^{35}$Cl (M+Na)$^+$ 328.0353, found 328.0347.

tert-Butyl hydroxycarbamate.

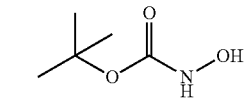

Bollans, L.; Bacsa, J.; Iggo, J. A.; Morris, G. S.; Stachulski, A. V.; *Org. Biomol. Chem.*, 2009, 7, 4531-4538.)

To a biphasic mixture of hydroxylamine hydrochloride (3.00 g, 43.2 mmol) in water (39 mL) and DCM (40 mL) at 0° C. is added NaHCO$_3$ (6.60 g, 79.0 mmol) in small portions. After 10 min di-tert-butyl dicarbonate (7.5 g, 34.4 mmol) is added. The mixture is allowed to stir at 0° C. until the water bath warmed to room temperature and then left overnight. The aqueous layer is separated and extracted with DCM (2×30 mL) before the combined extracts are washed with sat. NaHCO$_3$ solution (30 mL), water (30 mL) and brine (30 mL), dried over MgSO$_4$ and concentrated to yield the title compound (3.90 g, 85%) as a clear oil which is used without further purification. The spectroscopic data are consistent with those reported in the literature (Bollans, L.: Bacsa, J.; Iggo, J. A.; Morris, G. A.; Stachulski, A. V.; *Org. Biomol. Chem.*, 2009, 7, 4531-4538).

tert-Butyl hydroxycarbamate (larger scale)

(Bollans, L.; Bacsa, J.; Iggo, J. A.; Morris, G. A.; Stachulski, A. V.; *Org. Biomol. Chem.*, 2009, 7, 4031-4038.)

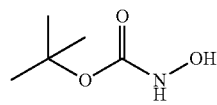

To a biphasic mixture of hydroxylamine hydrochloride (20.0 g, 0.29 mol) in water (257 mL) and DCM (264 mL) at 0° C. is added NaHCO$_3$ (43.6 g, 0.52 mol) in small portions. After 10 min di-tert-butyl dicarbonate (50.0 g, 0.23 mol) is added. The mixture is allowed to stir at 0° C. until the water bath warmed to room temperature and then left overnight. The aqueous layer is separated and extracted with DCM (2×200 mL) before the combined extracts are washed with sat. NaHCO$_3$ solution (200 mL), water (200 mL) and brine (200 mL), dried over MgSO$_4$ and concentrated to yield a crude product which was fractionated by flash column chromatography on silica gel (eluent: Dichloromethane and 20% ethyl acetate/dichloromethane) to give the title compound (18.9 g, 61%) as a colorless crystalline solid. The spectroscopic data are consistent with those reported in the literature (Bollans, L.; Bacsa, J.; Iggo, J. A.; Morris, G. A.; Stachulski, A. V.; *Org. Biomol. Chem.*, 2009, 7, 4531-4538).

tert-Butyl 4-chlorobenzoyloxycarbamate (9).

To a solution of tert-butyl hydroxycarbamate (3.90 g, 29.3 mmol) in DCM (50 mL) at 0° C., is added 4-chlorobenzoyl chloride (3.25 mL, 29.3 mmol) followed by the dropwise addition of triethylamine (4.12 mL, 29.3 mmol). The reaction is allowed to stir at room

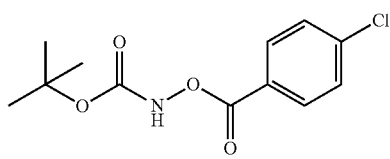

9 temperature for 1 h before hydrochloric acid (1 M, 20 mL) is added. The organic layer is separated and washed with sat. NaHCO$_3$ solution (2×30 mL), brine (30 mL) and dried over MgSO$_4$ before being concentrated. The residue is purified by flash column chromatography (silica gel, petroleum ether/ethyl acetate 19:1 then 93:7) to give 8 (3.00 g, 38%) as a white solid.

tert-Butyl 4-chlorobenzoyloxycarbamate (9).

(WO 2007/145888) M.p. 45° C. (determined by differential scanning calorimetry, slow onset); FTIR (neat, cm$^{-1}$) 3250, 2982, 2935, 1763, 1720, 1596, 1485, 1401, 1369, 1328, 1284, 1243, 1187, 1159, 1117, 1106, 1089, 1050, 1029, 1000, 956, 940, 925, 868, 842, 784, 745, 730, 679; $^1$H NMR (500 MHz; CDCl$_3$) δ 8.23 (s, 1H); 8.00-8.05 (m, 2H), 7.42-7.49 (m, 2H), 1.51 (s, 9H); $^{13}$C NMR (125 MHz; CDCl$_3$) δ 165.3, 155.4, 140.7, 131.2, 129.1, 125.4, 83.3, 28.0; HRMS (ES+) m/z calcd for C$_{12}$H$_{14}$ClNO$_4$ (M+Na)$^+$ 294.0504, found 294.0507.

tert-Butyl 4-Chlorobenzoyloxycarbamate (9) (larger scale). To a solution of tert-butyl hydroxycarbamate (9.76 g, 73.3 mmol) in DCM (120 mL) at 0° C., is added 4-chlorobenzoyl chloride (8.13 mL, 73.3 mmol) followed by the dropwise addition of

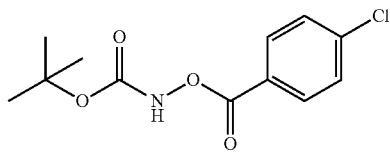

9 triethylamine (10.31 mL, 140.0 mmol). The reaction is allowed to stir at room temperature for 1 h before being quenched by the addition of water. The organic layer is separated and washed with sat. NaHCO$_3$ solution (2×150 mL), brine (100 mL) and dried over MgSO$_4$ before being concentrated. The residue is recrystallised from hexanes to give the title compound (17.3 g, 87%) as colorless crystals.

(9H-Fluoren-9-yl)methyl hydroxycarbamate.

(Mellor, S. L.; McGuire, C.; Chan, W. C.; *Tet. Lett.*, 1997, 38, 3311-3314.)

To a biphasic mixture of hydroxylamine hydrochloride (3.00 g, 43.2 mmol) in DCM (50

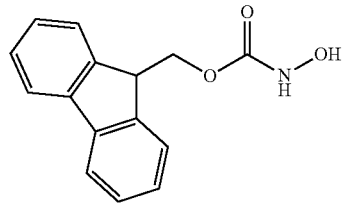 [SMILES: O=C(NO)OCC1c2ccccc2-c2ccccc21]

mL; and water (20 mL) at 0° C. is added sodium bicarbonate (7.30 g, 87.0 mmol) portionwise. After 10 min FmocCl (12.0 g, mmol) is added portionwise to the vigorously stirred suspension which is then left to stir for 1 h at room temperature. The white precipitate that formed filtered and washed with DCM and water. The filter cake is then dissolved in ethyl acetate and washed with brine, dried over MgSO$_4$ and concentrated to give the title compound (5.20 g, 47%) as a white solid which does not require any further purification. $^1$H NMR (500 MHz; DMSO-d$_6$) δ 9.75 (br s, 1H), 8.78 (s, 1H), 7.89 (d, J=7.5 Hz, 2H), 7.70 (d, J=7.5 Hz, 2H), 7.42 (t, J=7.4 Hz, 2H), 7.34 (t, J=7.4 Hz, 2H), 4.35 (d, J=7.0 Hz, 2H), 4.24 (t, J=7.0 Hz, 1H); $^{13}$C NMR (125 MHz; DMSO-d$_6$) δ 157.5, 143.7, 140.7, 127.6, 127.0, 125.1, 120.0, 65.5, 46.6; HRMS (ES+) m/z calcd for C$_{15}$H$_{13}$NO$_3$ (M+Na)$^+$ 278.0788, found 278.0793.

(9H-Fluoren-9-yl)methyl 4-Chlorobenzoyloxycarbamate (10).

To a solution of (9H-fluoren-9-yl)methyl hydroxycarbamate (5.20 g, 20.4 mmol) in ethyl acetate (300 mL) at −10° C. is added 4-chlorobenzoyl chloride (3.56 g, 20.3 mmol). Triethylamine (3 mL, 21.3 mmol) is added dropwise keeping the internal temperature below −5° C. After 10 min water (100 mL) is added and the separated aqueous layer is

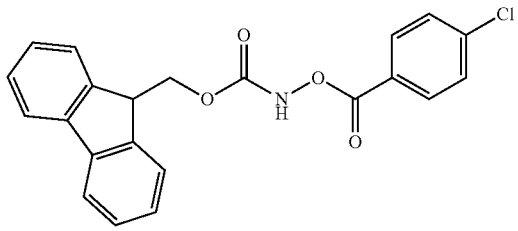 [SMILES: O=C(NOC(=O)c1ccc(Cl)cc1)OCC1c2ccccc2-c2ccccc21]

extracted with ethyl acetate (2×50 mL). The combined organic phases are washed with sat. NaHCO$_3$ solution (100 mL), brine (100 mL), dried over MgSO$_4$ and concentrated to give 10 (7.90 g, 98%) as a white solid which requires no purification prior to further use. An analytical sample is prepared by flash column chromatography (silica gel, petroleum ether/DCM 1:1 and 0:1)

(9H-Fluoren-9-yl)methyl 4-Chlorobenzoyloxycarbamate (10). M.p. 156° C. (determined by differential scanning calorimetry, sharp onset); FTIR (neat, cm$^{-1}$) 3238, 3018, 2982, 2890, 1767, 1741, 1717, 1595, 1486, 1452, 1403, 1373, 1320, 1275, 1231, 1173, 1118, 1092, 1040, 1011, 962, 935, 880, 847, 792, 783, 755, 736, 682; $^1$H NMR (500 MHz; CDCl$_3$) δ 8.40 (s, 1H, NH), 7.96-8.01 (m, 2H), 7.71 (d, J=7.5 Hz, 2H), 7.55 (dd, J=0.9, 7.5 Hz, 2H), 7.44-7.47 (m, 2H), 7.37 (t, J=7.5 Hz, 2H), 7.25 (td, J=1.1, 7.5 Hz, 2H), 4.54 (d, J=6.9 Hz, 2H), 4.24 (t, J=6.9 Hz, 1H); $^{13}$C NMR (125 MHz; CDCl$_3$) δ 164.9, 156.4, 143.2, 141.3, 1410, 131.3, 129.2, 127.9, 127.2, 125.0, 120.1, 68.5, 46.8; HRMS (ES+) m/z calcd for C$_{22}$H$_{16}$ClNO$_4$ (M+Na)$^+$ 416.0660, calcd 416.0660.

(1R,2R,3S,4S,5S)-3-(Ethoxycarbonylamino)-4-hydroxy-5-(hydroxymethyl)cyclo-pentane-1,2-diyl dibenzoate (2) and (1R,2R,3S,4S,5R)-4-(Ethoxycarbonylami-no)-3-hydroxy-5-(hydroxymethyl)cyclo-pentane-1,2-diyl dibenzoate (3).

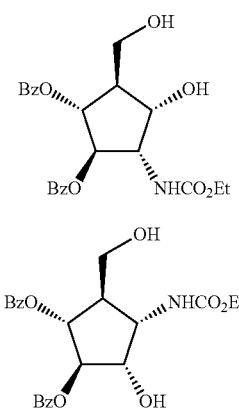

(Blattner, R.; Gerard, P. J.; Spindler-Barth, M. *Pestic. Sci.* 1997, 50, 312-318; Griffith, D. A.; Danishefsky, S. J. *J. Am. Chem. Soc.* 1996, 118, 9526-9538 and literature cited; Blattner, R.; Furneaux, R. H.; Kermmitt, T.; Tyler, P. C.; Ferrier, R. J.; Tiden, A.-K. *J. Chem. Soc., Perkin Trans.* 1 1994, 3411-3421; Blattner, R.; Furneaux, R. H.; Lynch, G. P. *Carbhydrate Res.* 1996, 294, 29-40.) Osmium tetroxide (150 mg, 592 μmol) is added to a solution of ethyl 4-chlorobenzoyloxycarbamate 7 (7.22 g, 29.6 mmol) in tert-BuOH (70.0 mL) and stirred at room temperature for 10 min. (1R,2R,5R)-5-(hydroxymethyl)-cyclopent-3-ene-1,2-diyl dibenzoate[8] (5.00 g, 14.8 mmol) as a solution in tert-BuOH (80 mL) is added to the carbamate solution followed by the addition of water (50 mL) and the reaction is stirred at room temperature for 3 h. The reaction is quenched by adding sat. $K_2S_2O_5$ (50 mL) and stirring for 15 min. Ethyl acetate (100 mL) is added to the reaction solution, which is then washed with water (100 mL), dried with $MgSO_4$ and the solvent removed under reduced pressure. The residue is purified by flash column chromatography (silica gel, petroleum ether/ethyl acetate 8:2 then 1:1 then 3:7) to yield 2.91 g of a 10:1 mixture of 2 (40%) and the triol resulting from dihydroxylation along with 3 (2.93 g, 44%) as an off-white foam. The NMR data of 2 are consistent with that previously reported. (Blattner, R.; Gerard, P. J.; Spindler-Barth, M. *Pestic. Sci.* 1997, 50, 312-318; Griffith, D. A.; Danishefsky, S. J. *J. Am. Chem. Soc.* 1996, 118, 9526-9538 and literature cited; Blattner, R.; Furneaux, R. H.; Kermmitt, T.; Tyler, P. C.; Ferrier, R. J.; Tiden, A.-K. *J. Chem. Soc., Perkin Trans.* 1 1994, 3411-3421; Blattner, R.; Furneaux, R. H.; Lynch, G. P. *Carbhydrate Res.* 1996, 294, 29-40.)

(3) M.p. 95.5-97° C.; FTIR (KBr, cm$^{-1}$) 3422.1, 2980.8, 1722.3, 1601.9, 1523.5, 1452.3, 1272.9, 1177.7, 1112.4, 1070.0, 1026.8, 711.7, 419.0; $[\alpha]^{21}_D$=-56.2 (c 1.37, CHCl$_3$); lit.[7] $[\alpha]_D$=-36; $^1$H NMR (500 MHz, CDCl$_3$) δ 8.05-8.01 (m, 4H), 7.57-7.51 (m, 2H), 7.43-7.38 (m, 6H), 5.73 (d, J=7.6 Hz, 1H), 5.59 (dd, J=1.0, 9.4 Hz, 1H), 5.22 (d, J=4.5 Hz, 1H), 4.26-4.17 (m, 2H), 4.14 (d, J=7.0 Hz, 1H), 4.12 (d, J=7.2 Hz, 1H), 3.84-3.75 (m, 2H), 3.61 (t, J=5.9 Hz, 1H), 2.48-2.41 (m, 1H), 1.24 (t, J=7.1 Hz, 3H); $^{13}$C NMR (125 MHz, CDCl$_3$) δ 167.0, 166.1, 157.5, 133.6, 133.3, 129.9, 129.8, 129.5, 129.1, 128.5, 128.4, 84.7, 77.3, 77.1, 76.8, 74.9, 74.1, 61.5, 60.4, 58.3, 50.9, 49.4, 14.5; HRMS (ES+) m/z calcd for $C_{23}H_{25}NO_8$ (M+Na)$^+$ 466.1478, found 466.1475; Anal. calcd for $C_{23}H_{25}NO_8$: C, 62.30; H, 5.68; N, 3.16. Found C, 62.06; H, 5.75; N, 3.12.

(±)-(2S,3R)-Isopropyl 3-(ethoxycarbonylamino)-2-hydroxy-3-phenylpropanoate (11a) and (±)-(2S,3R)-isopropyl 2-(ethoxycarbonylamino)-3-hydroxy-3-phenylpropanoate (11b). Osmium tetroxide (53.0 mg, 211 μmol) is added to a solution of ethyl 4-chlorobenzoyl-oxycarbamate 7 (1.80 g, 7.37 mmol) in tert-BuOH (18 mL) and stirred at room temperature for 10 min. Isopropyl cinnamate (1.00 g, 5.26 mmol) as a solution in tert-BuOH (18 mL) is added to the carbamate solution followed

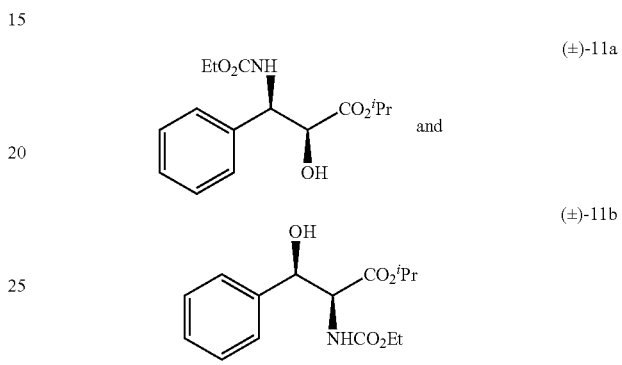

by the addition of water (12 mL) and the reaction is stirred at room temperature for 3 h. The reaction is quenched with sat. $K_2S_2O_5$ solution (5 mL) and stirred for 5 min. Water (100 mL) is added to the reaction solution and it is extracted with ethyl acetate (2×100 mL). The organic layers are combined, washed with sat. NaHCO$_3$ solution (2×100 mL) and brine, dried over MgSO$_4$ and the solvent is removed under reduced pressure. The residue is purified by flash column chromatography (silica gel, petroleum spirit/ethyl acetate 8:2) to yield 11a (171 mg, 11%) as a colorless gum, 11b (171 mg, 11%) as a colorless gum, and a 1:1.4 mixture of 11a and 11b (1.14 g, 74%).

(±)-(2S,3R)-Isopropyl 3-(Ethoxycarbonylamino)-2-hydroxy-3-phenylpropanoate (11a) FTIR (neat, cm$^{-1}$) 3377, 3050, 3035, 3000, 2983, 2947, 1712, 1690, 1526, 1500, 1472, 1458, 1449, 1437, 1420, 1373, 1353, 1329, 1311, 1291, 1257, 1232, 1218, 1183, 1171, 1145, 1115, 1093, 1042, 1033, 992, 948, 938, 917, 880, 848, 821, 807, 775, 742, 702, 668; $^1$H NMR (500 MHz, CDCl$_3$) δ 7.39-7.31 (m, 4H), 7.29-7.24 (m, 2H), 5.68 (br d, J=8.5 Hz, 1H), 5.26 (br d, J=8.5 Hz, 1H), 5.16-5.07 (m, 2H), 4.42 (s, 1H), 4.12-4.01 (m, 2H), 3.44 (br s, 1H), 1.29 (d, J=6.3 Hz, 3H), 1.27 (d, J=6.3 Hz, 3H), 1.20 (t, J=6.8 Hz, 3H); $^{13}$C NMR (125 MHz, CDCl$_3$) δ 172.31, 155.90, 139.25, 128.51, 127.66, 126.78, 73.63, 70.62, 61.09, 56.32, 21.67, 21.47, 14.50; HRMS (ES+) m/z calcd for $C_{15}H_{21}NO_5$ (M+Na)$^+$ 318.1317, found 318.1324.

(±)-(2S,3R)-Isopropyl 2-(Ethoxycarbonylamino)-3-hydroxy-3-phenylpropanoate (11b): FTIR (neat, cm$^{-1}$) 3404, 3067, 3032, 2982, 2938, 1701, 1513, 1504, 1477, 1469, 1455, 1437, 1419, 1375, 1331, 1271, 1209, 1147, 1105, 1057, 977, 935, 916, 870, 836, 821, 776, 700, 668; $^1$H NMR (500 MHz, CDCl$_3$) δ 7.39-7.24 (m, 5H), 5.58 (d, J=9.1 Hz, 1H), 5.14 (d, J=3.2 Hz, 1H), 5.07-4.96 (m, 1H), 4.50 (br s, 1H), 4.05-3.90 (br m, 2H), 3.34 (br s, 1H), 1.23 (d, J=6.2 Hz, 3H), 1.18-1.11 (m, 6H); $^{13}$C NMR (125 MHz, CDCl$_3$) δ 170.27, 156.61, 139.92, 128.28, 127.96, 126.12, 73.88, 69.49, 61.21, 60.03, 21.70, 21.52, 14.41; HRMS (ES+) m/z calcd for $C_{15}H_{21}NO_5$ (M+Na)$^+$ 318.1312, found 318.1320.

(±)-(2S,3R)-Isopropyl 3-(Benzyloxycarbonylamino)-2-hydroxy-3-phenylpropanoate (12a) and (±)-(2S,3R)-isopropyl 2-(benzyloxycarbonylamino)-3-hydroxy-3-phenylpropanoate (12b).

Method A. Isopropyl cinnamate (1.00 g, 5.26 mmol) is treated with osmium tetroxide (53.0 mg, 211 μmol) and benzyl 4-chlorobenzoyloxycarbamate 8 (2.25 g, 7.37 mmol) in

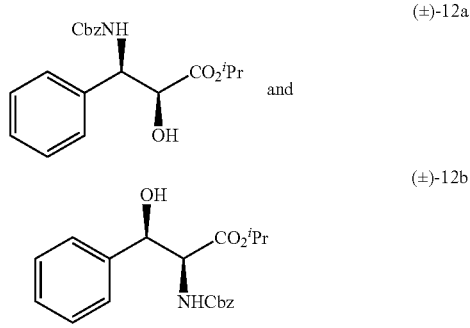

tert-BuOH (36 mL) and water (12 mL) following the procedure outlined for the preparation of 11a and 11b (vide supra) to yield 12a (175 mg, 9%) and 12b (175 mg, 9%) as off-white solids, and a 1:1 mixture of 12a and 12b (1.45 g, 77%).

Method B; Osmium tetroxide (8.00 mg, 31.6 μmol) is added to a solution of benzyl 4-chlorobenzoyloxycarbamate 8 (338 mg, 1.11 mmol) in acetonitrile (3.5 mL) and stirred at room temperature for 10 min. Isopropyl cinnamate (150 mg, 789 μmol) as a solution in acetonitrile (3.5 mL) is added to the carbamate solution followed by the addition of water (0.85 mL) and the reaction is stirred at room temperature for 3 h. The reaction is quenched by adding sat. $K_2S_2O_5$ solution (2 mL) and stirred for 5 min. Water (50 mL) is added to the reaction solution and it is extracted with ethyl acetate (2×50 mL). The organic layers are combined and washed with sat. $NaHCO_3$ solution (2×50 mL), followed by brine, then dried with $MgSO_4$ and the solvent is removed under reduced pressure. The residue is purified by flash column chromatography (silica gel, petroleum spirit/ethyl acetate 4:1) to yield a 1:1.4 mixture of 12a and 12b (270 mg, 96%).

(±)-(2S,3R)-Isopropyl 3-(benzyloxycarbonylamino)-2-hydroxy-3-phenylpropanoate (12a) M.p. 96-97° C.; FTIR (neat, cm$^{-1}$) 3359, 3041, 2980, 2935, 1715, 1696, 1533, 1497, 1469, 1454, 1437, 1419, 1387, 1374, 1351, 1326, 1309, 1287, 1256, 1233, 1218, 1183, 1147, 1115, 1100, 1052, 1029, 979, 954, 915, 906, 853, 839, 821, 774, 750, 739, 721, 703, 697, 668; $^1$H NMR (500 MHz, CDCl$_3$) δ 7.39-7.23 (m, 10H), 5.78 (br d, 9.2 J=Hz, 1H), 5.28 (br d, J=9.2 Hz, 1H), 5.11-4.99 (m, 3H), 4.41 (s, 1H), 3.37 (br s, 1H), 1.26 (d, J=6.1 Hz, 3H), 1.19 (d, J=6.1 Hz, 3H); $^{13}$C NMR (125 MHz, CDCl$_3$) δ 172.27, 155.70, 139.09, 136.39, 128.57, 128.50, 128.47, 128.09, 127.76, 126.82, 73.59, 70.74, 66.97, 56.48, 21.67, 21.44; HRMS (ES+) m/z calcd for $C_{20}H_{23}NO_5$ (M+Na)$^+$ 380.1468, found 380.1469.

(±)-(2S,3R)-Isopropyl 2-(benzyloxycarbonylamino)-3-hydroxy-3-phenylpropanoate (12b): M.p. 92-93° C.; FTIR (neat, cm$^{-1}$) 3499, 3366, 3036, 2983, 2939, 1725, 1691, 1522, 1498, 1454, 1438, 1400, 1376, 1356, 1316, 1292, 1239, 1211, 1195, 1160, 1105, 1055, 1029, 1015, 1002, 980, 956, 916, 903, 863, 836, 795, 778, 737, 712, 703, 694, 669; $^1$H NMR (500 MHz, CDCl$_3$) δ 7.35-7.19 (m, 10H), 5.66 (br d, J=8.4 Hz, 1H), 5.17 (s, 1H), 5.05-4.93 (m, 3H), 4.54 (br d, J=7.2 Hz, 1H), 3.13 (br s, 1H), 1.22 (d, J=6.2 Hz, 3H), 1.14 (d, J=6.2 Hz, 3H); $^{13}$C NMR (125 MHz, CDCl$_3$) δ 170.14, 156.36, 139.79, 136.30, 128.44, 128.37, 128.30, 128.05, 127.91, 126.11, 73.89, 69.64, 66.94, 60.09, 21.71, 21.55; HRMS (ES+) m/z calcd for $C_{20}H_{23}NO_5$ (M+Na)$^+$ 380.1468, obsd 380.1468.

Chiral Methods (Table 3, (+)-12a, (−)-12a, (+)-12b)

(+)-12a. Following the general AA procedure above, isopropyl cinnamate (150 mg, 0.79 mmol) is reacted with osmium tetroxide (8 mg, 32 μmol), (DHQ)$_2$PHAL (31.0 mg, 39.5 μmol) and benzyl 4-chlorobenzoyloxycarbamate 8 (338 mg, 1.11 mmol). (The solution changed from a yellow colour to dark green very quickly after addition of the isopropyl cinnamate and a white precipitate formed during the course of the reaction.) Subsequent flash column chromatography (silica gel, petroleum spirit/ethyl acetate 4:1) affords the products (+)-12a and 12b (270 mg, 96%) in a ratio of 12.7:1 (ee. (+)-12a. 97%; 12b: 33%). (+)-12a; Spectroscopic data are identical to (+)-12a above except: $[\alpha]^{21}_D$=+15.1 (c 1.26, CHCl$_3$).

(−)-12a. Following the general AA procedure above, isopropyl cinnamate (150 mg, 0.79 mmol) is reacted with osmium tetroxide (8 mg, 32 μmol), (DHQD)$_2$PHAL (31.0 mg, 39.5 μmol) and benzyl 4-chlorobenzoyloxycarbamate 8 (338 mg, 1.11 mmol). (The solution changed from a yellow colour to dark green very quickly after addition of the isopropyl cinnamate and a white precipitate formed during the course of the reaction.) Subsequent flash column chromatography (silica gel, petroleum spirit/ethyl acetate 4:1) affords the products (−)-12a and 12b (269 mg, 96%) in a ratio of 13.4:1 (ee. (−)-12a: 97%; 12b: 28%). (−)-12a; Spectroscopic data is identical to (±)-12a above except: $[\alpha]^{21}_D$=−14.7 (c 1.07, CHCl$_3$).

(+)-12b. Following the general AA procedure above, isopropyl cinnamate (150 mg, 0.79 mmol) is reacted with osmium tetroxide (8 mg, 32 μmol), (DHQ)$_2$AQN (31.0 mg, 39.5 μmol) and benzyl 4-chlorobenzoyloxycarbamate 8 (338 mg, 1.11 mmol). (The solution changed from a yellow color to dark green within a minute after addition of the isopropyl cinnamate and no precipitate formed during the course of the reaction) Subsequent flash column chromatography (silica gel, petroleum spirit/ethyl acetate 4:1) affords the products 12a and 12b (253 mg, 90%) in a ratio of 1:1.6 (ee. 12a: 71%; 12b: 71%).

(±)-(2S,3R)-Isopropyl 3-(tert-Butoxycarbonylamino)-2-hydroxy-3-phenylpropanoate (13a) and (±)-(2S,3R)-isopropyl 2-(tert-butoxycarbonylamino)-3-hydroxy-3-phenylpropanoate (13b). Following the general AA procedure above, isopropyl cinnamate (150 mg, 0.79 mmol) is reacted with osmium tetroxide (8 mg, 32 μmol) and Boc reagent 9 (300 mg, 1.10 mmol). Subsequent flash column chromatography (silica gel, ethyl acetate/petroleum ether 15:85) gives 238 mg (93%) of 13a as a white solid and 13b as a viscous oil in a 1:1.8 ratio (determined by HPLC). Analytical samples of 13a and 13b are obtained.

(±)-(2S,3R)-Isopropyl 3-(tert-Butoxycarbonylamino)-2-hydroxy-3-phenylpropanoate (13a). M.p. (determined by differential scanning calorimetry, sharp onset) 136-137° C.; FTIR (neat, cm$^{-1}$) 3392, 2978, 2943, 1713, 1685, 1517, 1473, 1578, 1422, 1389, 1355, 1327, 1313, 1293, 1234, 1218, 1170, 1146, 1116, 1100, 1055, 1039, 1022, 952, 917, 877, 848, 822, 790, 775, 755, 729, 703; $^1$H NMR (500 MHz; CDCl$_3$) δ

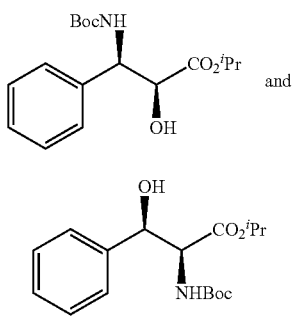

7.41-7.26 (m, 5H, PhH), 5.39 (d, J=8.3 Hz, 1H), 5.23 (d, J=8.3 Hz, 1H), 5.12 (sep, J=6.4 Hz, 1H), 4.42 (br s, 1H, H-2), 3.17 (br s, 1H, OH), 1.40 (s, 9H), 1.33-1.28 (m, 6H); $^{13}$C NMR (125 MHz; CDCl$_3$) δ 172.5, 155.0, 139.5, 128.5, 127.6, 126.8, 79.7, 73.7, 70.7, 55.9, 28.3, 21.7, 21.5; HRMS (ES+) m/z calcd for $C_{17}H_{25}NO_5$ (M+Na)$^+$ 346.1625, found 346.1634.

(±)-(2S,3R)-Isopropyl 2-(tert-Butoxycarbonylamino)-3-hydroxy-3-phenylpropanoate (13b). FTIR (neat, cm$^{-1}$) 3432, 2981, 2935, 1695, 1498, 1454, 1392, 1367, 1334, 1267, 1162, 1106, 1054, 1027, 982, 936, 916, 861, 836, 823, 776, 736, 701; $^1$H NMR (500 MHz; CDCl$_3$) δ 7.42-7.20 (m, 5H, PhH), 5.34 (br s, 1H, NH), 5.14 (br s, 1H), 5.02 (sep, J=6.1 Hz, 1H), 4.46 (br s, 1H, H-2), 3.17 (br s, 1H, OH), 1.42-1.26 (br m, 9H), 1.25 (d, J=6.1 Hz, 3H), 1.17 (d, J=6.1 Hz, 3H); $^{13}$C NMR (125 MHz; CDCl$_3$) δ 170.3, 155.7, 140.0, 128.2, 127.8, 126.1, 79.9, 74.1, 69.4, 59.6, 28.1, 21.7, 21.5; HRMS (ES+) m/z calcd for $C_{17}H_{25}NO_5$ (M+Na)$^+$ 346.1625, found 346.1625.

(±)-(2S,3R)-Isopropyl 2-{[(9H-fluoren-9-yl)methoxy]carbonylamino}-3-hydroxy-3-phenyl-propanoate (14a) and (±)-(2S,3R)-isopropyl 3-{[(9H-fluoren-9-yl)methoxy]carbonylamino}-2-hydroxy-3-phenylpropanoate (14b). Isopropyl-cinnamate (150 mg, 0.79 mmol) is reacted with osmium tetroxide (8 mg, 32 μmol) and

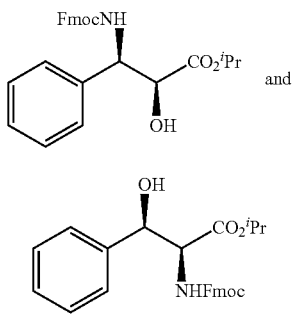

Fmoc-reagent 10 (434 mg, 1.10 mmol) using the general AA procedure as described above. The crude product is purified by flash column chromatography (silica gel, ethyl acetate/petroleum ether 1:4 and 3:7) to afford a mixture of regioisomers 14a and 14b (338 mg, 96%) in a 1:1.91 ratio. Analytical samples of each regioisomer are obtained for structural determination.

(±)-(2S,3R)-Isopropyl 2-{[(9H-fluoren-9-yl)methoxy]carbonylamino}-3-hydroxy-3-phenyl-propanoate (14a). M.p. (determined by differential scanning calorimetry, sharp onset) 118° C.; FTIR (neat, cm$^{-1}$) 3384, 2976, 1721, 1695, 1519, 1449, 1355, 1324, 1287, 1250, 1217, 1182, 1112, 1026, 978, 914, 823, 776, 757, 732, 740, 700; $^1$H NMR (500 MHz; CDCl$_3$) δ 7.74 (d, J=7.7 Hz, 2H), 7.59-7.50 (m, 2H), 7.42-7.25 (m, 9H), 5.70 (d, J=9.4 Hz, 1H, NH), 5.29 (d, J=9.4 Hz, 1H, CH(NH)), 5.11 (sep, J=6.2 Hz, 1H), 4.46 (s, 1H, CH(OH)), 4.41-4.29 (2H, m), 4.19 (t, J=6.3 Hz, 1H), 3.23 (br s, 1H, OH), 1.29 (d, J=6.2 Hz, 3H), 1.24 (d, J=6.2 Hz, 3H); $^{13}$C NMR (125 MHz; CDCl$_3$) δ 172.3, 155.6, 143.8, 141.3, 139.0, 128.7, 127.8, 127.7, 127.1, 126.7, 125.0, 120.0, 73.5, 70.9, 67.0, 56.3, 47.2, 21.7, 21.6; HRMS (ES+) m/z calcd for $C_{27}H_{27}NO_5$ (M+Na)$^+$ 468.1781, found 468.1782.

(±)-(2S,3R)-isopropyl 3-{[(9H-fluoren-9-yl)methoxy]carbonylamino}-2-hydroxy-3-phenylpropanoate (14b). M.p. (determined by differential scanning calorimetry, slow onset) 133° C.; FTIR (neat, cm$^{-1}$) 3502, 3385, 2981, 1720, 1691, 1524, 1449, 1374, 1315, 1288, 1247, 1232, 1163, 1105, 1088, 1065, 1039, 992, 960, 836, 759, 742, 728, 713, 702; $^1$H NMR (500 MHz; CDCl$_3$) δ 7.73 (d, J=7.5 Hz, 2H), 7.55-7.47 (m, 2H, ArH), 7.41-7.25 (m, 9H, ArH), 5.64 (d, J=8.4 Hz, 1H, NH), 5.22 (br s, 1H, CH(OH)), 5.06 (sep, J=6.5 Hz, 1H, CH(CH$_3$)$_2$), 4.58 (br d, J=6.7 Hz, 1H), 4.32-4.18 (m, 2H), 4.15-4.08 (m, 1H), 2.84 (br s, 1H, OH), 1.25 (d, J=6.5 Hz, 3H), 1.18 (d, J=6.5 Hz, 3H); $^{13}$C NMR (125 MHz; CDCl$_3$) δ 170.1, 156.3, 143.8, 141.3, 139.7, 128.4, 128.2, 127.7, 127.1, 126.1, 125.1, 119.9, 74.0, 69.7, 67.2, 59.9, 47.1, 21.8, 21.6; HRMS (ES+) m/z calcd for $C_{27}H_{27}NO_5$ (M+Na)$^+$ 468.1781, found 468.1781.

(±)-Benzyl 2-Hydroxy-2-phenylethylcarbamate (15a) and (±)-Benzyl 2-Hydroxy-1-phenylethylcarbamate (15b).

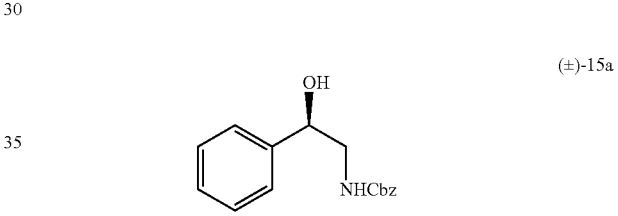

Styrene (250 μL, 2.18 mmol) is reacted with osmium tetroxide (22.1 mg, 87.1 μmol) and benzyl reagent 8 (4-chlorobenzoyloxycarbamate) (933 mg, 3.05 mmol) using the general AA procedure as described above. The crude product is purified by flash column chromatography (silica gel, ethyl acetate/petroleum ether 3:7) to afford both reaction products (15a and 15b) combined as an off-white solid (570 mg, 96%). Analytical samples of each regioisomer are obtained for structural determination.

15a: M.p. 113° C. (petroleum spirit/ethyl acetate) (Herranz, E.; Biller, S. A.; Sharpless, K. B.; *J. Am. Chem. Soc.* 1978, 100, 3596-3598), m.p.: 114-115° C.; FTIR (cm$^{-1}$) 3368, 3272, 3063, 3025, 2936, 2887, 1693, 1605, 1586, 1549, 1497, 1453, 1431, 1369, 1345, 1318, 1271, 1240, 1210, 1162, 1098, 1066, 1024, 993, 948, 918, 890, 834, 822, 781, 755, 741, 718, 705, 697; $^1$H NMR (500 MHz, CDCl$_3$) δ 7.34-7.22 (m, 10H), 5.32 (br s, 1H), 5.05 (s, 2H), 4.81-4.67 (br m, 1H), 3.54-3.44 (br m, 1H), 3.29-3.17 (m, 1H), 3.03 (br s, 1H); $^{13}$C NMR (125 MHz, CDCl$_3$) δ 157.14, 141.57, 136.40, 128.56, 128.54, 128.17, 128.12, 127.95, 125.89, 73.52, 66.95, 48.53; HRMS (ES+) m/z calcd for $C_{16}H_{17}NO_3$ (M+Na)$^+$ 294.1101, found 294.1104.

15b: M.p. 85° C. (petroleum spirit/ethyl acetate) (Herranz, E.; Biller, S. A.; Sharpless, K. B.; *J. Am. Chem. Soc.* 1978, 100, 3596-3598), m.p.: 83-84.5° C.; FTIR (cm$^{-1}$) 3350, 3036, 2930, 2879, 1683, 1587, 1531, 1496, 1451, 1348, 1326, 1277, 1246, 1219, 1193, 1147, 1099, 1076, 1057, 1027, 915, 841, 778, 762, 734, 700; $^1$H NMR (500 MHz, CDCl$_3$) δ 7.37-7.24 (m, 10H), 5.54 (br s, 1H), 5.13-5.05 (m, 2H), 4.83 (br s, 1H), 3.90-3.77 (m, 2H), 2.19 (br s, 1H); $^{13}$C NMR (125 MHz, CDCl$_3$) δ 156.42, 139.12, 136.28, 128.83, 128.52, 128.17, 127.86, 126.57, 67.04, 66.46, 57.17; HRMS (ES+) m/z calcd for C$_{16}$H$_{17}$NO$_3$ (M+Na)$^+$ 294.1101, found 294.1100.

(±)-Benzyl 2-Hydroxy-3-phenylpropylcarbamate (16a) and (±)-Benzyl 1-Hydroxy-3-phenylpropan-2-ylcarbamate (16b). Allyl benzene (288 μL, 2.18 mmol) is reacted with osmium tetroxide (22.1 mg, 87.1 mol) and benzyl reagent 8 (benzyl 4-chlorobenzoyloxycarbamate) (933 mg, 3.05 mmol) for 15 h, using the general AA

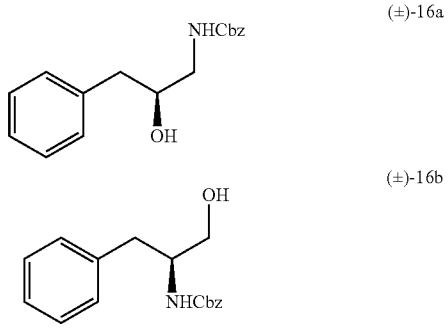

procedure as described above. The crude product is purified by flash column chromatography (silica gel, ethyl acetate/petroleum ether 3:7) to afford both reaction products (16a and 16b) combined as an off-white solid (565 mg, 91%). Analytical samples of each regioisomer are obtained for structural determination.

16a: M.p. 150° C. (petroleum spirit/ethyl acetate); FTIR (cm$^{-1}$) 3352, 3034, 2943, 1688, 1537, 1494, 1466, 1454, 1432, 1352, 1319, 1286, 1251, 1221, 1150, 1083, 1070, 1042, 1028, 1001, 962, 911, 839, 768, 749, 725, 701, 696; $^1$H NMR (500 MHz, CDCl$_3$) δ 7.34-7.12 (m, 10H), 5.40-5.34 (br m, 1H), 5.07 (s, 2H), 3.91-3.84 (br m, 1H), 3.41-3.33 (br m, 1H), 3.12-3.02 (m, 1H), 2.77-2.62 (m 3H); $^{13}$C NMR (125 MHz, CDCl$_3$) δ 157.11, 137.65, 136.49, 129.38, 128.65, 128.55, 128.16, 128.13, 126.66, 71.99, 66.90, 46.37, 41.24; HRMS (ES+) m/z calcd for C$_{17}$H$_{19}$NO$_3$ (M+Na)$^+$ 308.1257, found 308.1256.

16b: M.p. 78° C. (petroleum spirit/ethyl acetate); FTIR (cm$^{-1}$) 3320, 3064, 3031, 2954, 2876, 1688, 1602, 1543, 1498, 1466, 1454, 1446, 1379, 1312, 1260, 1190, 1146, 1085, 1069, 1053, 1015, 967, 918, 907, 866, 842, 776, 746, 697; $^1$H NMR (500 MHz, CDCl$_3$) δ 7.37-7.16 (m 10H), 5.07 (s, 2H), 5.01 (d, J=6.8 Hz, 1H), 3.94 (s, 1H), 3.70-3.52 (m 2H), 2.85 (d, J=6.8 Hz, 2H); $^{13}$C NMR (125 MHz, CDCl$_3$) δ 156.46, 137.55, 136.38, 129.26, 128.62, 128.53, 128.14, 128.05, 126.64, 66.83, 64.00, 54.15, 37.37; HRMS (ES+) m/z calcd for C$_{17}$H$_{19}$NO$_3$ (M+Na)$^+$ 308.1257, found 308.1260.

(±)-Benzyl (1R,2R)-2-hydroxy-1,2-diphenylethylcarbamate (17). trans-Stillbene (392 mg, 2.18 mmol) is reacted with osmium tetroxide (22.1 mg, 87.1 μmol) and benzyl reagent 8 (benzyl 4-chlorobenzoyloxycarbamate) (933 mg, 3.05 mmol) for 3 h using the general AA procedure as described above. The crude product is purified by flash

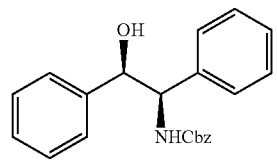

column chromatography (silica gel, ethyl acetate/petroleum ether 2:8) to afford 17 (725 mg, 96%) as an off-white solid. M.p. 152° C. (methanol) (Li, G.; Angert, H. H.; Sharpless, K. B. *Angew. Chem. Int. Ed. Engl.* 1996, 35, 2813-2817), m.p. 149-151° C. (methanol); FTIR (cm$^{-1}$) 3353, 3034, 2943, 2889, 2488, 1687, 1603, 1533, 1493, 1467, 1454, 1431, 1350, 1318, 1286, 1250, 1220, 1198, 1164, 1150, 1069, 1042, 1027, 1001, 961, 910, 839, 768, 749, 725, 701, 696; $^1$H NMR (500 MHz, CDCl$_3$) δ7.34-7.23 (m, 15H), 5.68 (br s, 6.0 Hz, 1H), 5.05-4.91 (m, 4H), 2.43 (br s, 1H); $^{13}$C NMR (125 MHz, CDCl$_3$) δ 156.30, 140.53, 136.38, 128.61, 128.46, 128.33, 128.00, 127.87, 127.68, 126.85, 126.16; HRMS (ES+) m/z calcd for C$_{22}$H$_{21}$NO$_3$ (M+Na)$^+$ 370.1414, found 370.1413.

(±)-Benzyl (1S,2R)-2-hydroxycyclohexylcarbamate (18): Cyclohexene (220 μL, 2.18 mmol) is reacted with osmium tetroxide (22.1 mg, 87.1 μmol) and benzyl reagent 8 (benzyl 4-chlorobenzoyloxycarbamate) (933 mg, 3.05 mmol) for 3 h using the general AA procedure as described above. The crude product is purified by flash column

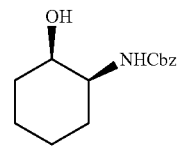

chromatography (silica gel, ethyl acetate/petroleum ether 2:8) to afford 18 (539 mg, 99%) as an off-white solid. $^1$H NMR (500 MHz, CDCl$_3$) δ 7.38-7.25 (m, 5H), 5.41 (br s, 8.5 Hz, 1H), 5.11-5.01 (m, 2H), 3.90 (br s, 1H), 3.62 (br s, 1H), 2.71 (br s, 1H), 1.74-1.66 (m, 1H), 1.64-1.46 (m, 5H), 1.39-1.24 (m, 2H); $^{13}$C NMR (125 MHz, CDCl$_3$) δ 156.28, 136.56, 128.50, 128.08, 68.88, 66.70, 52.69, 31.67, 27.32, 23.76, 19.74; HRMS (ES+) m/z calcd for C$_{14}$H$_{19}$NO$_3$ (M+Na)$^+$ 272.1257, obsd 272.1260.

(+)-18. Following the general AA procedure above, cyclohexene (45 μL, 0.45 mmol) is reacted with osmium tetroxide (4.5 mg, 18 μmol), (DHQ)$_2$PHAL (17 mg, 22 μmol), and benzyl reagent 8 (191 mg, 0.62 mmol). Subsequent flash column chromatography (silica gel, petroleum spirit/ethyl acetate 19:1 and 7:3) gives (+)-18 (90 mg, 80%) as an off white solid whose spectroscopic properties are identical to that reported for (±)-18. (ee=62%)

(−)-18. Following the general AA procedure above, cyclohexene (45 μL, 0.45 mmol) is reacted with osmium tetroxide (4.5 mg, 18 μmol), (DHQD)$_2$PHAL (17 mg, 22 μmol), and benzyl reagent 8 (191 mg, 0.62 mmol). Subsequent flash column chromatography (silica gel, petroleum spirit/ethyl acetate 19:1 and 7:3) gives (−)-18 (81 mg, 72%) as an off white solid whose spectroscopic properties are identical to that reported for (±)-18. (ee=73%).

(±)-(2R,3R)-Dimethyl 2-(benzyloxycarbonylamino)-3-hydroxysuccinate (19).

Dimethyl fumarate (157 mg, 1.09 mmol) is reacted with osmium tetroxide (11.1 mg, 43.6 μmol) and benzyl reagent 8 (benzyl 4-chlorobenzoyloxycarbamate) (467 mg, 1.53

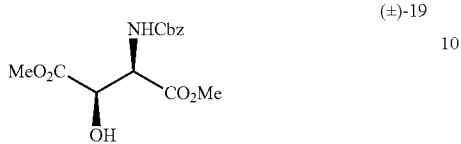

(±)-19 mmol) for 15 h, using the general AA procedure as described above. The crude product is purified by flash column chromatography (silica gel, ethyl acetate/petroleum ether 2:8) to afford 19 (315 mg, 93%) as an off-white solid. M.p. 129° C. (chloroform) (Shin, C.; Obara, T.; Morita, S.; Yonezawa, Y.; Bull. Chem. Soc. Jpn. 1988, 61, 3265-3272.) m.p.: 129-130° C. (benzene); FTIR (cm$^{-1}$) 3358, 3312, 3034, 2957, 2890, 2854, 1749, 1687, 1529, 1439, 1391, 1341, 1265, 1215, 1186, 1173, 1126, 1063, 1031, 984, 971, 952, 927, 910, 860, 802, 779, 762, 740, 699; $^1$H NMR (500 MHz, CDCl$_3$) δ 7.37-7.28 (m, 5H), 5.66 (d, J=9.1 Hz, 1H), 5.09 (s, 2H), 4.85 (d, J=9.1 Hz, 1H), 4.71 (s, 1H) 3.78 (s, 3H), 3.76 (s, 3H), 3.43 (s, 1H); $^{13}$C NMR (125 MHz, CDCl$_3$) δ 172.21, 169.64, 156.05, 136.08, 128.50, 128.17, 127.96, 70.99, 67.24, 56.53, 53.20, 52.97; HRMS (ES+) m/z calcd for C$_{14}$H$_{17}$NO$_7$ (M+Na)$^+$ 334.0897, obsd 334.0899.

(±)-(3S,4R)-Benzyl 3-(benzyloxycarbonylamino)-4-hydroxypyrrolidine-1-carboxylate (20). Benzyl 2,5-dihydro-1H-pyrrole-1-carboxylate (200 mg, 985 μmol) is

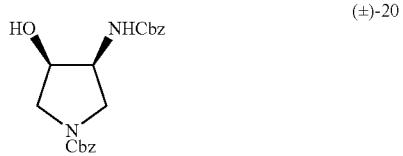 [SMILES: O=C(N[C@H]1CN(C(=O)OCc2ccccc2)C[C@H]1O)OCc1ccccc1]

(±)-20 reacted with osmium tetroxide (10.0 mg, 39.4 μmol) and benzyl reagent 8 (benzyl 4-chlorobenzoyloxycarbamate) (422 mg, 1.38 mmol) for 3 h using the general AA procedure as described above. The crude product is purified by flash column chromatography (silica gel, etheyl acetate/petroleum ether 2:8) to afford 20 (350 mg, 96%) as an oil. $^1$H NMR (500 MHz, CDCl$_3$) δ 7.34-7.25 (m, 10H), 5.58-5.52 (m, 1H), 5.12-5.02 (m, 4H), 4.26-4.13 (m, 2H), 3.81-3.73 (m, 1H) 3.52-3.41 (m, 2H), 3.29-3.15 (m, 1H); $^{13}$C NMR (125 MHz, CDCl$_3$) δ 156.19, 155.18, 154.93, 136.52, 136.43, 136.15, 128.58, 128.50, 128.28, 128.16, 128.08, 127.87, 70.28, 69.47, 67.16, 67.08, 53.29, 53.05, 52.61, 47.92; HRMS (ES+) m/z calcd for C$_{20}$H$_{22}$N$_2$O$_5$ (M+Na)$^+$ 393.1421, found 393.1421.

(−)-Benzyl 3-(Benzyloxycarbonylamino)-4-hydroxypyrrolidine-1-carboxy-late ((−)-20).

Following the general AA procedure above, a solution of benzyl 4-chlorobenzoyloxycarbamate 8 211 mg (0.690 mmol), OsO$_4$ (5.0 mg, 0.020 mmol) and

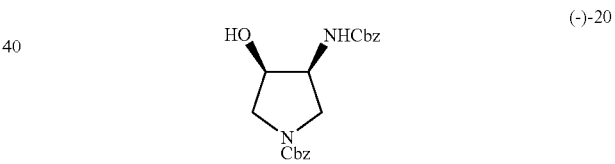

(−)-20

(DHQ)$_2$PHAL (19.0 mg, 0.024 mmol) in acetonitrile (2 mL) and water (0.5 mL) is treated with a solution of benzyl 2,5-dihydro-1H-pyrrole-1-carboxylate (100 mg, 0.492 mmol) in acetonitrile (2 mL) at room temperature for 3 h. Subsequent flash column chromatography (silica gel, petroleum spirit/ethyl acetate 7:3 and 3:7) affords (−)-20 (175 mg, 96%, 35% ee by HPLC) as a colorless oil. [α]$^{20}_D$=−2.05 (c 1.27, CHCl$_3$); FTIR (neat, cm$^{-1}$) 3404/3330 (OH), 2954, 2886, 1679 (C=O), 1531, 1519, 1498, 1454, 1423, 1358, 1357, 1291, 1212, 1159, 1132, 1097, 1041, 1028, 1004, 979, 914, 889, 767, 736, 696, 604; $^1$H NMR (500 MHz, DMSO-d$_6$, 100° C.) δ 7.39-7.28 (m, 10H), 6.60 (br s, 1H), 5.08 (s, 2H), 5.07 (s, 2H), 4.98 (d, J=4.3 Hz, 1H), 4.20-4.16 (m, 1H), 4.06-3.99 (m, 1H), 3.61 (dd, J=7.8, 10.1 Hz, 1H), 3.49 (dd, J=4.3, 11.6 Hz, 1H), 3.34 (dd, J=2.2, 11.6 Hz, 1H), 3.21 (dd, J=9.0, 10.1 Hz, 1H); $^{13}$C NMR (125 MHz, DMSO-d$_6$, 100° C.) δ 155.17, 153.61, 136.64, 136.51, 127.70, 127.68, 127.09, 127.05, 127.00, 126.79, 68.03, 65.32, 65.07, 52.69, 52.03, 47.26; HRMS (ES+) m/z calcd for C$_{20}$H$_{22}$N$_2$O$_5$ (M+Na)$^+$ 393.1421, found 393.1422.

(+)-Benzyl 3-(Benzyloxycarbonylamino)-4-hydroxypyrrolidine-1-carboxy-late ((+)-20). Following the general AA procedure above, a solution of benzyl 4-chlorobenzoyloxycarbamate 211 mg (0.690 mmol), OsO$_4$ (5.0 mg, 0.020 mmol) and (DHQD)$_2$PHAL (19.0 mg, 0.024 mmol) in acetonitrile (2 mL) and water (0.5 mL) is

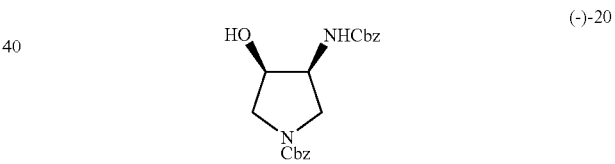

(−)-20 treated with a solution of benzyl 2,5-dihydro-1H-pyrrole-1-carboxylate (100 mg, 0.492 mmol) in acetonitrile (2 mL) at room temperature for 3 h. Subsequent flash column chromatography (silica gel, petroleum spirit/ethyl acetate 7:3 and 3:7) affords (+)-20 (168 mg, 92%, 64% ee by HPLC) as an colorless oil. [α]$^{20}_D$=+2.24 (c 1.34, CHCl$_3$); HRMS (ES+) m/z calcd for C$_{20}$H$_{22}$N$_2$O$_5$ (M+Na)$^+$ 393.1421, found 393.1424. The spectroscopic data are consistent with those reported for the enantiomeric compound (−)-20. This can be converted into the known (3R,4S)-4-Aminopyrrolidin-3-ol Dihydrochloride Salt as follows: to a degassed solution of (+)-20 (155 mg, 0.418 mmol) in MeOH (5 mL) is added 21 mg of Pd/C (10%). The solution is stirred under an atmosphere of H$_2$ (g) at room temperature and

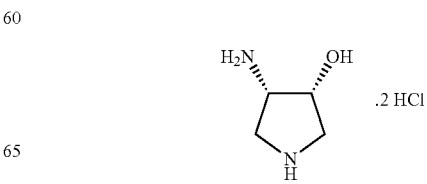

atmospheric pressure for 16 h. The solution is filtered through celite with ethyl acetate and concentrated. The residue is dissolved in MeOH (2 mL) and two drops of conc. HCl are added. The solution is concentrated to yield the (3R,4S)-4-Aminopyrrolidin-3-ol Dihydrochloride Salt as a white solid whose spectroscopic data is consistent with that reported in the literature. $[\alpha]^{21}_D=-12.2$ (c=0.58, H$_2$O); lit $[\alpha]^{20}_D=-23.9$ (c=1.12, H$_2$O) (Limberg, G.; Lundt, I.; Zavilla, J.; *Synthesis*, 1, 1999, 178-183);

(+)-(2R,3S)-Methyl 3-(ethoxycarbonylamino)-2-hydroxy-3-phenylpropanoate ((+)-21a). Following the general AA procedure above, methyl cinnamate (128 mg, 0.79

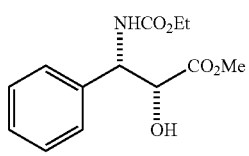

(+)-21a mmol) is reacted with osmium tetroxide (8 mg, 32 μmol), (DHQ)$_2$PHAL (31 mg, 0.039 mmol) and ethyl reagent 7 (269 mg, 1.10 mmol). Subsequent flash column chromatography (silica gel, petroleum spirit/ethyl acetate 6:1 and 3:1) affords (+)-21a as a white crystalline solid (85 mg, 40%) and 21a and 21b as a mixture (99 mg, 47%). The ratio of 21a:21b is determined to be 13:1 by HPLC. (+)-21a: M.p. (determined by differential scanning calorimetry, sharp onset); 89° C.; $[\alpha]^{23}_D$ +4.3 (c=1.85, CHCl$_3$); (Lit +2.78; c=0.9, EtOH (Shin, C.; Obara, T.; Morita, S.; Yonezawa, Y.; *Bull. Chem. Soc. Jpn.* 1988, 61, 3265-3272)); FTIR (neat, cm$^{-1}$) 3491, 3362, 2984, 1739, 1695, 1522, 1288, 1236, 1143, 1236, 1143, 1101, 1052, 1030, 766, 704, 682; $^1$H NMR (500 MHz, CDCl$_3$) δ 7.41-7.22 (m, 5H); 5.71 (d, J=8.1 Hz, 1H), 5.23 (d, J=9.0 Hz, 1H), 4.46 (br s, 1H), 4.07 (q, J=6.8 Hz, 2H), 3.81 (s, 3H), 3.48 (br s, 1H), 1.20 (t, J=6.8 Hz, 3H), $^{13}$C NMR (125 MHz, CDCl$_3$) δ 173.3, 156.0, 139.0, 128.6, 127.8, 126.7, 73.5, 61.2, 56.5, 53.0, 14.5; HRMS (ES+) m/z calcd for C$_{13}$H$_{17}$NO$_5$ (M+Na)$^+$ 290.0999, found 290.1005; Anal. calcd for C$_{13}$H$_{17}$NO$_5$: C, 58.42; H, 6.41; N, 5.24. Found C, 58.68; H, 6.46; N, 5.18.

(−)-(2S,3R)-Methyl 3-(ethoxycarbonylamino)-2-hydroxy-3-phenylpropanoate ((−)-21a). Following the general AA procedure above, methyl cinnamate (159 mg, 0.98 mmol) is reacted with osmium tetroxide (10 mg, 39 μmol), (DHQD)$_2$PHAL (38 mg, 49 mmol), and ethyl reagent 7 (335 mg, 1.38 mmol). Subsequent flash column

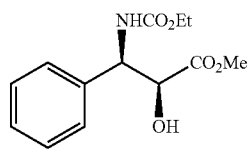

(−)-21a chromatography (silica gel, petroleum spirit/ethyl acetate 6:1 and 3:1) affords (−)-21a as a white crystalline solid (97 mg, 37%) and 21a and 21b as a mixture (94 mg, 36%). The ratio of 21a:21b is determined to 15:1 by HPLC. M.p. (determined by differential scanning calorimetry, sharp onset) 90° C.; $[\alpha]^{23}_D$ −4.9 (c=0.9, CHCl$_3$); HRMS (ES+) m/z calcd for C$_{13}$H$_{17}$NO$_5$ (M+Na)$^+$ 290.0999, found 290.1001; $^1$H and $^{13}$C NMR spectroscopic data is identical to that reported for (+)-21a above.

(±)-(2RS,3SR)-Methyl 3-(ethoxycarbonylamino)-2-hydroxy-3-phenylpropanoate ((±)-21a) and (±)-(2RS,3SR)-Methyl 2-(ethoxycarbonylamino)-3-hydroxy-3-phenylpropanoate ((±)-21 b).

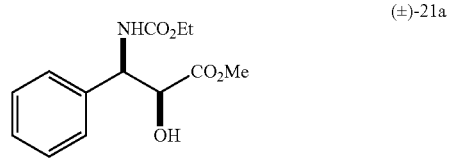

(±)-21a

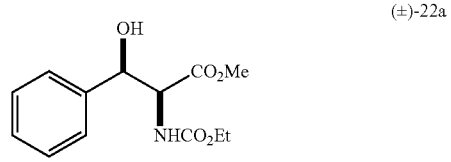

(±)-22a

Method A. Ethyl ethoxycarbonyloxycarbamate 54 (260 mg, 1.47 mmol), methyl cinnamate (170 mg, 1.05 mmol) and osmium tetroxide (11 mg, 0.04 mmol) are reacted for 72 h according to the general procedure. Subsequent flash column chromatography (silica gel, petroleum spirit/ethyl acetate 3:1) affords a mixture of (±)-21a and (±)-21b (230 mg, 82%). The overall ratio of a:b is determined to be 1:1.23 by HPLC.

Method B, the use of Os(III). Following the general procedure by using osmium(III) trichloride instead of osmium tetroxide, methyl cinnamate (150 mg, 0.93 mmol) is reacted with osmium(III) trichloride (11 mg, 0.04 mmol) and ethyl reagent 7 (315 mg, 1.30 mmol) for 16 h. Subsequent purification by flash column chromatography (silica gel, petroleum spirit/ethyl acetate 7:3) affords a mixture of (±)-21a and (±)-21b (247 mg, quantitative). The overall ratio of a:b is determined to be 1:1.16 by HPLC. NB-Vigorous bubbling is observed when the organic phases are washed with aqueous sat. NaHCO$_3$ solution.

(−)-(2R,3S)-Methyl 3-(benzyloxycarbonylamino)-2-hydroxy-3-phenylpropanoate ((−)-22a). Method A: Following the general AA procedure above, methyl cinnamate (128 mg, 0.79 mmol) is reacted with osmium tetroxide (8 mg, 32 μmol), (DHQ)$_2$PHAL (31 mg, 0.039 mmol) and benzyl reagent 8 (337 mg, 1.10 mmol) at 0° C. Subsequent flash

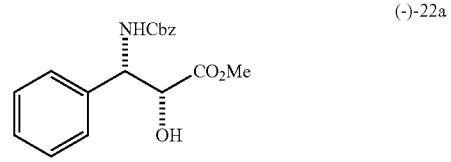 [SMILES: COC(=O)[C@H](O)[C@@H](NC(=O)OCc1ccccc1)c1ccccc1]

(−)-22a column chromatography (silica gel, petroleum spirit/ethyl acetate 6:1 and 3:1) affords (−)-22a as a white crystalline solid (159 mg, 61%); FTIR (neat, cm$^{-1}$) 3391, 1744, 1689, 1510, 1498, 1341, 1275, 1260, 1209, 1145, 1110, 1041, 1030, 987, 759, 749; M.p. (determined by differential scanning calorimetry, sharp onset) 120-121° C., {lit.[12] 120-121° C.}; $[\alpha]^{24}_D$ −1.29 (c=0.85, EtOH); {Lit. (+4.4; c=0.32, EtOH (Li, G.; Angert, H. H.; Sharpless, K. B. *Angew. Chem. Int. Ed. Engl.* 1996, 35, 2813-2817)), Lit (−3.79; c=1.0, CHCl$_3$ (Barycki, R.; Gumulku, M.; Masnyk, M.; Daniewski, W. M.; Kobus, M.; Luczak, M.; *Collect. Czech. Chem. Commun.* 67, 2002, 75-82))}; $^1$H NMR (500 MHz, CDCl$_3$) δ 7.43-7.05 (m, 10H); 5.65 (d, J=8.8 Hz, 1H), 5.27 (d, J=8.8 Hz, 1H), 5.13-

5.02 (m, 2H), 4.48 (s, 1H), 3.80 (s, 3H), 3.13 (d, J=3.5 Hz, 1H); $^{13}$C NMR (125 MHz, CDCl$_3$) δ 173.2; 155.7, 138.8, 136.3, 128.7, 128.5, 128.2, 128.1, 127.9, 126.7, 73.4, 67.0, 56.5, 53.1; (ES+) [M+Na]$^+$ 352 (100%); Anal. calcd for C$_{18}$H$_{19}$NO$_5$: C, 65.64; H, 5.81; N, 4.25. Found C, 65.56; H, 5.90; N, 4.21;

Method B: Following the general AA procedure above, methyl cinnamate (128 mg, 0.79 mmol) is reacted with osmium tetroxide (8 mg, 32 μmol), (DHQ)$_2$PHAL (31 mg, 0.039 mmol) and benzyl benzoyloxycarbamate (53, 299 mg, 1.10 mmol) at room temperature. Subsequent chromatography (silica gel, petroleum spirit/ethyl acetate 3:1 and 7:3) affords (−)-22a as a white solid (159 mg, 61%, 97% ee), 22b as a white solid (13 mg, 5%) and a mixture of (−)-22a and 22b (90 mg, 35%). The overall ratio of a:b is determined to be 5.94:1 by HPLC.

(+)-(2S,3R)-methyl 3-(benzyloxycarbonylamino)-2-hydroxy-3-phenylpropanoate ((+)-22a). Following the general AA procedure above, methyl cinnamate (128 mg, 0.79

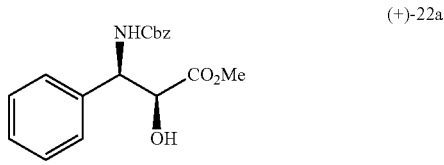 [SMILES: COC(=O)[C@@H](O)[C@H](NC(=O)OCc1ccccc1)c1ccccc1]

(+)-22a mmol) is reacted with osmium tetroxide (8 mg, 32 μmol), (DHQD)$_2$PHAL (31 mg, 0.039 mmol) and benzyl reagent 8 (337 mg, 1.10 mmol). Subsequent flash column chromatography (silica gel, petroleum spirit/ethyl acetate 6:1 and 3:1) affords (+)-22a as a white crystalline solid (152 mg, 59%); M.p. (determined by differential scanning calorimetry, sharp onset) 120-121° C.; [α]$^{21}_D$ +1.1 (c=1, EtOH); $^1$H and $^{13}$C NMR spectroscopic data is identical to that reported for (−)-22a above.

(±)-(2RS,3SR)-Methyl 3-(benzyloxycarbonylamino)-2-hydroxy-3-phenylpropanoate ((±)-22a) and (±)-(2RS,3SR)-Methyl 2-(benzyloxycarbonylamino)-3-hydroxy-3-phenylpropanoate ((±)-22b).

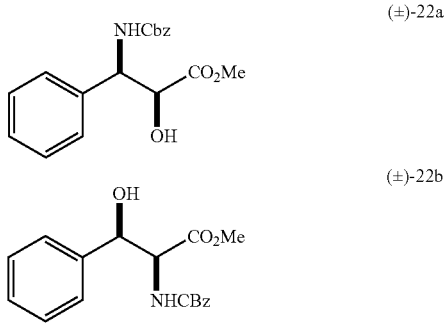

Method A: Benzyl benzoyloxycarbamate 53 (411 mg, 1.51 mmol), methyl cinnamate (175 mg, 1.08 mmol) and osmium tetroxide (11 mg, 0.04 mmol) are reacted according to the general procedure for 3 h. Subsequent flash column chromatography (silica gel, petroleum spirit/ethyl acetate 4:1 then 3:1) affords (±)-22a (95 mg, 27%), a mixture of (±)-22a and (±)-22b (111 mg, 31%) and (±)-22b (113 mg, 32%). The overall ratio of a:b is determined to be 1:1.25 by HPLC. The spectroscopic data of (±)-22a is identical to that reported for (−)-22a above.

22b: $^1$H NMR (500 MHz, CDCl$_3$) δ 7.33-7.18 (m, 10H), 5.75-5.65 (m, 1H), 5.22 (s, 1H), 4.94 (s, 2H) 4.57 (d, J=8.7 Hz, 1H), 3.69 (s, 3H), 3.26 (br s, 1H); $^{13}$C NMR (125 MHz, CDCl$_3$) δ 171.1, 156.3, 139.6, 136.1, 128.3, 128.3, 128.0, 127.8, 125.8, 66.9, 59.9, 52.5.

Method B: Benzyl benzyloxycarbonyloxycarbamate 52 (415 mg, 1.38 mmol), methyl cinnamate (159 mg, 0.98 mmol) and osmium tetroxide (10 mg, 0.04 mmol) are reacted for 72 h according to the general procedure. Subsequent flash column chromatorgraphy (silica gel, petroleum spirit/ethyl acetate 3:1 then 3:2) afforded 24 mg (7%) of (±)-22a and 159 mg (53%) of a mixture of (±)-22a and (±)-22b. The overall ratio of a:b is determined to be 1:1.23 by HPLC.

(−)-(2R,3S)-Methyl 3-(tert-Butoxycarbonylamino)-2-hydroxy-3-phenylpropanoate ((−)-23a).

Method A. Following the general AA procedure above, methyl cinnamate (128 mg, 0.79 mmol) is reacted with osmium tetroxide (8 mg, 32 μmol), (DHQ)$_2$PHAL (31 mg,

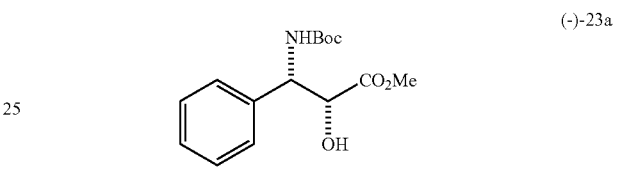

(−)-23a 0.039 mmol) and Boc-reagent 9 (300 mg, 1.10 mmol). Subsequent flash column chromatography (silica gel, petroleum spirit/ethyl acetate 9:1 and 16:3) affords 100 mg (43%) of (−)-23a as a white crystalline solid. M.p (determined by differential scanning calorimetry, sharp onset) 126° C. {lit. m.p. 129° C. (Kandula, S. R. V.; Pradeep, K.; Tet.: Asymm. 2005, 16, 3579-3583)}; [α]$^{23}_D$ −6.7 (c 0.85, CHCl$_3$) {lit. [α]$^{20}_D$ −7.3 (c 1.00, CHCl$_3$) (Lee, S.-H.; Yoon, J.; Chung, S.-H.; Lee, Y.-S.; Tetrahedron 2001, 2139-2145)}. HRMS (ES+) m/z calcd for C$_{15}$H$_{21}$N$_2$O$_5$ (2M+Na)$^+$ 318.312, found 318.1318. The spectroscopic data are consistent with those reported in the literature.

Method B, the use of Os(VI). (DHQ)$_2$PHAL (41 mg, 0.05 mmol) is suspended in acetonitrile (4 mL) and a few drops of water. Boc reagent 9 (399 mg, 1.47 mmol) is added to the mixture followed by a solution of potassium osmate (15 mg, 0.04 mmol) in water (1 mL). After stirring for 5 min, a solution of methyl cinnamate (170 mg, 1.05 mmol) in acetonitrile (4 mL) is added and the mixture is stirred for 3 h. Workup proceeds as outlined in the general procedure. Subsequent flash column chromatography (silica gel, petroleum spirit/ethyl acetate 4:1 and 3:1) affords of (−)-23a (131 mg, 42%, 94% ee), a mixture of (−)-23a and (−)-23b (21 mg, 7%) and a diol by-product (76 mg, 37%). The ratio a:b:diol is determined to be 5.61:1:3.79 by HPLC.

(+)-(2S,3R)-Methyl 3-(tert-Butoxycarbonylamino)-2-hydroxy-3-phenylpropanoate ((+)-23a).

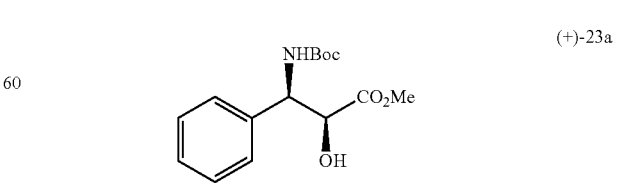

(+)-23a

Method A: Following the general AA procedure above, methyl cinnamate (128 mg, 0.79 mmol) is reacted with osmium tetroxide (8 mg, 32 μmol), (DHQD)₂PHAL (31 mg, 39 μmol) and Boc-reagent 9 (300 mg, 1.10 mmol). Subsequent flash column chromatography (silica gel, petroleum spirit/ethyl acetate 9:1 and 16:3) affords 107 mg (46%) of (+)-23a as a white crystalline solid. M.p. (determined by differential scanning calorimetry, sharp onset) 129° C.; [α]$_D^{23}$ +6.6 (c 0.8, CHCl₃) {Lit. [α]$_D^{20}$ +7.2 (c 0.22, CHCl₃) (Merino, P.; Castillo, E.; Franco, S.; *Tetrahedron*, 54, 1998, 12301-12322)}. HRMS (ES+) m/z calcd for C₁₅H₂₁NO₅ (M+Na)⁺ 318.1312, found 318.1318. Anal. calcd for C₁₅H₂₁NO₅: C, 61.00; H, 7.17; N, 4.74. Found C, 61.13; H, 7.39; N, 4.61; The spectroscopic data of (+)-23a are consistent with those reported for its antipode (−)-23a.

Furthermore, 16 mg (7%) of the regiomer and 38 mg (25%) diol by-product are isolated. The spectroscopic data of the diol ((2S,3R)-methyl 2,3-dihydroxy-3-phenylpropanoate) matched the data given in the literature [Carda, M; Murga, J.; Falomir, E.; Gonzalez, F.; Marco, J. A. *Tetrahedron*, 2000, 56, 677-683]. HRMS (ES+) m/z calcd for C₁₀H₁₂O₄ (M+Na)⁺ 219.0628, found 219.0632.

Method B: To a solution of (+)-26 (90 mg, 0.46 mmol) in MeOH (5 mL) is added di-tert-butyl dicarbonate (121 mg, 0.55 mmol). The mixture is stirred at room temperature overnight and concentrated. Subsequent flash column chromatography (silica gel, petroleum spirit/ethyl acetate 4:1) affords 95 mg (70%) of the title compound as a white solid. [α]$_D^{22}$ +6.5 (c 0.9, CHCl₃)

(±)-(2RS,3SR)-Methyl 3-(tert-Butoxycarbonylamino)-2-hydroxy-3-phenylpropanoate ((±)-23a) and (±)-(2RS,3SR)-Methyl 2-(tert-Butoxycarbonylamino)-3-hydroxy-3-phenylpropanoate ((±)-23b).

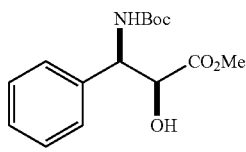
(±)-23a

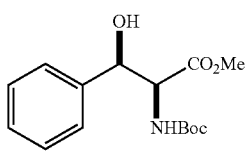
(±)-23b

Method A. tert-Butyl tert-butoxycarbonyloxycarbamate 55 (417 mg, 1.79 mmol), methyl cinnamate (207 mg, 1.28 mmol) and osmium tetroxide (13 mg, 0.05 mmol) are reacted for 72 h according to the general procedure. Subsequent flash column chromatography (silica gel, petroleum spirit/ethyl acetate 3:1) affords 230 mg (61%) of a mixture of (±)-23a and (±)-23b. The overall ratio of a:b is determined to be 1:1.64 by HPLC.

(+)-(2R,3S)-Methyl 3-(((9H-Fluoren-9-yl)methoxy)carbonylamino)-2-hydroxy-3-phenylpropanoate ((+)-24a). Following the general AA procedure above, methyl cinnamate (128 mg, 0.79 mmol) is reacted with osmium tetroxide (8 mg, 32 μmol), (DHQ)₂PHAL (31 mg, 39 μmol), and Fmoc reagent 10 (434 mg, 1.10 mmol). Subsequent flash column chromatography (silica gel, petroleum spirit/ethyl acetate 4:1)

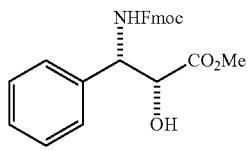
(+)-24a affords the title compound as a white solid (58 mg, 18%) and a mixture of the title compound and regioisomer (unisolated) (224 mg, 68%) (HPLC analysis reveals that the overall ratio a:b is 6.6:1). M.p. (determined by differential scanning calorimetry, sharp onset) 173° C.; FTIR (neat, cm⁻¹) 3371, 3342, 1724, 1693, 1542, 1310, 1289, 1263, 1219, 1176, 1143, 1104, 1085, 1030, 991, 976, 777, 755, 738, 702, 667; [α]$_D^{21}$ −8.0 (c=0.75, CHCl₃); ¹H NMR (500 MHz, CDCl₃) δ7.75 (d, J=6.9 Hz, 2H), 7.55 (d, J=6.9 Hz, 2H), 7.42-7.11 (m, ArH, 9H), 5.68 (d, J=9.1 Hz, 1H, HH), 5.28 (d, J=9.1 Hz, 1H, CH(NH)), 4.51 (s, 1H, CH(OH)), 4.45-4.26 (m, 2H, FlHCH₂O), 4.23-4.16 (m, 1H, FlHCH₂O); 3.82 (s, 3H, CH₃), 3.20 (br s, 1H, OH); ¹³C NMR (125 MHz, CDCl₃) δ 173.2, 155.7, 143.8, 141.3, 138.9, 128.7, 127.9, 127.7, 127.1, 126.7, 125.0, 120.0, 73.4, 67.0, 56.5, 53.2, 47.2; HRMS (ES+) m/z calcd for C₂₅H₂₃NO₅ (M+Na)⁺ 440.1468, found 440.1477.

(−)-(2S,3R)-Methyl 3-(((9H-Fluoren-9-yl)methoxy)carbonylamino)-2-hydroxy-3-phenylpropanoate ((−)-24a). Following the general AA procedure above using osmium

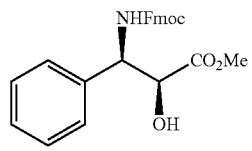
(−)-24a tetroxide (8 mg, 32 μmol), (DHQD)₂PHAL (31 mg, 39 μmol), methyl-trans-cinnamate (128 mg, 0.79 mmol) and Fmoc reagent 10 (434 mg, 1.10 mmol) and DCM as an eluent for column chromatography (approx 100 mL) then EtOAc/Petrol (1:4) yields the title compound as a white solid (58 mg, 18%) and a mixture of the title compound and regioisomer (unisolated) (255 mg, 76%) (HPLC analysis reveals that the overall ratio a:b is 5.6:1). [α]$_D^{21}$ −8.3 (c=1.16, CHCl₃); ¹H and ¹³C NMR data are identical to that for the antipode (+)-24a. M.p. (determined by differential scanning calorimetry, sharp onset) 161° C.; HRMS (ES+) m/z calcd for C₂₅H₂₃NO₅ (M+Na)⁺ 440.1468, found 440.1474.

Methyl 3-{[(9H-Fluoren-9-yl)methoxy]carbonylamino}-2-hydroxy-3-phenylpropanoate ((±)-24a) and Methyl 2-{[(9H-fluoren-9-yl)methoxy]carbonylamino}-3-hydroxy-3-phenylpropanoate ((±)-24b)

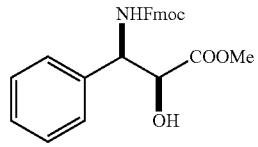
(±)-24a

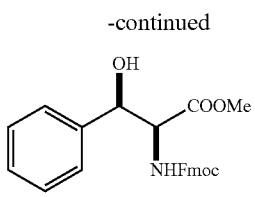

(±)-24b trans-Cinnamic acid (108 mg, 0.7 mmol) is reacted with osmium tetroxide (8 mg, 32 μmol) and Fmoc reagent 10 (399 mg, 1.0 mmol) for 7 h using the general AA procedure as described above. The crude product (0.52 g) is suspended in a 4:1 mixture of dichloromethane/methanol (5 ml) and methyl-esterified at room temperature with an excess of TMS-diazomethane. The resulting mixture is then concentrated and the residue analyzed by HPLC. The retention times of the regioisomeric adducts are consistent with those of (±)-24a and its regioisomer. The overall ratio of regioisomers is determined to be 1:1.2 from the achiral HPLC trace.

(4R,5S)-Methyl 2-Oxo-4-phenyloxazolidine-5-carboxylate ((+)-25). A mixture of (−)-12a (111 mg, 0.31 mmol) and lithium hydroxide monohydrate (64 mg, 1.55 mmol) in

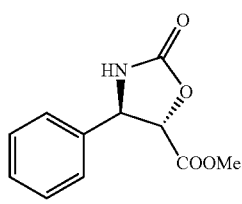

(+)-25 methanol (3.5 mL) is stirred for 10 min at room temperature. Water (1.5 mL) is added and the reaction mixture is stirred at room temperature for another 4 h before it is concentrated and ethyl acetate (5 mL) and water (5 mL) are added. The aqueous layer is separated and washed with ethyl acetate (5 mL). The organics are then discarded. Ethyl acetate (5 mL) is added to the aqueous layer and the biphasic mixture is stirred before 1M aqueous hydrochloric acid (5 mL, 5 mmol) is added. The organic phase is separated and the aqueous is extracted with ethyl acetate (3×10 mL). The combined organics are washed with brine and dried over MgSO$_4$ before being concentrated to dryness. The residue is taken up in THF (5 mL) and freshly prepared excess diazomethane (via Diazald) is distilled directly into the solution. The excess diazomethane is quenched by the dropwise addition of acetic acid and the mixture is concentrated. The crude reaction product is purified by flash column chromatography (silica gel, ethyl acetate/petroleum ether 4:1 and 1:1) to yield the title compound (+)-25 (38 mg, 55%) as a white crystalline solid. [α]$^{23}_D$ +74.8 (c 0.85, EtOH); FTIR (neat, cm$^{-1}$) 3264, 3168, 2922, 2852, 1761, 1722, 1458, 1435, 1385, 1376, 1318, 1301, 1279, 1228, 1211, 1190, 1155, 1093, 1076, 969, 933, 921, 914, 855, 821, 776, 760, 721, 700; $^1$H NMR (500 MHz; CDCl$_3$) δ 7.32-7.48 (m, 5H), 5.94 (s, 1H), 4.98 (d, J=5.1 Hz, 1H), 4.77 (d, J=5.1 Hz, 1H), 3.88 (s, 3H); $^{13}$C NMR (125 MHz; CDCl$_3$) δ 168.8, 157.6, 138.8, 129.4, 129.2, 125.9, 80.3, 59.1, 53.1; HRMS calcd for C$_{11}$H$_{11}$NO$_4$ (M+Na)$^+$ 244.0580, found 244.0581.

Method B: A mixture of (+)-22 (110 mg, 0.33 mmol) and lithium hydroxide monohydrate (64 mg, 1.55 mmol) in methanol (3.5 mL) is stirred for 10 min at room temperature. Water (1.5 mL) is added and the reaction is stirred at room temperature for 16 h. Following the remainder of Method 1 (above), the title compound (+)-25 (14 mg, 19%) is isolated as a white crystalline solid. [α]$^{16}_D$ +82.3 (c 0.6, EtOH). The spectroscopic data are consistent with those reported above.

(4S,5R)-Methyl 2-Oxo-4-phenyloxazolidine-5-carboxylate ((−)-25). Method A: (+)-12a (109 mg, 0.310 mmol) is subjected to the same reaction conditions used for the

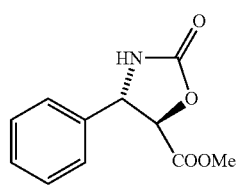

(−)-25 preparation of (+)-25 to give 34 mg (50%) of (−)-25 as a crystalline white solid. M.p. (determined by differential scanning calorimetry, slow onset) 152-153° C.; [α]$^{21}_D$ −68.8 (c 0.9, EtOH); $^1$H NMR (500 MHz; CDCl$_3$) δ 7.32-7.45 (m, 5H) 6.25 (s, 1H), 4.98 (d, J=5.1 Hz, 1H), 4.76 (d, J=5.1 Hz, 1H), 3.87 (s, 3H); $^{13}$C NMR (126 MHz; CDCl$_3$) δ 168.8 157.8, 138.9, 129.3, 129.1, 125.9, 80.3, 59.1, 53.1; HRMS calcd for C$_{11}$H$_{11}$NO$_4$ (M+Na)$^+$ 244.0580, found 244.0585.

(+)-(2S,3R)-Methyl 3-Amino-2-hydroxy-3-phenylpropanoate ((+)-26) To a degassed solution of (+)-22a (152 mg, 0.461 mmol) in MeOH (5 mL) is added 30 mg of Pd/C (10%).

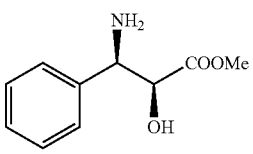

(+)-26

The solution is stirred under an atmosphere of H$_2$ (g) at atmospheric pressure for 16 h. The solution is filtered through celite with ethyl acetate and concentrated to give (+)-26 (90 mg, quantitative) as a white solid. The spectroscopic data is consistent with that reported in the literature. [α]$^{20}_D$=+22.1 (c=1.0, MeOH); lit [α]$^{20}_D$=+30 (c=1.0, MeOH) (Qi, C.-M.; Wangm Y.-F.; Yang, L.-C.; J. Hetero. Chem., 42, 2005, 679-684); The enantiomer ((−)-26) is also synthesized from (−)-22a by the same method; [α]$^{20}_D$=−22.1 (c=1.0, MeOH); lit [α]$^{20}_D$=−22 (c=1.0, MeOH) (Qi, C.-M.; Wangm Y.-F.; Yang, L.-C.; J. Hetero. Chem., 42, 2005, 679-684).

Benzyl 3-(diethoxyphosphoryl)-2-hydroxypropylcarbamate (27a) and benzyl 1-(diethoxyphosphoryl)-3-hydroxypropan-2-ylcarbamate (27b).

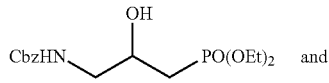

27a and

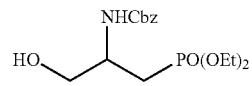

27b

Method A: Following the general AA procedure above, diethyl allylphosphonate (300 mg, 1.64 mmol) is reacted with osmium tetroxide (17 mg, 67 μmol), (DHQ)$_2$PHAL (66 mg, 84 mmol), and benzyl reagent 8 (721 mg, 2.36 mmol). Subsequent flash column chromatography (silica gel, petroleum spirit/ethyl acetate 3:7 and 0:1) gives 27a (275 mg, 47%) as a light-brown oil, 27b (20 mg, 3%) as a light-brown oil and a mixture of 27a and 27b (30 mg, 5%). Method B: Following the general AA procedure above, diethyl allylphosphonate (300 mg, 1.64 mmol) is reacted with osmium tetroxide (17 mg, 67 µmol), (DHQD)$_2$PHAL (66 mg, 84 mmol) and benzyl reagent 8 (721 mg, 2.36 mmol). Subsequent flash column chromatography (silica gel, petroleum spirit/ethyl acetate 3:7 and 0:1) gives 27a (284 mg, 49%) as a light-brown oil, 27b (3 mg, <1%) as a light-brown oil and a mixture of 27a and 27b (55 mg, 9%).

27a. FTIR (neat, cm$^{-1}$) 3323, 2983, 2932, 1702, 1536, 1456, 1393, 1216, 1162, 1144, 1096, 1021, 962, 878, 835, 775, 738, 697; $^1$H NMR (300 MHz, CDCl$_3$) δ 7.36-7.27 (m, 5H), 5.52 (br m, 1H, NH), 5.10 (s, 2H), 4.19-4.00 (m, 6H), 3.48-3.33 (m, 1H), 1.93 (dd, J=6.5, 17.9 Hz, 2H), 1.31, 1.31 (2×t, J=7.1, 7.1 Hz respectively, 6H); $^{13}$C NMR (75 MHz, CDCl$_3$) δ 156.9, 136.4, 128.4, 128.0. 128.0, 66.8, 65.9, 62.0 (br), (47.0, 47.3), 30.8 (d, J=139.9 Hz), (16.3, 16.3); HRMS (ES+) m/z calcd for C$_{15}$H$_{24}$NO$_6$P (M+Na)$^+$ 368.1233, found 368.1234.

27b. $^1$H NMR (300 MHz, CDCl$_3$) δ 7.39-7.27 (m, 5H), 5.73 (d, J=6.0 Hz), 5.09 (s, 2H), 4.14-3.96 (m, 5H), 3.85-3.76 (m br, 1H), 3.75-3.64 (m, 2H), 2.24-1.97 (m, 2H), 1.33-1.24 (m, 6H); $^{13}$C NMR (75 MHz, CDCl$_3$) δ 156.0, 136.4, 128.4, 128.1, 128.0, 66.7, (64.4, 64.4), 62.1 (br), 48.4, 27.7 (d, J=138.6 Hz), (16.3, 16.3). HRMS (ES+) m/z calcd for C$_{15}$H$_{24}$NO$_6$P (M+Na)$^+$ 368.1233, found 368.1235.

(9H-Fluoren-9-yl)methyl 3-(diethoxyphosphoryl)-2-hydroxypropylcarbamate (28a) and (9H-fluoren-9-yl)methyl 1-(diethoxyphosphoryl)-3-hydroxypropan-2-ylcarbamate (28b). Following the general AA procedure above, diethyl

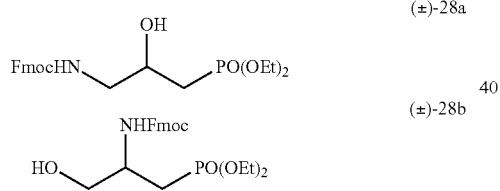

allylphosphonate (500 mg, 2.81 mmol) is reacted with osmium tetroxide (25 mg, 98 µmol) and Fmoc reagent 10 (1492 mg, 3.79 mmol). Subsequent flash column chromatography (silica gel, ethyl acetate/petroleum ether 1:1 and 1:0) gives 28a and 28b (972 mg, 80%) as viscous oils. Analytical samples of 28a and 28b are obtained.

28a. FTIR (neat, cm$^{-1}$) 3327, 3066, 2982, 2931, 2907, 1704, 1535, 1478, 1450, 1393, 1368, 1320, 1243, 1151, 1097, 1022, 962, 885, 834, 815, 759, 740; $^1$H NMR (500 MHz, CDCl$_3$) δ 7.77 (d, J=7.5 Hz, 2H), 7.59 (d, J=7.5 Hz, 2H), 7.39 (t, J=7.4 Hz, 2H), 7.30 (td, J=1.0, 7.5 Hz, 2H), 5.43 (t, J=5.3, 1H, NH), 4.39 (d, J=7.0 Hz, 2H), 4.21 (t, J=7.0 Hz, 1H), 4.07-4.18 (m, 5H), 4.06 (br s, 1H, OH), 3.40-3.50 (br m, 1H), 3.18-3.50 (br, m, 1H), 1.94 (dd, J=6.2, 17.6 Hz, 2H), 1.33, 1.34 (2×t, J=7.1, 7.1 Hz respectively, 6H); $^{13}$C NMR (125 MHz, CDCl$_3$) δ 157.0, 143.9, 141.3, 127.7, 127.1, 125.1, 120.0, 66.9, 66.0, (62.1, 62.1), 47.3, (47.0, 47.2), 30.8 (d, J=140.0 Hz), 16.4 (t, J=5.7 Hz); HRMS (ES+) m/z calcd for C$_{22}$H$_{28}$NO$_6$P (M+Na)$^+$ 456.1546, found 456.1548.

28b. FTIR (neat, cm$^{-1}$) 3322, 3068, 2982, 2930, 1702, 1537, 1478, 1450, 1394, 1369, 1320, 1223, 1163, 1139, 1020, 965, 910, 837, 759, 738; $^1$H NMR (500 MHz, CDCl$_3$) δ7.74 (d, J=7.6 Hz, 2H), 7.59 (d, J=7.5 Hz, 2H), 7.38 (t, J=7.5 Hz, 2H), 7.30 (t, J=7.5 Hz, 2H), 5.77 (d, J=6.9 Hz, 1H), 4.42-4.34 (m, 2H), 4.20 (t, J=6.8 Hz, 1H) 3.95-4.14 (m, 6H), 3.83 (d, J=10.4 Hz, 1H), 3.71 (d, J=10.4 Hz, 1H), 2.05-2.25 (m, 2H), 1.25-1.33 (m, 6H); $^{13}$C NMR (125 MHz, CDCl$_3$) δ 156.1, (143.9, 143.9), 141.3, 127.7, 127.1, 125.1, 120.0, 66.9, (64.4, 64.4), (62.2, 62.1), 48.7, 47.2, 27.7 (d, J=138.6 Hz), 16.4 (d, J=5.9 Hz). HRMS (ES+) m/z calcd for C$_{22}$H$_{28}$NO$_6$P (M+Na)$^+$ 456.1546, found 456.1547.

(±)-(9H-Fluoren-9-yl)methyl (1S,2S)-2-Hydroxy-3-oxocyclohexylcarbamate (29).

Following the general procedure, 2-cyclohexenone (76 mg, 0.79 mmol) is reacted with osmium tetroxide (8 mg, 0.03 mmol) and Fmoc reagent 10 (436 mg, 1.11 mmol) for 16

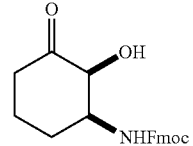

h. Subsequent flash column chromatography (silica gel, CH$_2$Cl$_2$ then petroleum spirit/ethyl acetate 1:1) affords the title compound as a colourless solid (193 mg, 70%). $^1$H (500 MHz, CDCl$_3$) δ 7.74 (d, J=7.5 Hz, 2H), 7.57-7.54 (m, 2H), 7.38 (t, J=7.5 Hz, 2H), 7.32-7.28 (m, 2H), 4.75 (d, J=4.0 Hz, 1H), 4.43-4.35 (m, 3H), 4.26 (d, J=5.0 Hz, 1H), 4.19 (t, J=6.8, 1H), 3.73 (s, 1H), 2.60-2.50 (m, 1H), 2.44-2.26 (m, 2H), 1.97-1.74 (3H, m); $^{13}$C NMR (125 MHz, CDCl$_3$) δ 210.1, 156.3, 143.9, 143.8, 141.3, 127.0, 125.0, 119.9, 75.7, 66.8, 63.4, 55.4, 47.2, 39.0, 27.3, 21.3; HRMS (ES+) m/z calcd for C$_{21}$H$_{21}$NO$_4$Na$^+$ 374.1363, found 374.1371.

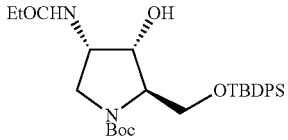

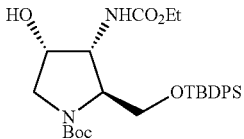

(2R,3S,4S)-tert-Butyl 2-[(tert-Butyldiphenylsilyloxy)methyl]-4-(ethoxycarbonylamino)-3-hydroxy pyrrolidine-1-carboxylate (31) and (2S,3R,4S)-tert-butyl 2-[(tert-butyldiphenylsilyloxy)methyl]-3-(ethoxycarbonylamino)-4-hydroxypyrrolidine-1-carboxylate (32). Osmium tetroxide (19.3 mg, 76.2 µmol) is added to a solution of ethyl 4-chlorobenzoyloxycarbamate 7 (697 mg, 2.86 mmol) in tert-BuOH (8 mL) and stirred at room temperature for 10 minutes. (S)-30 (834 mg, 1.90 mmol) dissolved in tert-BuOH (10 mL) is added to the carbamate solution followed by the addition of water (6 mL) and the reaction is stirred at room temperature for 3 h. The reaction is quenched by adding saturated K$_2$S$_2$O$_5$ solution (20 mL) and stirring for 15 minutes. Ethyl acetate (200 mL) is added to the reaction solution, then it is washed with water (100 mL), dried over MgSO$_4$ and the solvent removed under reduced pressure. The residue is purified by flash column chromatography (silica gel, ethyl acetate/petroleum ether 3:7) to yield 31 (130 mg, 13%) and 32 (290 mg, 27%) as off-white foams, and a 1:1 mixture of 31 and 32 (420 mg, 41%). The total yield is 81%.

32: M.p. 49-51° C. (foam); [α]$^{21}_D$ −27.4 (c 1.04, CHCl$_3$); FTIR (film, cm$^{-1}$) 3384, 2932, 2859, 1696, 1674, 1590, 1514, 1473, 1427, 1408, 1367, 1324, 1255, 1162, 1140, 1106, 1052, 1007, 970, 938, 918, 862, 823, 774, 741, 701, 666; $^1$H NMR (500 MHz, DMSO-d$_6$, rotamers) ☐ δ 7.66-7.57 (m, 4H), 7.50-7.36 (m, 6H), 7.01-6.95 (m, 1H), 5.19 (s$_{br}$, 1H), 4:47-4.34 (m, 1H), 4.27-3.94 (m, 4H), 3.65-3.47 (m, 3H), 3.41-3.23 (m 1H), 2.52-2.50 (m, 1H), 1.45-1.40 (m, 4H), 1.26-1.17 (m, 8H), 1.02-0.95 (m, 9H); $^{13}$C NMR (125 MHz, DMSO-d$_6$, rotamers) δ 156.04, 153.70, 135.02, 134.97, 132.92, 132.79, 129.77, 127.85, 127.80, 127.72, 78.35, 78.25, 67.72, 67.42, 61.33, 60.21, 60.04, 59.89, 59.75, 55.30, 54.45, 53.99, 53.33, 28.15, 27.90, 26.49, 26.39, 18.79, 14.62; $^1$H NMR (500 MHz, DMSO-d$_6$, 100° C.) ☐ δ 7.67-7.61 (m, 4H), 4.48-7.38 (m, 6H), 6.44 (d$_{br}$, J=7.5 Hz, 1H), 4.89 (d, J=4.2 Hz, 1H), 4.14-4.36 (m, 1H), 4.23-4.01 (m, 4H), 3.71 (d, J=9.9 Hz, 1H), 3.65-3.60 (m, 1H), 3.54 (dd, J=2.2 Hz, 11.7 Hz, 1H), 3.42-3.27 (m, 1H), 1.36 (s$_{br}$, 9H), 1.21 (t, J=7.1 Hz, 3H), 1.03 (s, 9H); $^{13}$C NMR (125 MHz, DMSO-d$_6$, 100° C.) δ 155.93, 153.83, 135.06, 135.02, 133.32, 129.57, 127.59, 78.39, 67.91, 61.26, 59.81, 55.31, 53.48, 28.14, 26.62, 18.81, 14.44; HRMS (ES+) m/z calcd for C$_{29}$H$_{42}$N$_2$O$_6$SiNa$^+$ 565.2710, found 565.2704.

31: M.p. 47-49° C. (foam); [α]$^{21}_D$ −23.5 (c 1.62, CHCl$_3$); FTIR (film, cm$^{-1}$) 3382, 3071, 2932, 2859, 1695, 1673, 1590, 1513, 1473, 1427, 1392, 1367, 1325, 1253, 1170, 1136, 1112, 1049, 998, 973, 937, 873, 857, 822, 812, 776, 739, 701; $^1$H NMR (500 MHz, DMSO-d$_6$, rotamers) ☐ δ 7.65-7.57 (m, 4H), 7.50-7.38 (m, 6H), 6.86 (d$_{br}$, 6.7 Hz, 0.5H), 6.77 (d$_{br}$, J=6.7 Hz, 0.5H), 5.37-5.27 (m, 1H), 4.39-4.26 (m, 1H), 4.24 (s$_{br}$, 0.5H), 4.18 (s$_{br}$, 0.5H), 4.07-3.97 (m, 2H), 3.83-3.74 (m, 0.5H), 3.74-3.58 (m, 2.5H), 3.50 (t$_{br}$, J=9.2 Hz, 0.5H), 3.42 (t$_{br}$, J=9.2 Hz, 0.5H), 3.18 (q, J=9.6 Hz, 1H), 1.40 (s, 4.5H), 1.24 (s, 4.5H), 1.21-1.14 (m, 3H), 1.03-0.98 (m, 9H); $^{13}$C NMR (125 MHz, DMSO-d$_6$, rotamers) δ 155.83, 153.68, 153.39, 134.99, 132.80, 132.73, 132.63, 132.60, 132.54, 129.85, 127.87, 127.79, 78.51, 78.43, 71.52, 71.21, 66.24, 66.03, 62.91, 62.28, 59.72, 52.01, 51.29, 48.35, 47.80, 28.10, 27.91, 26.52, 18.72, 14.59; $^1$H NMR (500 MHz, DMSO-d$_6$, 100° C.) ☐ δ 7.66-7.61 (m, 4H), 7.49-7.39 (m, 6H), 6.25 (d$_{br}$, J=4.1 Hz, 1H), 5.05 (d, J=4.6 Hz, 1H), 4.33-4.22 (m, 2H), 4.05 (q, J=7.2 Hz, 2H), 3.81-3.70 (m, 3H), 3.56-3.49 (m, 1H), 1.36 (s$_{br}$, 9H), 1.20 (t, J=7.1 Hz, 3H), 1.05 (s, 9H); $^{13}$C NMR (125 MHz, DMSO-d$_6$, 100° C.) δ 155.73, 153.69, 135.01, 133.19, 133.05, 129.68, 127.71, 127.69, 78.55, 71.81, 66.22, 62.94, 59.84, 51.83, 48.74, 28.11, 26.68, 18.75, 14.43; HRMS (ES+) m/z calcd for C$_{29}$H$_{42}$N$_2$O$_6$SiNa$^+$ 565.2710, found 565.2714; Anal. calcd for C$_{29}$H$_{42}$N$_2$O$_6$Si: C, 64.18; H, 7.80; N, 5.16. Found C, 64.37; H, 7.73; N, 4.96.

(2R,3S,4S)-tert-butyl 4-(benzyloxycarbonylamino)-2-[(tert-butyldiphenylsilyloxy) methyl]-3-hydroxypyrrolidine-1-carboxylate (33) and (2S,3R,4S)-tert-butyl 3-(benzyloxycarbonylamino)-2-[(tert-butyldiphenylsilyloxy) methyl]-4-hydroxypyrrolidine-1-carboxylate (34).

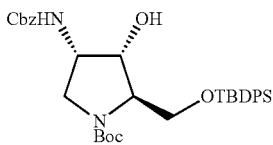

33

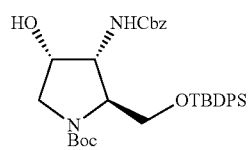

34

Method 1: According to the general AA procedure outlined above 30 (250 mg, 0.57 mmol) is treated with osmium tetroxide (7 mg, 28 μmol) and benzyl reagent 8 (305 mg, 1.00 mmol). Upon flash column chromatography (silica gel, ethyl acetate/petroleum ether 1:9 and 3:7) compounds 33 (60 mg, 17%), 34 (60 mg, 17%) and a mixture of the two regioisomers 33 and 34 (100 mg, 29%) are isolated. Overall the reaction proceeds in 64% yield and both regioisomers are formed in a 1:1.6 ratio as determined by HPLC analysis.

33: [α]$^{23}_D$ −19.9 (c 0.82, CHCl$_3$); $^1$H NMR (500 MHz, DMSO-d$_6$, rotamers) δ 1.01 (s$_{br}$, 9H), 1.24 (s, 4.5H), 1.40 (s, 4.5H), 3.20 (q, J=10.1 Hz, 1H), 3.43 (t, J=8.8 Hz, 0.5H), 3.51 (t, J=8.8 Hz, 0.5H), 3.59-3.73 (m, 1.5H), 3.79 (dd, 4.7, 9.8 Hz, 0.5H), 4.20 (s$_{br}$, 0.5H), 4.26 (s$_{br}$, 0.5H), 4.29-4.42 (m, 1H), 4.97-5.10 (m, 2H), 5.27-5.43 (m$_{br}$, 1H), 7.02 (d, J=7.3 Hz, 0.5H), 7.09 (d, J=7.3 Hz, 0.5H), 7.21-7.51 (m, 11H), 7.52-7.68 (m, 4H); $^{13}$C NMR (125 MHz, DMSO-d$_6$, rotamers) δ 18.63, 26.43, 27.82, 28.00, 47.66, 48.22, 51.35, 52.06, 62.16, 62.80, 65.32, 65.91, 66.14, 71.09, 71.40, 78.36, 78.43, 127, 65 (sh), 127.71 (sh), 127.78, 128.19, 129.75, 132.46, 132.53, 132.64, 132.70, 134.89, 136.92, 153.30, 153.57, 155.62; $^1$H NMR (500 MHz, DMSO-d$_6$, 100° C.) δ 1.02 (s, 9H), 3.21 (t, J=9.7 Hz, 1H), 3.51 (dd, J=9.7, 8.4 Hz, 1H), 3.64-3.79 (m, 3H), 4.24 (s$_{br}$, 1H), 4.27-4.34 (m, 1H), 5.06 (m, 3H), 6.48 (s$_{br}$, 1H, NH), 7.26-7.46 (m, 11H, ArH), 7.58-7.64 (m, 4H, ArH); $^{13}$C NMR (125 MHz, DMSO-d$_6$, 100° C.) δ 18.19, 26.13, 27.56, 48. 16, 51.44, 62.35 (broad), 65.03, 65.65, 71.22, 78.01, 126.97, 127.06, 127.15 (broad), 127.64, 129.11, 132.50, 132.63, 134.45, 136.55, 153.13, 155.08; HRMS (ES+) m/z calc for C$_{34}$H$_{44}$N$_2$O$_6$SiNa$^+$ 627.2861, found 627.2867.

34: [α]$^{23}_D$ −20.8 (c 1.06, CHCl$_3$); $^1$H NMR (500 MHz, DMSO-d$_6$, rotamers) δ 0.96 (s, 4.5H), 0.99 (s, 4.5H), 1.22 (s, 4.5H), 1.42 (s, 4.5H), 3.22-3.37 (m, 1H), 3.47-3.63 (m, 3H), 3.96 (dd, J=2.8, 10.1 Hz, 0.5H), 4.14 (s$_{br}$, 1H), 4.19-4.25 (m, 0.5H), 4.35-4.48 (m, 1H), 5.06 (d, J=12.7 Hz, 1H), 5.13 (d, J=12.7 Hz, 1H), 5.22 (s$_{br}$, 1H), 7.20 (t, J=8.9 Hz, 1H), 7.27-7.49 (m, 11H), 7.54-7.67 (m, 4H); $^{13}$C NMR (125 MHz, DMSO-d$_6$, rotamers) δ 18.67, 26.29, 26.38, 27.79, 28.04, 53.19, 53.86, 54.49, 55.31, 59.80, 59.96, 60.17, 61.23, 65.28, 67.29, 67.58, 78.16, 78.26, 127.64 (broad), 128.18, 129.61, 129.69 (sh), (132.66, 132.75), 134.88 (broad), 136.97, 153.59, 155.87; $^1$H NMR (500 MHz, DMSO-d$_6$, 100° C.) δ 1.00 (s, 9H), 3.32 (dd, J=3.6, 11.4 Hz, 1H), 3.51 (dd, J=2.3, 11.4 Hz, 1H), 3.61-3.65 (m, 1H), 3.68 (d, J=10.1 Hz, 1H), 4.07 (s$_{br}$, 1H), 4.16-4.21 (m, 1H), 4.39 (td, J=4.6, 7.5 Hz, 1H), 4.89 (d, J=3.7 Hz, 1H), 5.05 (d, J=12.8 Hz, 1H), 5.10 (d, J=12.8 Hz, 1H), 6.66 (d, J=7.4 Hz, 1H), 7.25-7.45 (m, 11H), 7.57-7.63 (m, 4H); $^{13}$C NMR (125 MHz, DMSO-d$_6$, 100° C.) δ 18.24, 26.06, 27.57, 52.88, 54.91, 60.71, 65.00, 67.33, 77.84, 126.96, 127.04 (broad), 127.62, 129.00, 132.73, (134.45), 134.47, 136.59, 153.26, 155.28; HRMS (ES+) m/z calc for C$_{34}$H$_{44}$N$_2$O$_6$SiNa$^+$ 627.2861, found 627.2869.

Method 2: Following the general AA procedure 30 (312 mg, 0.71 mmol) is reacted with osmium tetroxide (7.25 mg, 28.5 μmol) and the benzyl reagent 8 (305 mg, 1.00 mmol) in the presence of (DHQ)$_2$PHAL (28 mg, 0.36 mmol) to give a 1:2.2 mixture of regioisomers (as determined by HPLC analysis) with 34 as the major compound.

Method 3: Following the general AA procedure 30 (302 mg, 0.69 mmol) is treated with osmium tetroxide (7 mg, 28 μmol) and benzyl reagent 8 (295 mg, 0.97 mmol) in the presence of (DHQD)$_2$PHAL (27 mg, 0.35 mmol) to provide a 1.5:1 mixture of regioisomers (by HPLC analysis) with 33 as the major compound.

Ethyl (3S,6S,7S,7aR)-6-hydroxy-5-oxo-3-phenylhexahydropyrrolo[1,2-c]oxazol-7-ylcarbamate (36). Osmium tetroxide (69 mg, 0.27 mmol) is added to a solution of ethyl 4-chlorobenzoyloxycarbamate 7 (2.31 g, 9.52 mmol) in acetonitrile (30 mL) and stirred

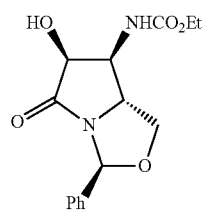

36 at room Temperature for 10 min. A solution of 35 (1.37 g, 6.80 mol) in acetonitrile (30.5 mL) is introduced to the carbamate solution followed by the addition of water (7.5 mL) and the reaction is stirred at room temperature for 26 h. The work-up is carried out according to the general procedure and the residue is purified by flash column chromatography (silica gel, ethyl acetate/petroleum ether 3:7) to yield 36 and its regioisomer in a ratio of 9:1 (33 g, 74%). Analytical samples are obtained. M.p. 176-178° C. (crystallized from dichloromethane/petroleum spirit); [α]$^{21}_D$ −126 (c 0.73, CHCl$_3$); FTIR (neat, cm$^{-1}$) 3310, 3059, 2971, 2937, 2896, 1685, 1531, 1497, 1478, 1449, 1390, 1376, 1357, 1328, 1310, 1254, 1215, 1176, 1165, 1126, 1099, 1063, 1023, 932, 923, 905, 886, 861, 800, 781, 764, 737, 700, 666; $^1$H NMR (500 MHz, CDCl$_3$) □ δ 7.43-7.39 (m, 2H), 7.37-7.31 (m, 3H), 6.25 (s, 1H), 5.69 (d$_{br}$, J=5.6 Hz, 1H), 4.74 (s, 1H), 4.48-4.34 (m, 2H), 4.19-4.04 (m, 4H), 3.96-3.87 (m$_{br}$, 1H), 1.68 (s, 1H), 1.25 (t, J=7.0 Hz, 3H); $^{13}$C NMR (125 MHz, CDCl$_3$) δ 173.87, 156.45, 137.27, 128.96, 128.58, 126.06, 86.48, 74.78, 71.11, 65.06, 61.43, 54.09, 14.53; HRMS (ES+) m/z calcd for C$_{15}$H$_{18}$N$_2$O$_5$Na$^+$ 329.1113, found 329.1116.

Ethyl (3R,6R,7R,7aS)-6-Hydroxy-5-oxo-3-phenylhexahydropyrrolo[1,2-c]oxazol-7-yl Carbamate (38). A solution of α,β-unsaturated bicyclic lactam 37 (4.00 g, 19.9 mmol) in dry tert-BuOH (150 mL) is reacted with a solution of ethyl reagent 7 (6.63 g,

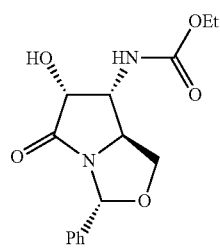

38

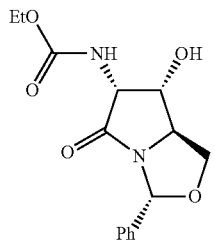

39

27.9 mmol) and OsO$_4$ (200 mg, 0.800 mmol) in tert-BuOh (150 mL) and water (49 mL) at room temperature for 7 h to yield 38 (2.02 g, 33%) as a white solid, after chromatography. In addition, 2.34 g of unreacted carbamate (7) are recovered. The spectroscopic data of 38 are consistent with those reported for the enantiomer (above). Furthermore, continued elution provides a small amount of 250 mg of a putatively isomeric compound 39 which is recrystallized from ethyl acetate/hexane to give fine colorless needles.

39: M.p. 141-142° C.; [α]$^{18}_D$ +188 (c 0.415, CHCl$_3$); FTIR (cm$^{-1}$) 3346, 3298, 1710, 1672, 1547, 14.01, 1322, 1256, 1063, 927, 739, 696; $^1$H NMR (500 MHz, CDCl$_3$) δ7.44-7.33 (m, 5H), 6.32 (s, 1H), 5.44 (d, J=6.8 Hz, 1H), 4.46 (t, J=6.8 Hz, 1H), 4.39 (m, 1H), 4.29 (dd, J=8.4, 6.9 Hz, 1H), 4.21-4.10 (m, 2H), 4.02 (ddd, J=9.0, 6.8, 2.3 Hz, 1H), 3.56 (t, J=8.7 Hz, 1H), 3.22 (s$_{br}$, 1H), 1.25 (t, J=6.0 Hz, 3H). $^{13}$C NMR (125 MHz, CDCl$_3$) δ 174.50, 137.77, 128.61, 128.52, 125.88, 88.12, 67.73, 67.45, 64.84, 62.11, 58.16, 14.42. HRMS (ESI) m/z calc for C$_{15}$H$_{18}$N$_2$O$_5$Na$^+$ 329.1113, found 329.1108.

(2S,3R,4R)-tert-Butyl 3-(Benzyloxycarbonylamino)-2-[(tert-butyldiphenylsilyl-oxy)methyl]-4-hydroxy-5-oxopyrrolidine-1-carboxylate (41). Lactam 40 (500 mg, 1.11 mmol) dissolved in tert-BuOH (5 mL) is treated with osmium tetroxide (11.3 mg, 44.3 μmol) and benzyl reagent 8 (474 mg, 1.55 mmol) in tert-BuOH (5 mL) and water

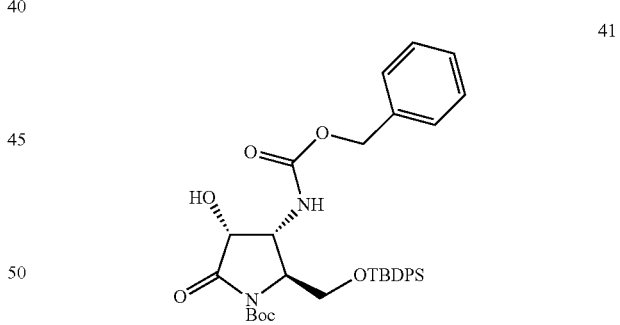

41

(1.7 mL) using the same procedure as described for the preparation of (±)-11a and (±)-11b (above) to yield 41 (475 mg, 75%) as a colorless foam. [α]$^{20}_D$ −24.3 (c 1.10, CHCl$_3$); FTIR (neat, cm$^{-1}$) 3399 (OH), 3072, 2932, 2859, 1787, 1719 (C=O), 1497, 1472, 1428, 1368, 1295, 1251, 1151, 1111, 1075, 996, 963, 845, 822, 776, 742, 700; $^1$H NMR (500 MHz, CDCl$_3$) δ 7.61-7.57 (m, 2H), 7.55-7.51 (m, 2H), 7.47-7.30 (m, 11H), 5.67 (br s, 1H), 5.13 (d, J=12.2 Hz, 1H), 5.08 (d, J=12.2 Hz, 1H), 4.92 (d, J=7.0 Hz, 1H), 4.35 (dd, J=7.1, 2.5 Hz, 1H), 4.27 (s$_{br}$, 1H), 3.97 (dd, J=17.4, 10.7 Hz, 2H), 3.16 (s, 1H), 1.42 (s, 9H), 1.02 (s, 9H); HRMS (ES+) m/z calcd for C$_{34}$H$_{42}$N$_2$O$_7$SiNa$^+$ 641.2659, found 641.2663; Anal. calcd for C$_{34}$H$_{42}$N$_2$O$_7$Si: C, 65.99; H, 6.84; N, 4.53. Found C, 66.16; H, 7.12; N, 4.44.

(2R,3S,4S)-tert-Butyl 3-(Benzyloxycarbonylamino)-2-[(tert-butyldiphenylsilyl-oxy)methyl]-4-hydroxy-5-oxopyrrolidine-1-carboxylate (43). Lactam 42 (500 mg, 1.11 mmol) dissolved in tert-BuOH (5 mL) is treated with osmium tetroxide (28.1 mg, 0.111 mmol) and benzyl 4-chlorobenzoyloxycarbamate 8 (474 mg, 1.55 mmol) in tert-BuOH

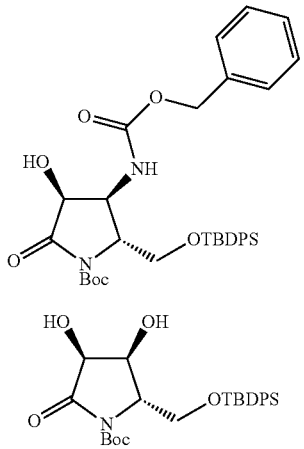

(5 mL) and water (1.7 mL) using the same procedure as described for the preparation of (±)-11a and (±)-11b (above) to yield 43 (398 mg, 58%) as a colorless foam. $[\alpha]^{19}_D$=+24.6 (c 1.28, CHCl$_3$) {enantiomer: $[\alpha]^{18}_D$=−24.3 (c 1.10, CHCl$_3$)}. The spectroscopic data of 43 are consistent with those recorded for the enantiomeric compound (above). In addition, 44 (151 mg, 28%) is isolated as the by-product as a colorless foam. $[\alpha]^{19}_D$ +5.53 (c 1.16, CHCl$_3$) {enantiomer (below): $[\alpha]^{20}_D$=−5.7 (c 0.865, CHCl$_3$)}. The spectroscopic data of this by-product 44 are consistent with those obtained for the enantiomeric compound (below).

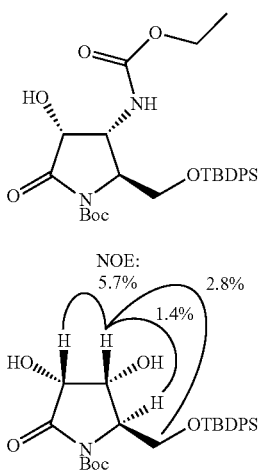

(2S,3R,4R)-tert-Butyl 2-[(tert-Butyldiphenylsilyloxy)methyl]-3-(ethoxycarbonyl-amino)-4-hydroxy-5-oxopyrrolidine-1-carboxylate (45). Lactam 40 (500 mg, 1.11 mmol) dissolved in tert-BuOH (5 mL) is treated with osmium tetroxide (28.2 mg, 0.111 mmol) and ethyl 4-chlorobenzoyloxycarbamate 7 (378 mg, 1.55 mmol) in tert-BuOH (5 mL) and water (1.7 mL) employing the procedure described for the preparation of (±)-11a and (±)-11b (above) to yield 45 (403 mg, 87%) as a colorless foam. Furthermore, a trace of 46 (12 mg, 3%) is isolated as a colorless oil.

45: $[\alpha]^{20}_D$ −31.7 (c 1.035, CHCl$_3$); FTIR (neat, cm$^{-1}$) 3405 (OH), 2932, 2858, 1787 (C=O), 1718 (C=O), 1496, 1473, 1428, 1368, 1296, 1251, 1151, 1110, 1075, 995, 960, 937, 844, 822, 777, 743, 701; $^1$H NMR (500 MHz, CDCl$_3$) δ 7.61-7.58 (m, 2H), 7.56-7.52 (m, 2H), 7.47-7.34 (m, 6H), 5.54 (s$_{br}$, 1H), 4.91 (d, J=6.3 Hz, 1H), 4.33 (dd, J=7.2, 2.8 Hz, 1H), 4.25 (s$_{br}$, 1H), 4.17-4.06 (m, 2H), 4.00 (dd, J=11.1, 2.3 Hz, 1H), 3.98-3.90 (m, 1H), 3.14 (s, 1H), 1.43 (s, 1H), 1.24 (t, J=7.1 Hz, 3H), 1.03 (s, 9H); $^{13}$C NMR (500 MHz, CDCl$_3$) δ 173.61, 149.19, 135.43, 132.47, 132.26, 130.04, 130.01, 127.95, 83.90, 69.13, 64.08, 63.29, 61.25, 51.72, 27.92, 26.86, 19.14, 14.48; HRMS (ES+) m/z calcd for C$_{29}$H$_{40}$N$_2$O$_7$SiNa$^+$ 579.2503, found 579.2508.

46: $[\alpha]^{20}_D$ −5.7 (c 0.865, CHCl$_3$); $^1$H NMR (500 MHz, CDCl$_3$) δ 7.61-7.58 (m, 2H), 7.57-7.54 (m, 2H), 7.48-7.35 (m, 6H), 4.71 (dd, J=5.1, 1.8 Hz, 1H), 4.44 (d, J=5.2 Hz, 1H), 4.12 (dd, J=3.2, 2.2 Hz, 1H), 3.94 (dd, J=11.2, 3.4 Hz, 1H), 3.83 (dd, J=11.2, 2.1 Hz, 1H), 3.08 (d, J=2.0 Hz, 1H), 2.93 (s, 1H), 1.45 (s, 9H), 1.03 (s, 9H); HRMS (ES+) m/z calcd for C$_{26}$H$_{35}$NO$_6$SiNa$^+$ 508.2131, found 508.2126.

Phenyl hydroxycarbamate (47). Hydroxylamine hydrochloride (1 g, 14.39 mmol) is

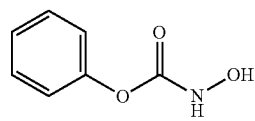

(47)

dissolved in water (30 mL) and sodium bicarbonate (2.13 g, 25.4 mmol) is added followed by CH$_2$Cl$_2$ (30 mL). The mixture is cooled in an ice bath to 0-4° C. Phenyl chloroformate (1.77 mL, 14.11 mmol) is introduced with vigorous stirring while maintaining the temperature below 4° C. After complete addition the reaction mixture is left to stir for 2 h. The biphasic reaction mixture is transferred into a separating funnel and topped up with CH$_2$Cl$_2$ until the organic phase clarified. The aqueous phase is extracted with CH$_2$Cl$_2$ (3×30 mL) and the combined organic phases are subsequently washed with brine, dried over MgSO$_4$ and concentrated to give a colourless solid. Flash column chromatography (silica gel, MeOH/CH$_2$Cl$_2$ 1:10) affords the title compound 47 (previously reported by Oesper, R.; Broker, W.; *J. Am. Chem. Soc.* 1925, 47, 2606-2608) as a colourless solid (1.0 g, 46%). $^1$H NMR (500 MHz, DMSO-d$_6$) 10.30 (br s, 1H), 9.09 (s, 1H), 7.39 (t, J=7.8 Hz, 2H), 7.22 (t, J=7.4 Hz, 1H), 7.10 (d, J=8.0 Hz, 2H); $^{13}$C NMR (125 MHz, DMSO-d$_6$) δ 155.6, 150.8, 129.5, 125.2, 121.6; HRMS (ES+) m/z calcd for C$_7$H$_7$NO$_3$Na$^+$ 176.0318, found 176.0324.

Phenyl 4-Chlorobenzoyloxycarbamate (48). To a solution of phenyl hydroxycarbamate (400 mg, 2.61 mmol) in THF (25 mL) at between −10 and 0° C. is added triethylamine (0.35 mL, 2.48 mmol). 4-Chlorobenzoyl chloride (0.32 mL, 2.48

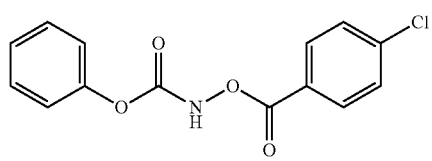

(48)

mmol) is added to the mixture dropwise ensuring that the temperature remained at about −4° C. The reaction is stirred for 30 min before ethyl acetate (40 mL) and water (20 mL) are added. The aqueous phase is separated and extracted with ethyl acetate (3×20 mL) before the combined organic phases are washed with brine, dried over $MgSO_4$ and concentrated. Flash column chromatography (silica gel, ethyl acetate/petroleum spirits 1:9 and 3:7) affords the title compound 48 (724 mg, 95%) as a colourless solid. M.p. 90.0° C. (DSC, sharp onset; phase change: 76.8° C.); $^1$H NMR (500 MHz, $CDCl_3$) δ 8.64 (s, 1H), 8.07-8.04 (m, 2H), 7.48-7.46 (m, 2H), 7.40-7.36 (m, 2H), 7.26-7.23 (m, 1H), 7.20-7.17 (m, 2H); $^{13}$C NMR (125 MHz, $CDCl_3$) δ 164.9, 154.5, 150.2, 141.1, 131.4, 129.5, 129.2, 126.2, 124.9, 121.2; HRMS (ES+) m/z calcd for $C_{14}H_{10}NO_4Na^+$ 314.0191, found 314.0187.

(9H-Fluoren-9-yl)methyl benzoyloxycarbamate (57). A solution of (9H-fluoren-9-yl)methyl hydroxycarbamate (447 mg, 1.75 mmol; for preparation see below as

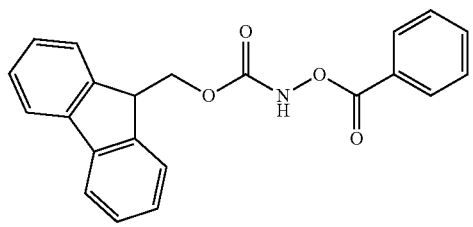 [SMILES: O=C(NOC(=O)c1ccccc1)OCC1c2ccccc2-c2ccccc21]

described for compound 56) in ethyl acetate (50 mL) is cooled to −10° C. before benzoyl chloride (0.2 mL, 1.71 mmol) is added. The solution is maintained below −10° C. as triethylamine (0.26 mL, 1.81 mmol) is added dropwise. The solution is allowed to warm to room temperature and left to stir for 1 h. Water (30 mL) and ethyl acetate is added. The aqueous layer is separated and the organic phase is washed with 10% aqueous HCl (20 mL), brine (20 mL) and dried over $MgSO_4$. Concentration yields a white powder, which was re-crystallised from ethanol to give the title compound as colourless crystals of (554 mg, 88%).

M.p. 150.1° C. (determined by differential scanning calorimetry, sharp onset); $^1$H NMR (500 MHz; $CDCl_3$) δ 8.49 (s, 1H), 8.09-8.06 (m, 2H), 7.70 (d, J=7.5 Hz, 2H), 7.65-7.61 (m, 1H), 7.57-7.54 (m, 2H), 7.50-7.46 (m, 2H), 7.36 (t, J=7.5 Hz, 2H), 7.24 (td, J=0.9, 7.5 Hz, 2H), 4.51 (d, J=7.1 Hz, 2H), 4.24 (t, J=7.1 Hz, 1H); $^{13}$C NMR (125 MHz; $CDCl_3$) δ 165.70, 156.46, 143.19, 141.26, 134.24, 129.95, 128.70, 127.83, 127.09, 126.59, 125.02, 119.99, 68.45, 46.76.

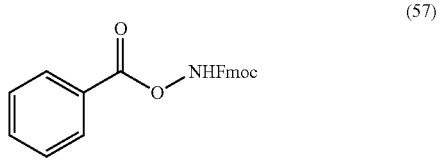

(9H-Fluoren-9-yl)methyl Benzoyloxycarbamate (57) (larger scale). Sodium bicarbonate (10.7 g, 128 mmol) was dissolved in water (190 mL) and ethyl acetate (350 mL) is added. Hydroxylamine hydrochloride (2.41 ml, 58.0 mmol) is added in one portion and the mixture is stirred vigorously for 10 min and then cooled to 0° C. A solution of FmocCl (15 g, 58.0 mmol) in ethyl acetate (30 mL) is added dropwise ensuring that the temperature of the reaction mixture does not rise above 5° C. and the reaction mixture is stirred for 4 h at ambient temperature. The phases are separated and the aqueous phase is extracted with ethyl acetate (100 mL). The combined organic phases are washed with sat. $NaHCO_3$ (100 mL) and brine (100 mL). The organic phase is concentrated under reduced pressure to give an off white solid. Ethyl acetate (50 ml) is added and the mixture is concentrated in vacuo to dryness to give an off white solid. The solid is dissolved in ethyl acetate (500 mL), cooled to −5° C. and benzoyl chloride (6.60 ml, 56.8 mmol) is added in one portion. Triethylamine (8.43 ml, 60.0 mmol) is added dropwise and the mixture is stirred for 10 minutes at −5° C. Water (200 mL) is added and the phases separated. The organic phase is washed with saturated $NaHCO_3$ solution (150 mL) and brine (150 mL). The organic phase is concentrated under reduced pressure to give an off white solid. The solid is recrystallised from hot ethanol (150-200 mL) to give the product as white crystals (16 g, 77%). $^1$H NMR (500 MHz, $CDCl_3$) δ 8.41 (s, 1H), 8.09 (d, J=8 Hz, 2H), 7.72 (d, J=7.6 Hz, 2H), 7.65 (t, J=7.5 Hz, 1H), 7.58 (d, J=7.5 Hz, 2H), 7.5 (t, J=7.8 Hz, 2H), 7.37 (t, J=7.5 Hz, 2H), 7.26 (t, J=7.5 Hz, 2H), 4.53 (d, J=7.1 Hz, 2H), 4.27 (t, J=7.0 Hz, 1H); $^{13}$C NMR (125 MHz, $CDCl_3$) δ 165.74, 156.44, 143.21, 141.30, 134.29, 128.75, 127.87, 127.13, 126.60, 125.04, 120.03, 68.5, 46.80. HRMS (ESI) m/z calcd for $C_{22}H_{17}NO_4Na^+$ 382.104, obsd 382.1050. Anal. calcd for $C_{22}H_{17}NO_4$: C, 73.53; H, 4.77; N, 3.90. Found: C, 73.60; H, 4.79; N, 4.01.

(±)-(2S,3R)-Methyl 2-Hydroxy-3-(phenoxycarbonylamino)-3-phenylpropanoate (49) and (±)-(2S,3R)-Methyl 3-Hydroxy-2-(phenoxycarbonylamino)-3-phenylpropanoate (50).

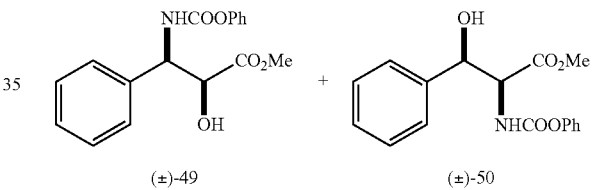

Following the general procedure, methyl cinnamate (128 mg, 0.79 mmol) is treated with phenyl 4-chlorobenzoyloxycarbamate 48 (322 mg, 1.11 mmol) in the presence of osmium tetroxide (9 mg, 0.036 mmol). Subsequent purification of the crude reaction mixture by flash column chromatography (silica gel, ethyl acetate/petroleum spirits 1:4 and 3:7) affords a mixture the title compounds 49 and 50 (232 mg, 93%). The ratio of a:b is determined to be 1:1.07 by HPLC. Analytical samples of pure 49 and 50 are obtained for structural determination.

49: $^1$H (500 MHz, $CDCl_3$) δ 7.42-7.28 (m, 7H), 7.20-7.05 (m, 3H), 6.07 (d, J=9.5 Hz, 1H), 5.30 (dd, J=1.4, 9.5 Hz, 1H), 4.50 (s, 1H), 3.82 (s, 3H), 3.47 (br s, 1H); $^{13}$C NMR (125 MHz, $CDCl_3$) δ 173.2, 154.0, 150.9, 138.5, 129.2, 128.6, 127.9, 126.8, 125.3, 121.4, 73.3, 56.7, 53.1; HRMS (ES+) m/z calcd for $C_{17}H_{17}NO_5Na^+$ 338.0999, found 338.0998.

50: $^1$H NMR (500 MHz, $CDCl_3$) δ 7.40-7.18 (m, 7H), 7.12 (t, J=7.2 Hz, 1H), 6.92 (d, J=7.9 Hz, 2H), 6.00 (d, J=9.3 Hz, 1H), 5.26 (d, J=2.8 Hz, 1H), 4.61 (dd, J=3.0, 9.4 Hz, 1H), 3.73 (s, 3H), 3.25 (br s, 1H); $^{13}$C NMR (125 MHz, $CDCl_3$) δ 170.9, 154.6, 150.7, 139.5, 129.1, 128.4, 128.1, 125.8, 125.3, 121.3, 73.3, 60.0, 52.6; HRMS (ES+) m/z calcd for $C_{17}H_{17}NO_5Na^+$ 338.0999, found 338.0995.

Methyl 3-{[(9N-Fluoren-9-yl)methoxy]carbonylamino}-2-hydroxy-4-phenylbutanoate (58a) and Methyl 2-{[(9H-Fluoren-9-yl)methoxy]carbonylamino}-3-hydroxy-4-phenylbutanoate (58b).

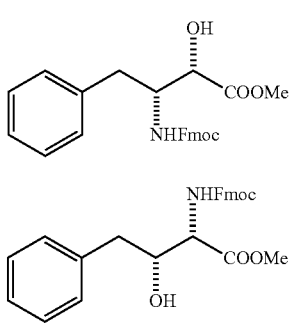

Following the general AA procedure above trans-methyl 4-phenylbut-2-enoate (140 mg, 0.79 mmol) is treated with osmium tetroxide (8 mg, 32 μmol) and Fmoc reagent 10 (380 mg, 1.0 mmol) for 3 h at room temperature. HPLC analysis of the crude product (448 mg) reveals a 2.4:1 ratio of the regioisomeric aminohydroxylation products 58a and 58b. These are purified by flash column chromatography on silica gel eluting with 10→20% ethyl acetate/petroleum spirit to give 200 mg (58%) of the major isomer 58a as a colorless syrup and 90 mg (26%) of the minor regioisomer 58b as a colorless oil.

Methyl 3-{[(9H-Fluoren-9-yl)methoxy]carbonylamino}-2-hydroxy-4-phenylbutanoate (58a) $^1$H NMR (500 MHz, CDCl$_3$) δ 7.73 (d, J=7.5 Hz, 2H), 7.51 (d, J=7.6, 11.5 Hz, 2H), 7.37 (t, J=7.4 Hz, 2H), 7.31-7.25 (m, 6H), 7.22-7.19 (m, 1H), 5.22 (d, J=9.7 Hz, 1H, NH), 4.38-4.32 (m, 1H), 4.3 (d, J=7.2 Hz, 2H), 4.15 (t, J=7.1 Hz, 1H), 4.13-4.08 (m, 1H), 3.71 (s, 3H), 3.37 (s$_{br}$, 1H, OH), 3.00-2.90 (m, 2H); $^{13}$C NMR (125 MHz, CDCl$_3$) δ 174.06, 155.73, 143.82, 143.76, 141.22, 137.25, 129.34, 128.59, 127.62, 127, 126.72, 125.01, 119.90, 70.23, 66.85, 54.71, 52.86, 47.08, 38.26; HRMS (ESI) m/z calcd for C$_{26}$H$_{25}$NO$_5$Na$^+$ 1625, obsd 454.1629.

Methyl 2-{[(9H-Fluoren-9-yl)methoxy]carbonylamino}-3-hydroxy-4-phenylbutanoate (58b) $^1$H NMR (500 MHz, CDCl$_3$) δ 7.74 (m, 2H), 7.63 (t, J 1.7 Hz, 2H), 7.42-7.16 (m, 9H), 5.71 (d, J 9.4 Hz, 1H), 4.49-4.41 (m, 3H), 4.39-4.33 (bd m, 1H), 4.23 (t, J 6.9 Hz, 1H), 2.84 (dd, J 13.8, 4.9 Hz, 1H), 2.75 (dd, J 13.6 Hz, 1H), 2.29 (s, 1H). $^{13}$C NMR (125 MHz, CDCl$_3$) δ 171.52, 156.68, 143.88, 143.64, 141.30, 141.29, 137.02, 129.36, 128.71, 127.68, 127.04, 126.86, 125.06, 119.94, 72.7, 67.1, 57.43, 52.57, 47.18, 40.24. HRMS (ESI) m/z calcd for C$_{26}$H$_{25}$NO$_5$Na$^+$ 454.1625, obsd 454.1630.

Benzyl hydroxycarbamate (51) and benzyl benzyloxycarbonyloxycarbamate (52).

Method A. Benzyl chloroformate (46.0 mL, 321 mmol) is added slowly to a solution of hydroxylamine hydrochloride (22.2 g, 321 mmol) and sodium carbonate (51.1 g, 482 mmol) in water (146 mL) keeping the temperature below 30° C. with ice-bath cooling. The ice-bath is removed and the reaction left at room temperature, however after 10 min the reaction temperature has risen to 45° C. with considerable gas evolution. A water bath is used to reduce the reaction temperature and it is stirred for an additional 1 h. The reaction is quenched by the addition of conc, hydrochloric acid until pH 1 then extracted with DCM (2×500 mL), dried over MgSO$_4$ and the solvent is removed under reduced pressure to give a residue that is purified by flash column chromatography (silica gel, petroleum spirit/ethyl acetate 7:3 and 4:1) to yield 19.0 g (35%) of benzyl hydroxycarbamate as an off-white solid and 34.9 g (36%) of the benzyl benzyloxycarbonyloxy carbamate. The analytical data for benzyl hydroxycarbamate and benzyl benzyloxycarbonyloxycarbamate is consistent with that previously reported. (Darbeau, R. W.; Alvarez, N. T.; Trahan, G. A.; Fronczek, F. R. *J. Org. Chem.* 2005, 70, 9599-9602; Knight, D. W.; Leese, M. P.; *Tetrahedron Lett.* 2001, 42, 2593-2595).

Benzyl Hydroxycarbamate (51). M.p. 62-63° C. [$^3$62-64° C.]0; $^1$H NMR (500 MHz, CHCl$_3$,) δ 7.81 (br s, 2H) 7.26 (s, 5H) 5.06 (s, 2H); $^{13}$C NMR (125 MHz, CHCl$_3$) δ 159.40, 135.54, 128.57, 128.41, 128.26, 67.77. HRMS (ES+) m/z calcd for C$_8$H$_9$NO$_3$ (M+Na)$^+$ 190.0480, found 190.0487;

Benzyl Benzyloxycarbonyloxycarbamate (52). M.p. 57.5-59° C.; $^1$H NMR (500 MHz, CHCl$_3$) δ8.32 (s, 1H), 7.30 (s, 5H), 7.28 (s, 5H), 5.17 (s, 2H), 5.13 (s, 2H); $^{13}$C NMR (125 MHz, CHCl$_3$) δ 156.59, 155.38, 135.07, 134.19, 128.98, 128.75, 128.67, 128.61, 128.52, 128.33, 71.55, 68.44; HRMS (ES+) m/z calcd for C$_{16}$H$_{15}$NO$_5$ (M+Na)$^+$ 324.0848, found 324.0850.

Method B. Hydroxylamine hydrochloride (8.31 g, 120 mmol) is dissolved in water (200 mL) followed by the introduction of sodium bicarbonate (17.7 g, 211 mmol). Then CH$_2$Cl$_2$ (200 mL) is added to the solution and resulting the mixture is cooled in an ice bath to 0-4° C. Benzyl chloroformate (16.7 mL, 117 mmol) is added with vigorous stirring while maintaining the temperature below 4° C. After addition is complete the reaction mixture is left to stir for 2 h. The biphasic reaction mixture is transferred into a separating funnel and CH$_2$Cl$_2$ is added until the organic phase clarified. The aqueous phase is extracted with CH$_2$Cl$_2$ (3×100 mL) and then washed with brine, dried over MgSO$_4$ and concentrated to give a colourless solid. Flash column chromatography (silica gel, CH$_2$Cl$_2$ then ethyl acetate/petroleum spirits 3:7 then 1:0) affords 13.7 g (70%) of 51 as a colourless solid along with 4.60 g (13%) of 52 as a colourless oil. Spectroscopic data are identical to those reported above.

Benzyl benzoyloxycarbamate (53). Triethylamine (1.66 mL, 11.8 mmol) is added dropwise to a solution of benzyl hydroxycarbamate (2.00 g, 11.9 mmol) in ethyl acetate

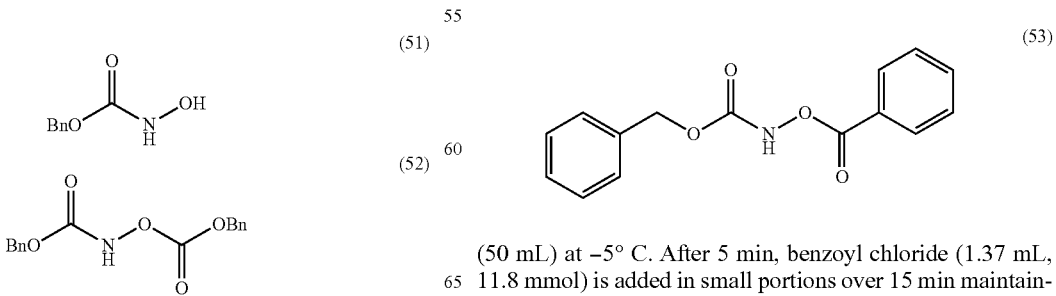

(50 mL) at −5° C. After 5 min, benzoyl chloride (1.37 mL, 11.8 mmol) is added in small portions over 15 min maintaining the temperature below −4° C. After complete addition the solution is warmed to room temperature and left to stir for 1.5 h. Water (25 mL) is added and the layers are separated. The aqueous phase is extracted with ethyl acetate (3×30 mL) before the combined organic phases are washed with brine, dried over MgSO$_4$ and concentrated to yield the title compound 53 (previously reported by Jones, L. W.; Oesper, R.; *J. Am. Chem. Soc.* 1914, 36, 2208-2223) as a colourless solid (3.16 g, 98%) which requires no further purification. M.p. 112.5° C. (DSC, sharp onset); $^1$H NMR (500 MHz, CDCl$_3$) δ 8.42 (br s, 1H), 8.10-8.07 (m, 2H), 7.65-7.61 (m, 1H), 7.49-7.46 (m, 2H), 7.38-7.32 (m, 5H), 5.25 (s, 2H); $^{13}$C NMR (125 MHz, CDCl$_3$) δ 165.8, 156.4, 135.0, 34.2, 130.0, 128.7, 128.6, 128.6, 128.3, 126.7, 68.4; HRMS (ES+) m/z calcd for C$_{15}$H$_{13}$NO$_4$Na$^+$ 294.0737, found 294.0746.

Ethyl Ethoxycarbonyloxycarbamate (54). Hydroxylamine hydrochloride (5.00 g, 72

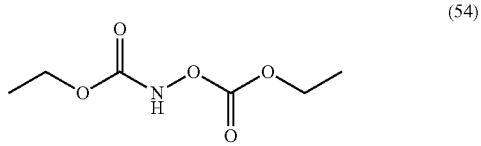

(54)

mmol) is dissolved in water (150 mL) and THF (250 mL). Ethyl chloroformate (13.8 mL, 143 mmol) is added to the solution at 0° C. followed by portionwise addition of solid sodium carbonate (19.7 g, 186 mmol). The mixture is allowed to stir overnight before diethyl ether (200 mL) and water (200 mL) are added. The aqueous phase is separated and extracted with diethyl ether (3×100 mL) and the combined organic phases are washed with brine, dried over MgSO$_4$ and concentrated. Flash column chromatography (silica gel, CH$_2$Cl$_2$/petroleum spirit 1:15 to 1:1) affords 10.5 g (82%) of the title compound 54 (previously reported by Anikumar, R.; Chandrasekhar, S.; Sridhar, M.; *Tetrahedron Lett.* 2000, 41, 5291-5293) as a colourless oil. $^1$H NMR (500 MHz, CDCl$_3$) δ 8.36 (br s, 1H), 4.36-4.29 (m, 2H), 4.28-4.23 (m, 2H), 1.39-1.33 (m, 3H), 1.32-1.27 (m, 3H); $^{13}$C NMR (125 MHz, CDCl$_3$) δ 156.6, 155.2, 66.0, 62.8, 14.1, 13.9; HRMS (ES+) m/z calcd for C$_6$H$_{11}$NO$_5$Na$^+$ 200.0529, found 200.0534.

tert-Butyl tert-Butoxycarbonyloxycarbamate (55). Hydroxylamine hydrochloride

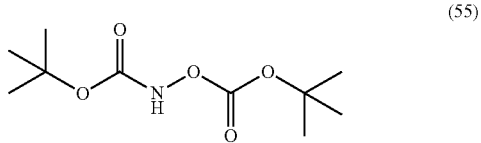 [SMILES: CC(C)(C)OC(=O)NOC(=O)OC(C)(C)C]

(55)

(2.0 g, 29 mmol) dissolved in water (40 mL) and THF (40 mL). Di-tert-butyl dicarbonate (13.2 g, 60 mmol) is added to the solution at 0° C. followed by portionwise addition of solid sodium bicarbonate (4.8 g, 57.6 mmol). The mixture is allowed to stir overnight before ethyl acetate (50 mL) and water (50 mL) are added. The aqueous phase is separated and extracted with ethyl acetate (3×30 mL) and the combined organic phases are washed with brine, dried over MgSO$_4$ and concentrated to yield the title compound 55 (previously reported by Knight, D. W.; Leese, M. P.; *Tetrahedron Lett.* 2001, 42, 2593-2595) as a white solid which requires no further purification. M.p. 52° C. (DSC, slow onset) $^1$H NMR (500 MHz, CDCl$_3$) δ 8.62 (s, 1H), 1.53 (s, 9H), 1.50 (s, 9H); $^{13}$C NMR (125 MHz, CDCl$_3$) δ 155.7, 153.6, 85.4, 83.1, 28.0, 27.6; HRMS (ES+) m/z calcd for C$_{10}$H$_{19}$NO$_5$Na$^+$ 256.1155, found 256.1165.

(9H-Fluoren-9-yl)methyl((9H-fluoren-9-yl)methoxy)carbonyloxycarbamate (56).

Sodium bicarbonate (15.96 g, 190 mmol) is added to a biphasic mixture of

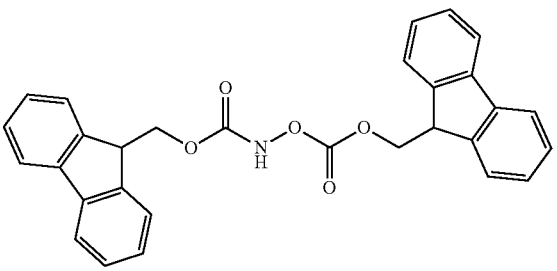 [SMILES: O=C(NOC(=O)OCC1c2ccccc2-c2ccccc21)OCC1c2ccccc2-c2ccccc21]

hydroxylamine hydrochloride (6.0 g, 86 mmol) in CH$_2$Cl$_2$ (250 mL) and water (100 mL) at 0° C. After 10 mins, solid FmocCl (21 g, 81 mmol) is added portionwise with vigorous stirring. After 1 h a white precipitate forms and more CH$_2$Cl$_2$ (100 mL) is added. The solution is allowed to warm to 20° C. and left to stir for 3 d. The white solid that remains is filtered away, re-dissolved in ethyl acetate (300 mL), washed with brine and dried over MgSO$_4$ to yield (9H-fluoren-9-yl)methyl hydroxycarbamate (Mellor, S. L.; McGuire, C.; Chan, W. C.; *Tet. Lett.*, 1997, 38, 3311-3314) as a white solid (15 g, 68%). Furthermore, the mother-liquor is concentrated and purified by column chromatography (silica gel, ethyl acetate/CH$_2$Cl$_2$ 1:1 to 1:0) to yield the title compound (by-product) as a white solid (0.55 g, 1%).

M.p. 160.5° C. (determined by differential scanning calorimetry, sharp onset); $^1$H NMR (500 MHz; CDCl$_3$) δ 7.95 (s, 1H), 7.77-7.74 (m, 4H), 7.63-7.57 (m, 4H), 7.43-7.38 (m, 4H), 7.32-7.28 (m, 4H), 4.52 (2×d, J=7.1, 7.5, 4H), 4.31 (t, J=7.5 Hz, 1H), 4.26 (t, J=7.1 Hz, 1H); $^{13}$C NMR (125 MHz; CDCl$_3$) δ 156.29, 155.34, 143.15, 142.73, 141.33, 128.12, 127.96, 127.32, 127.22, 125.17, 125.05, 120.17, 120.09, 71.91, 68.70, 46.80, 46.52; m/z calcd for C$_{30}$H$_{23}$NO$_5$ (M+Na)$^+$ 500.1468, found 500.1469.

(9H-Fluoren-9-yl)methyl (2R,3R,4S)-4-Hydroxy-2-[(2S,5R)-2-isopropyl-5-methyl-cyclohexyloxy]-5-oxotetrahydrofuran-3-ylcarbamate (59).

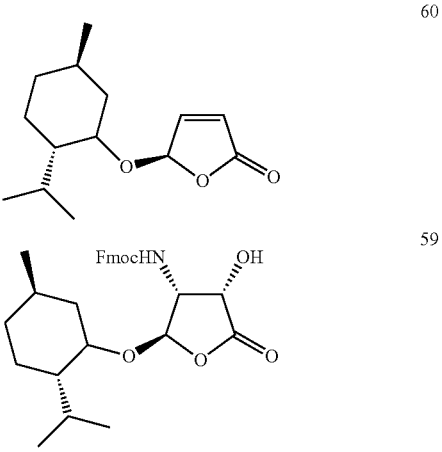

Following the general procedure (K)-5-[(1R)-menthyloxy]-2 (5H)-furanone 60 (100 mg, 0.42 mmol) is treated with osmium tetroxide (4.3 mg, 0.017 mmol) and Fmoc reagent 10 (231.4 mg (0.5874 mmol) at room temperature overnight. The crude product is purified by flash, column chromatography (SiO$_2$, ethyl acetate/petroleum spirit 1:4 and 3:7) to yield 153 mg (74%) of 59 as a colorless foam. [α]$^{20}_D$=−49 (c 0.545, CHCl$_3$); FTIR (neat, cm$^{-1}$) 3349, 2954, 1787, 1708, 1450, 1263, 1104, 909, 758, 740; $^1$H NMR (500 MHz, CDCl$_3$) ☐ δ 7.76 (d, J=7.8 Hz, 2H), 7.60-7.55 (m, 2H), 7.40 (t, J=7.5 Hz, 2H), 7.31 (tt, J=1.4, 7.5 Hz, 2H), 5.73 (s, 1H), 5.43 (d, J=3 Hz, 1H), 4.77 (d, J=5 Hz, 1H), 4.47-4.39 (m, 2H), 4.22 (d, J=6.9 Hz, 1H), 4.19 (dd, J=3.5, 6.5 Hz, 1H), 3.51 (td, J=4.2, 10.7 Hz, 1H), 3.12 (J=2.6 Hz, 1H), 2.20-2.09 (m, 1H), 1.95 (sept/d, J=2.7, 7 Hz, 1H), 1.69-1.61 (m, 2H), 1.43-1.31 (m, 1H), 1.28-1.20 (m, 1H), 1.03-0.80 (m, 6H), 0.87 (d, J=7.1 Hz, 3H), 0.74 (d, J=7 Hz, 3H); $^{13}$C NMR (125 MHz, CDCl$_3$) δ 175.82, 156.33, 143.65, 143.50, 141.33, 127.82, 127.11, 125.01, 120.05, 101.89, 78.46, 67.35, 66.60, 55.99, 47.47, 47.07, 39.48, 34.21, 31.38, 25.66, 23.02, 22.13, 20.83, 15.5; HRMS (ESI) m/z calcd for C$_{29}$H$_{35}$NO$_6$Na$^+$ 516.2362, obsd 516.2368. Anal. calcd for C$_{29}$H$_{35}$NO$_6$: C, 70.57; H, 7.15; N, 2.84. Found: C, 70.39; H, 7.21; N, 2.76.

Although the invention has been described by way of example, it should be appreciated that variations or modifications may be made without departing from the scope of the invention. Furthermore, when known equivalents exist to specific features, such equivalents are incorporated as if specifically referred to in the specification.

Industrial Applicability

The invention relates to a process for the aminohydroxylation of alkenes using N-oxycarbamate reagents. The invention particularly relates to an intermolecular aminohydroxylation reaction carried out in the absence of added base. The invention also relates to novel N-acyloxycarbamate reagents. The process of the invention is useful in the synthesis of compounds having a vicinal amino alcohol moiety, such as biologically active compounds.

The invention claimed is:

1. A process for preparing a β-hydroxycarbamate compound form an alkene, using an aminohydroxylation reaction, the process including the step of:

reacting the alkene with an N-oxycarbamate compound, in the presence of an osmium compound as a catalyst, to give the β-hydroxycarbamate compound;

where the process is carried out in the absence of added base and where the N-oxycarbamate compound is a compound of formula (II):

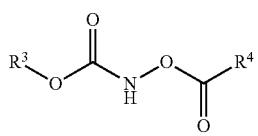

(II)

where

R$^3$ is an optionally substituted alkyl group, an optionally substituted aralkyl group or an optionally substituted aryl group;

R$^4$ is a radical of formula (ii)

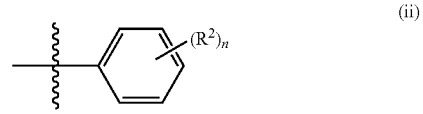

(ii)

or R$^4$ is OR$^5$;

R$^2$ is halogen, alkyl, alkoxy, dialkylamino, trialkylammonium, nitro, carboxy alkyl ester, alkylamide, —SO$_3$H, —PO$_3$H$_2$ or —COOH, where, when n is greater than 1, each R$^2$ is independently selected;

R$^5$ is an optionally substituted alkyl group or an optionally substituted aralkyl group; and n is 0, 1, 2, 3, 4 or 5;

provided that the following compounds are excluded:

the compound where: R$^3$ is t-butyl; R$^4$ is a radical of formula (ii) where R$^2$ is Cl and n is 3; and the compound where: R$^3$ is t-butyl; R$^4$ is a radical of formula (ii) where R$^2$ is methyl and n is 3.

2. A process as claimed in claim 1 wherein the N-oxycarbamate is an N-acyloxycarbamate compound of formula (I):

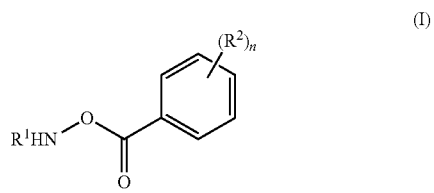

(I)

wherein:

R$^1$ is a radical of formula (iii)

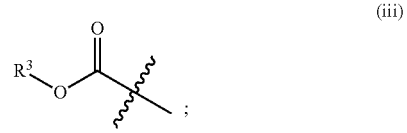

(iii)

R$^3$ is an optionally substituted alkyl group, an optionally substituted aralkyl group or an optionally substituted aryl group;

provided that the following compounds are excluded:

the compound where: R$^1$ is a radical of formula (iii) where R$^3$ is t-butyl; R$^2$ is Cl and n is 3; and the compound where: R$^1$ is a radical of formula (iii) where R$^3$ is t-butyl; R$^2$ is methyl and n is 3.

3. A process as claimed in claim 1, wherein the N-oxycarbamate is an N-alkyloxycarbonyloxycarbamate or an N-aralkoxycarbonyloxycarbamate compound of formula (III):

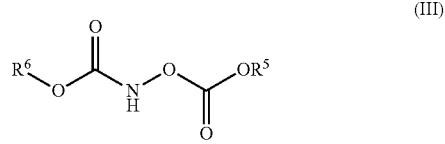

(III)

wherein:

R[5] is an optionally substituted alkyl group or an optionally substituted aralkyl group; and R[6] is an optionally substituted alkyl group or an optionally substituted aralkyl group.

4. A process according to claim 1, wherein the osmium catalyst is osmium tetroxide, potassium osmate(VI) dehydrate, osmium(III) trichloride or an immobilized osmium catalyst.

5. A process according to claim 1 wherein the reaction of the alkene and the N-oxycarbamate, N-acyloxycarbamate, N-alkyloxycarbonyloxycarbamate or N-aralkoxycarbonyloxycarbamate compound is carried out in an organic solvent containing water.

6. A process as claimed in claim 2 wherein the reaction of the alkene and the N-acyloxycarbamate compound is carried out in the presence of a chiral ligand.

7. A process as claimed in claim 6 where the chiral ligand is (DHQ)$_2$PHAL, (DHQD)$_2$PHAL or (DHQ)$_2$AQN.

8. A process as claimed in claim 1 wherein the reaction of the alkene and the N-oxycarbamate, N-acyloxycarbamate, N-alkyloxycarbonyloxycarbamate or N-aralkoxycarbonyloxycarbamate compound is carried out in a mixed solvent system selected from the group consisting of acetonitrile/water, isopropanol/water, t-butanol/water, acetone/water, tetrahydrofuran/water, dioxane/water and dimethylformamide/water.

9. A process as claimed in claim 1 wherein R$^2$ is a halogen.

10. A process as claimed in claim 2 R$^1$ is EtO$_2$C, MeO$_2$C, 2-trimethylsilylethoxycarbonyl, phenoxycarbonyl, 2,2,2-trichloroethoxycarbonyl, benzyloxycarbonyl, t-butoxycarbonyl or 9fluorenylmethoxycarbonyl.

11. A process as claimed in claim 1 wherein n is 1.

12. A process as claimed in claim 1 wherein R$^5$ is ethyl, tert-butyl, 9-fluorenylmethyl or benzyl.

13. A process as claimed in claim 3 wherein R$^5$ and R$^6$ are the same.

14. A process as claimed in claim 1 wherein the N-oxycarbamate compound is an N-acyloxycarbamate compound selected from the group consisting of:

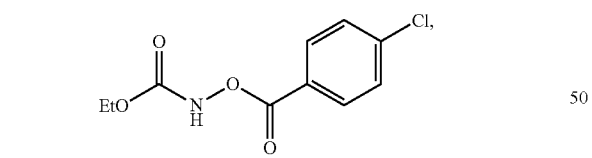

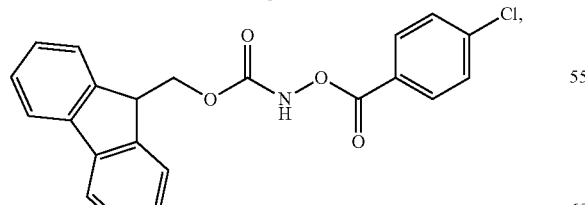

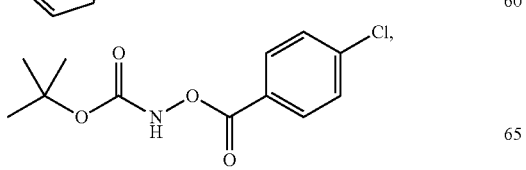

15. A process as claimed in claim 1 wherein the N-oxycarbamate compound is an N-alkyloxycarbonyloxycarbamate or N-aralkoxycarbonyloxycarbamate compound selected from the group consisting of:

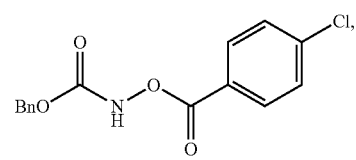

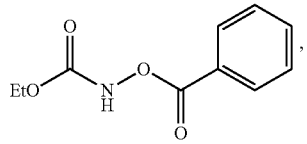

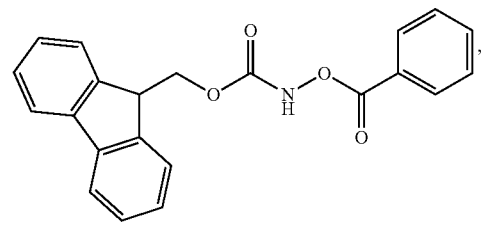

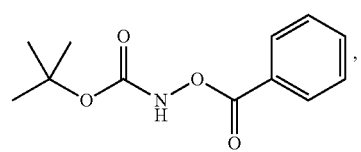

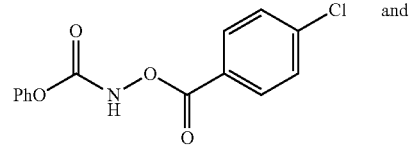  and

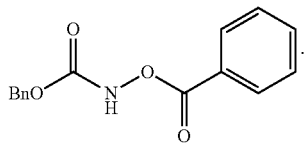 [SMILES: O=C(NOC(=O)c1ccccc1)OCc1ccccc1]

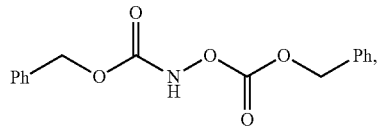

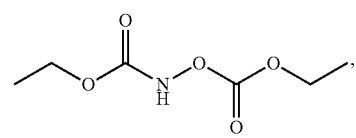

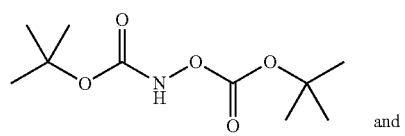  and

-continued
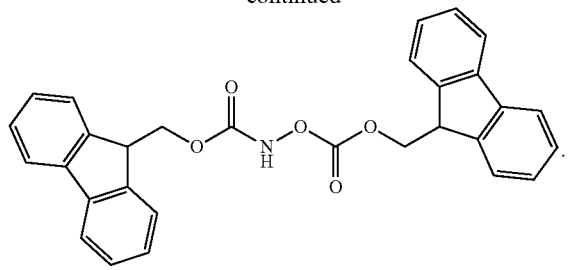
16. A compound selected from the group consisting of:
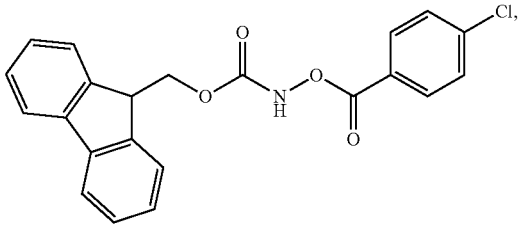
-continued
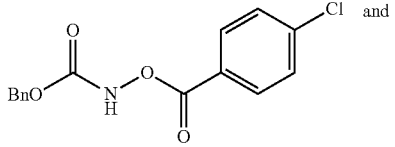
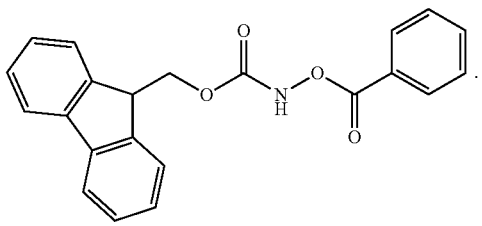
* * * * *

UNITED STATES PATENT AND TRADEMARK OFFICE
CERTIFICATE OF CORRECTION

PATENT NO. : 8,987,504 B2
APPLICATION NO. : 13/704896
DATED : March 24, 2015
INVENTOR(S) : Simon Peter Harold Mee et al.

It is certified that error appears in the above-identified patent and that said Letters Patent is hereby corrected as shown below:

In The Claims

Column 75, Line 29:
"10. A process as claimed in claim 2 $R^1$ is $EtO_2C$, $MeO_2C$," should read, --10. A process as claimed in claim 2 wherein $R^1$ is $EtO_2C$, $MeO_2C$,--.

Column 75, Line 32:
"bonyl or 9fluorenylmethoxycarbonyl." should read, --bonyl or 9-fluorenylmethoxycarbonyl.--.

Signed and Sealed this
Seventeenth Day of May, 2016

Michelle K. Lee
*Director of the United States Patent and Trademark Office*